(12) United States Patent
Gypser et al.

(10) Patent No.: US 6,200,997 B1
(45) Date of Patent: Mar. 13, 2001

(54) HETEROCYCLYL-SUBSTITUTED PHENYL COMPOUNDS, PROCESSES AND INTERMEDIATES FOR THEIR PREPARATION AND THEIR USE FOR CONTROLLING HARMFUL FUNGI AND ANIMAL PESTS

(75) Inventors: Andreas Gypser; Hubert Sauter; Herbert Bayer, all of Mannheim; Markus Gewehr, Kastellaun; Wassilios Grammenos, Ludwigshafen; Thomas Grote, Schifferstadt; Roland Götz, Ludwigshafen; Bernd Müller, Frankenthal; Arne Ptock, Ludwigshafen; Franz Röhl, Schifferstadt; Volker Harries, Frankenthal; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/236,108

(22) Filed: Jan. 25, 1999

(30) Foreign Application Priority Data

Feb. 5, 1998 (GB) .................................................. 19804485

(51) Int. Cl.$^7$ ........................... A01N 43/82; A01N 43/64; C07D 271/06; C07D 249/12; C07D 317/00
(52) U.S. Cl. ................ 514/360; 514/364; 514/376; 514/384; 548/132; 548/227; 548/263.4; 549/450
(58) Field of Search .................... 514/376, 384, 514/364, 360; 548/132, 227, 263.4; 549/450

(56) References Cited

FOREIGN PATENT DOCUMENTS

| | | |
|---|---|---|
| 4020384 | 1/1992 | (DE) . |
| 253213 | 1/1988 | (EP) . |
| 398692 | 11/1990 | (EP) . |
| 95/14009 | 5/1995 | (WO) . |
| 95/21153 | 8/1995 | (WO) . |
| 96/26191 | 8/1996 | (WO) . |
| 96/36229 | 11/1996 | (WO) . |
| 96/36615 | 11/1996 | (WO) . |
| 96/36616 | 11/1996 | (WO) . |
| 96/36633 | 11/1996 | (WO) . |
| 96/38425 | 12/1996 | (WO) . |
| 97/00612 | 1/1997 | (WO) . |
| 97/02255 | 1/1997 | (WO) . |
| 97/05103 | 2/1997 | (WO) . |
| 97/05120 | 2/1997 | (WO) . |
| 97/15552 | 5/1997 | (WO) . |

*Primary Examiner*—Joseph K. McKane
*Assistant Examiner*—Joseph Murray
(74) *Attorney, Agent, or Firm*—Keil & Weinkauf

(57) ABSTRACT

The present invention relates to heterocyclyl-substituted phenyl compounds of the formula I,

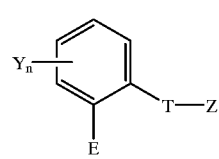

(I)

where the substituents have the following meanings:

Y is halogen, $C_1$–$C_4$-alkyl, $C_1$–$C_4$-haloalkyl or $C_1$–$C_4$-alkoxy;

n is 0, 1 or 2, where the radicals Y may be different if n=2;

E is a group A or B,

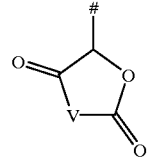

(A)

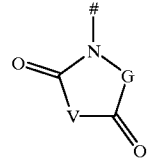

(B)

where # denotes the bond to the phenyl ring, and G $R^\alpha$, $R^\beta$, Y, n, T and Z are each as defined in the description.

8 Claims, No Drawings

HETEROCYCLYL-SUBSTITUTED PHENYL COMPOUNDS, PROCESSES AND INTERMEDIATES FOR THEIR PREPARATION AND THEIR USE FOR CONTROLLING HARMFUL FUNGI AND ANIMAL PESTS

The present invention relates to heterocyclyl-substituted phenyl compounds of the formula I,

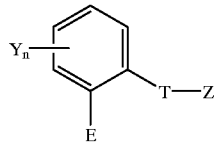

where:
Y is halogen, $C_1$–$C_4$-alkyl, $C_1$–$C_4$-haloalkyl or $C_1$–$C_4$-alkoxy;
n is 0, 1 or 2, where the radicals Y may be different if n=2;
E is a group A or B,

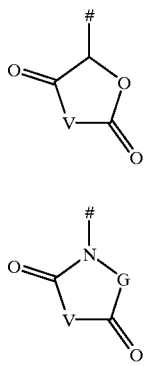

where # denotes the bond to the phenyl ring;
V is oxygen or N—$R^\alpha$, and
G is N—$R^\beta$, where
$R^\alpha$ is $C_1$–$C_4$-alkyl, $C_1$–$C_4$-haloalkyl, $C_3$–$C_6$-cycloalkyl or is arylmethylene with or without substitution;
$R^\beta$ is hydrogen or a radical $R^\alpha$;
T is oxygen or oxymethylene;
Z is a group X, N=CW$R^1$ or N=C($R^1$)—C($R^2$)=NO$R^3$;
X is heterocyclyl with or without substitution, aryl with or without substitution, hetaryl with or without substitution, arylmethylene with or without substitution or hetarylmethylene with or without substitution;
W is $C_1$–$C_6$-alkyl with or without substitution, $C_2$–$C_6$-alkenyl with or without substitution, $C_2$–$C_6$-alkynyl with or without substitution, $C_3$–$C_6$-cycloalkyl with or without substitution, $C_3$–$C_6$-cycloalkenyl with or without substitution, heterocyclyl with or without substitution, aryl with or without substitution or hetaryl with or without substitution;
$R^1$ is hydrogen, cyano, $C_1$–$C_4$-alkyl, $C_1$–$C_4$-haloalkyl, $C_1$–$C_4$-alkoxy, $C_1$–$C_4$-alkoxy-$C_1$–$C_4$-alkyl, $C_3$–$C_6$-cycloalkyl;
$R^2$ is hydrogen, cyano, halogen, C($R^d$)=NO$R^3$ or W, OW, SW or N$R^c$W, where
$R^c$ is hydrogen, $C_1$–$C_6$-alkyl, $C_2$–$C_6$-alkenyl or $C_2$–$C_6$-alkynyl and
$R^d$ is hydrogen or $C_1$–$C_6$-alkyl;
$R^3$ is hydrogen, $C_1$–$C_6$-alkyl with or without substitution, $C_2$–$C_6$-alkenyl with or without substitution or $C_2$–$C_6$-alkynyl with or without substitution.

Additionally, the invention relates to processes and intermediates for preparing the compounds I and to the use of the compounds I for controlling harmful fungi and animal pests.

WO-A 95/14,009 and WO-A 97/02,255 disclose 4-phenyl-2,3-dihydroisoxazolones and 4-phenyl-2,4-dihydrotriazolones having substituents in the ortho position.

α-Phenylacrylic acid and α-phenyl-α-methoximinoacetic acid derivatives having an aryl or hetaryl substituent in the ortho position are described in EP-A 253 213 and EP-A 398 692, those having an oxime ether group in the ortho position are described in DE-A 40 20 384, those having a bisoxime ether group are described in WO-A 95/21,153 and WO-A 97/05,103 and those having a trisoxime ether group are described in WO-A 97/15,552.

WO-A 95/14,009, WO-A 96/26,191, WO-A 96/36,229, WO-A 96/36,615, WO-A 96/36,616, WO-A 96/38,425, WO-A 97/00,612 and WO-A 97/05,120 disclose cyclic amides which carry an ortho-substituted phenyl ring in the position ortho to the amide carbonyl group. WO-A 96/36,633 discloses cyclic amides which carry a substituted heterocycle in the position ortho to the amide carbonyl group.

The compounds described in the abovementioned publications are suitable for use as crop protection agents against harmful fungi and, in some instances, against animal-pests.

However, in many cases their activity is unsatisfactory.

It is an object of the present invention to provide compounds having an improved activity.

We have found that this object is achieved by the substituted phenyl compounds of the formula I. Furthermore, we have found intermediates and processes for preparing the compounds I, and the use of the compounds I and of compositions comprising them for controlling harmful fungi and animal pests. Preference is given to the fungicidal activity.

The compounds of the formula I differ from the compounds which are known from the abovementioned publications in the design of the group E: in the compounds of the formula IA, the group E is a dioxolanedione if V is oxygen and an oxazolidinedione if V is N—$R^\alpha$. In the compounds of the formula IB, the group E is an oxadiazolidinedione if V is oxygen and a triazolidinedione if V is N—$R^\alpha$.

Compared with the prior art compounds, the compounds of the formula I have increased activity against harmful fungi and animal pests.

The compounds I can be obtained by various routes, it being immaterial for the synthesis whether the heterocycles E or the group T—Z is built up first. For clarity, the term $E^\#$ is therefore used for group A or B, or an appropriate precursor thereof, and $Z^\#$ is used for the group T—Z, or a suitable precursor thereof in the descriptions of the reactions hereinbelow.

For compounds of the formula IA

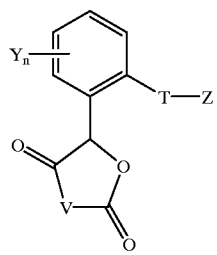

(IA)

preference is given to introducing the group T—Z at the stage where $E^\#$ is C(OH)COOR', where R' is $C_1$–$C_4$-alkyl.

For compounds of the formula IB

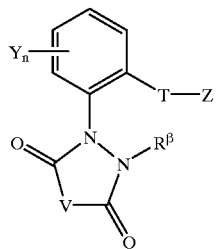

(IB)

preference is given to introducing the group T—Z at the stage where $E^\#$ is NH—$NH_2$.

The group T—Z in the compounds of the formula I can be obtained by methods similar to those described in WO-A 96/07,633, or WO-A 97/24,317.

The synthesis route described hereinbelow is equally suitable for compounds of the formulae I in which T is oxygen or oxymethylene.

The oxazolidinediones of the formula $IAa^\#$ are obtained in a particularly advantageous manner by acylating an alkyl α-hydroxy-α-phenylacetate of the formula $IIA^\#$ with phosgene or a phosgene equivalent to give dicarbonyl compounds of the formula $IIIA^\#$, which are cyclized by reaction with primary amines of the formula IVa to give the oxadiazolidinediones of the formula $IAa^\#$.

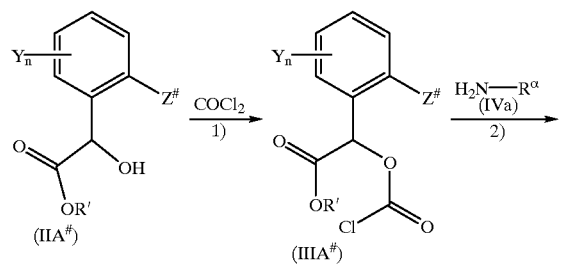

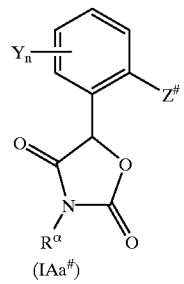

(IAa#)

In the formula $IIA^\#$, R' is $C_1$–$C_4$-alkyl. Compounds of the formula $IIA^\#$ are known from the literature, or they can be prepared by methods known from the literature [cf. WO-A 96/07,633].

1) The reaction of $IIA^\#$ with phosgene or a phosgene equivalent, such as, for example, di- or triphosgene, is usually carried out at from –10° C. to 250° C., preferably at from 10° C. to 110° C., in an inert organic solvent in the presence of a base or a catalyst [cf. Chem. Ber., 72 (1972), p. 457; Chem. Soc. Rev., 3 (1974), p. 209; Angew. Chem., 107 (1995), p. 2746].

Suitable solvents are aliphatic hydrocarbons, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles, and also dimethyl sulfoxide, dimethylformamide and dimethylacetamide, particularly preferably tetrahydrofuran, dimethylformamide, chlorobenzene and toluene. It is also possible to employ mixtures of the abovementioned solvents.

Suitable bases are, in general, inorganic compounds, such as alkali metal and alkaline earth metal hydroxides, alkali metal and alkaline earth metal oxides, alkali metal and alkaline earth metal hydrides, alkali metal amides, alkali metal and alkaline earth metal carbonates, and also alkali metal bicarbonates, organometallic compounds, in particular alkali metal alkyls, alkylmagnesium halides, and furthermore organic bases, for example tertiary amines such as trimethylamine, triethylamine, triisopropylethylamine and N-methylpiperidine, pyridine, substituted pyridines such as collidine, lutidine and 4-dimethylaminopyridine and also bicyclic amines. Particular preference is given to triethylamine and pyridine. The bases are generally employed in equimolar amounts, in excess or, if appropriate, as solvent.

The starting materials are generally reacted with one another in equimolar amounts. It may be advantageous in terms of yield to employ phosgene or the phosgene equivalent in excess, based on $IIA^\#$.

2) This reaction is usually carried out at from –10° C. to 250° C., preferably at from 0° C. to 100° C., in an inert organic solvent [cf. Chem. Ber., 33. (1900), p. 455 ff.]. Suitable solvents are aliphatic hydrocarbons, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles, alcohols such as methanol, ethanol, n-propanol, isopropanol, n-butanol and tert-butanol and also dimethyl sulfoxide, dimethylformamide and dimethylacetamide, particularly preferably toluene, tetrahydrofuran, dimethylformamide, chlorobenzene and ethanol. It is also possible to employ mixtures of the abovementioned solvents.

The educts are generally reacted with each other in equimolar amounts. In terms of yield, it may be advantageous to employ an excess of IVa, based on IIIA#.

If the dicarbonyl compounds IIIA# in the reaction with IVa do not cyclize unaided, the oxadiazolidinediones can be formed by hydrolyzing the ester group in the compounds IIIA#, followed by treatment with acid.

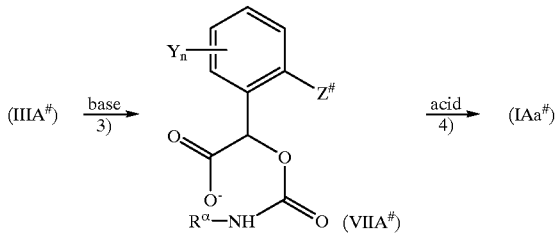

3) The hydrolysis is usually carried out at from 10° C. to 150° C., preferably at from 20° C. to 100° C., in an inert organic solvent in the presence of a base [cf. Chem. Zentralblatt, (1901) p. 936 ff.].

Suitable solvents are aliphatic hydrocarbons, aromatic hydrocarbons, ethers such as diethyl ether, diisopropyl ether, tert-butyl methyl ether, dioxane, anisole and tetrahydrofuran, alcohols such as methanol, ethanol, n-propanol, isopropanol, n-butanol and tert-butanol and also dimethyl sulfoxide, dimethylformamide and dimethylacetamide, particularly preferably methanol, ethanol, n-propanol, diethyl ether and dimethylformamide. It is also possible to employ mixtures of the abovementioned solvents.

Suitable bases are, in general, inorganic compounds such as alkali metal and alkaline earth metal hydroxides such as lithium hydroxide, sodium hydroxide, potassium hydroxide and calcium hydroxide, alkali metal and alkaline earth metal oxides, alkali metal and alkaline earth metal carbonates and also alkali metal bicarbonates. Particular preference is given to sodium hydroxide and potassium hydroxide.

The starting materials are generally reacted with one another in equimolar amounts. In terms of yield, it may be advantageous to employ an excess of base, based on IIIA#.

4) The cyclization is usually carried out from 10° C. to 150° C., preferably at from 20° C. to 100° C., in an inert organic solvent in the presence of an acid [cf. Chem. Zentralblatt, (1901), p. 936 ff.].

Suitable solvents are aliphatic hydrocarbons, aromatic hydrocarbons, halogenated hydrocarbons, ethers such as diethyl ether, diisopropyl ether, tert-butyl methyl ether, dioxane, anisole and tetrahydrofuran, nitriles, alcohols such as methanol, ethanol, n-propanol, isopropanol, n-butanol and tert-butanol and also dimethyl sulfoxide, dimethylformamide and dimethylacetamide, particularly preferably methanol, ethanol, diethyl ether and tert-butyl methyl ether. It is also possible to employ mixtures of the abovementioned solvents.

Suitable acids and acid catalysts are inorganic acids such as hydrofluoric acid, hydrochloric acid, hydrobromic acid, sulfuric acid and perchloric acid, and also organic acids such as formic acid, acetic acid, propionic acid, oxalic acid, citric acid and trifluoroacetic acid.

The starting materials are generally reacted with one another in equimolar amounts. In terms of yield, it may be advantageous to employ an excess of acid, based on VIIA#.

Intermediates of the formula 1,

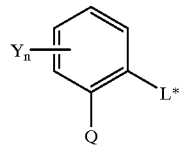

where Q is CH(COOR')OCOCl, CH(COOH)OCOCl, CH(COOR')OCONHR$^\alpha$, CH(COOH)OCONHR$^\alpha$, or a group A and L* is CH$_2$L' or a group L', where L' is a nucleophilically cleavable group and R' is C$_1$–C$_4$-alkyl, are novel.

The triazolidinediones of the formula IBa# are obtained in a particularly advantageous manner by converting phenylhydrazines of the formula IIB# with alkyl chloroformates into carbamates of the formula IIIB# which are acylated with phosgene or a phosgene equivalent to give dicarbonyl compounds of the formula VB#.

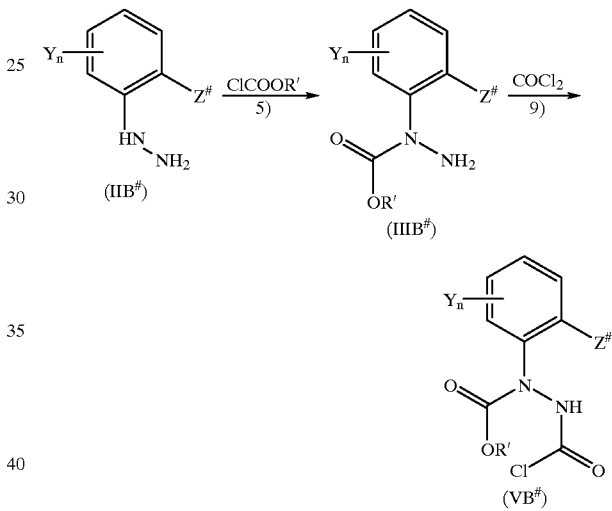

In the formula IIIB#, R' is C$_1$–C$_4$-alkyl. The compounds VB# are cyclized by reaction with primary amines of the formula IVa to give the triazolidinediones of the formula IBa#.

5) The reaction of IIB# with alkyl chloroformates to give carbamates of the formula IIIB# is usually carried out at from 0° C. to 200° C., preferably at from 20° C. to 150° C., using lower alkyl chloroformates in an inert organic solvent, generally in the presence of a base or an acid [cf. Synth. Commun. 15 (1985), p. 697].

Suitable solvents are aliphatic hydrocarbons, aromatic hydrocarbons, halogenated hydrocarbons, ethers such as diethyl ether, diisopropyl ether, tert-butyl methyl ether, dioxane, anisole and tetrahydrofuran, nitriles, ketones, alcohols such as methanol, ethanol, n-propanol, isopropanol, n-butanol and tert-butanol, and also dimethyl sulfoxide, dimethylformamide and dimethylacetamide, particularly preferably ethanol, dimethylformamide, tetrahydrofuran and diethyl ether. It is also possible to employ mixtures of the abovementioned solvents.

Suitable bases are, in general, inorganic compounds, such as alkali metal and alkaline earth metal hydroxides such as lithium hydroxide, sodium hydroxide, potassium hydroxide and calcium hydroxide, alkali metal and alkaline earth metal oxides, alkali metal and alkaline earth metal hydrides such as lithium hydride, sodium hydride, potassium hydride and calcium hydride, alkali metal amides, alkali metal and alkaline earth metal carbonates such as lithium carbonate, potassium carbonate and calcium carbonate, and also alkali metal bicarbonates such as sodium bicarbonate, organometallic compounds, in particular alkali metal alkyls, alkylmagnesium halides and also alkali metal and alkaline earth metal alkoxides such as sodium methoxide, sodium ethoxide, potassium ethoxide, potassium tert-butoxide and dimethoxymagnesium, furthermore organic bases, for example tertiary amines such as trimethylamine, triethylamine, triisopropylethylamine and N-methylpiperidine, pyridine, substituted pyridines such as collidine, lutidine and 4-dimethylaminopyridine and also bicyclic amines. Particular preference is given to triethylamine, sodium hydride, sodium ethoxide and potassium ethoxide and sodium hydroxide and potassium hydroxide. The bases are generally employed in catalytic amounts, however, it is also possible to employ them in equimolar amounts, in excess or, if appropriate, as solvent.

Suitable acids and acid catalysts are inorganic acids, such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and also organic acids such as formic acid, acetic acid, propionic acid, oxalic acid, citric acid and trifluoroacetic acid. The acids are generally employed in catalytic amounts, however, it is also possible to employ them in equimolar amounts, in excess or, if appropriate, as solvent.

Phenylhydrazines $IIB^{\#}$ and alkyl chloroformates are generally reacted with each other in equimolar amounts. It may be advantageous in terms of yield to employ an excess of alkyl chloroformates, based on $IIB^{\#}$.

Phenylhydrazines $IIB^{\#}$ can be obtained by methods known from the literature from the corresponding nitro compounds $IIB1^{\#}$ by reduction of the nitro group and diazotization of the resulting anilines $IIB2^{\#}$, which are reduced to give the phenylhydrazines $IIB^{\#}$.

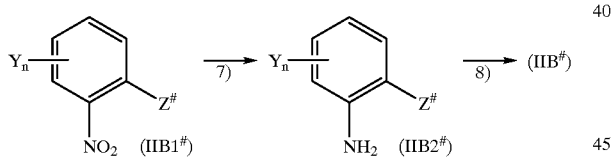

7) The reduction of the nitro group $IIB1^{\#}$ can be carried out under customary conditions, preferably by catalytic hydrogenation, by reduction with iron, tin or zinc in the presence of an acid, by reduction with alkali metals in the presence of a base or by enzyme-catalyzed reduction [cf. Houben-Weyl, Vol. IV/1c, 4th edition, p. 506ff., Thieme Verlag Stuttgart and New York (1980); ibid. Vol. IV/1d, 4th edition, p. 473ff. (1981); Heterocycles 31 (1990), 2201]

Some of the nitrobenzene derivatives of the formula $IIB1^{\#}$ are known from the literature [cf. EP-A 498 396; WO-A 93/15,046; WO-A 95/14,009], or they can be prepared in accordance with the literature cited.

8a) The reaction of $IIB2^{\#}$ with nitrite is carried out at from −10° C. to 25° C., preferably at from −5° C. to 10° C., in water or in an inert organic solvent in the presence of an acid [cf. Organikum, 15th edition 1976, p. 654ff., VEB Verlag der Wissenschaften, Berlin].

8b) The reduction of the diazo compound can be carried out under customary conditions, preferably by reduction with iron, tin or zinc or salts thereof in the presence of an acid or by reduction with alkali metals in the presence of a base [cf. Houben-weyl, Vol. IV/1c, 4th edition, p. 506ff., Thieme Verlag Stuttgart and New York (1980); ibid. Vol. IV/1d, 4th edition, p. 473ff. (1981); Heterocycles, 31 (1990), 2201]. Furthermore, preference is given to reducing the diazonium salts with sulfite or disulfite [cf.: Organikum, 15th edition, VEB, Verlag der Wissenschaften, Berlin, p. 662, 1976; J. Chem. Soc, (1927), 1325ff.; Chem. Ber., 55 (1922), 1827; Houben-Weyl, Vol. 10/2, p. 182, Thieme Verlag, Stuttgart].

9) The reaction of the carbamates $IIIB^{\#}$ with phosgene or a phosgene equivalent is carried out under the conditions described in section 1) for the acylation of $IIA^{\#}$ to give the dicarbonyl compounds $IIIA^{\#}$.

The triazolidinediones of the formula $IBa^{\#}$ are obtained in a particularly advantageous manner by cyclizing the dicarbonyl compounds of the formula $VB^{\#}$ by reaction with primary amines of the formula IVa

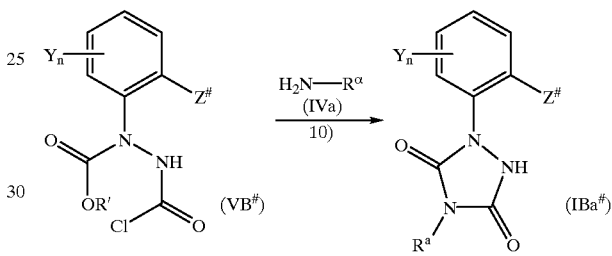

10) The cyclization of $VB^{\#}$ to give the triazolidinediones $IBa^{\#}$ is carried out under the conditions described in section 2) for the cyclization of the dicarbonyl compounds $IIIA^{\#}$.

If the dicarbonyl compounds $VB^{\#}$ do not cyclize unaided in the reaction with IVa, the oxadiazolidinediones can be formed by hydrolysis of the ester group in the compounds $VIIB^{\#}$ and subsequent treatment with acid.

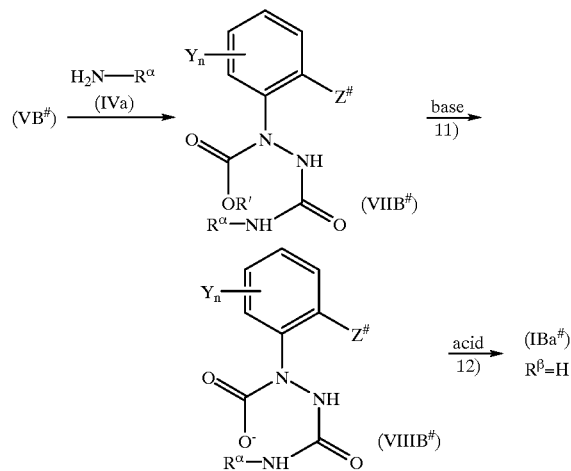

11–12) The cyclization of $VB^{\#}$ via intermediates $VIIB^{\#}$ and $VIIIB^{\#}$ is carried out under the conditions described in sections 3) and 4) for the cyclization of the dicarbonyl compounds $IIIA^{\#}$.

Intermediates of the formula 2,

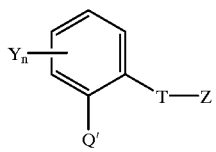

(2)

in which Q' is N(NH$_2$)COOR', N(NHCOCl)COOR' or N(NHCONHR$^\alpha$)COOR', where Y, n, T, Z and R$^\alpha$ are as defined in formula I and R' is C$_1$–C$_4$-alkyl, are novel.

Compounds of the formula IBa$^\#$, in which R$^\beta$ is not hydrogen, are preferably obtained from the corresponding compounds IBa$^\#$ where R$^\beta$=hydrogen by alkylation.

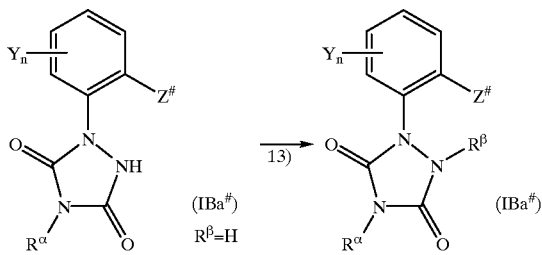

13) The alkylation of the triazolidinediones IBa$^\#$ is carried out under customary conditions, if required in the presence of a base [cf. Synth. Commun., 18 (1988), 2011; J. Chem. Soc. Chem. Commun., (1987), p. 735].

Suitable alkylating agents are, for example, alkyl halides, alkyl sulfonates, alkyl p-toluenesulfonates, alkyl trifluoromethanesulfonates, alcohols, ethers or alkyl p-bromophenylsulfonates or the corresponding benzyl compounds, in particular methyl iodide or dimethyl sulfate.

The educts are generally reacted with one another in equimolar amounts. In terms of yield, it may be advantageous to employ an excess of alkylating agent, based on IBa$^\#$.

Phenyl compounds of the formula I$'^\#$ are preferably obtained from the compounds of the formula II$'^\#$. In the formula II$'^\#$, L' is a leaving group which is customary for nucleophilic aromatic substitution, such as, for example, fluorine, chlorine, bromine, nitro or alkyl or arylsulfonates, such as mesylate, tolylate or triflate. Fluorine is the preferred leaving group.

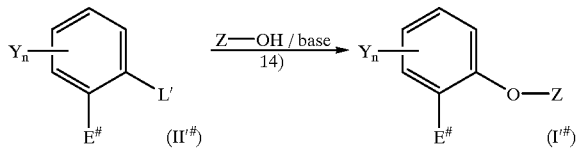

14) This reaction is usually carried out at from –20° C. to 170° C., preferably at from 0° C. to 100° C., in an inert organic solvent in the presence of a base [cf. WO-A 97/24,317; J. Chem. Soc., Perkin Trans., 1 (1989), p. 1727; Chem. Ber., 121 (1988), p. 2035].

Suitable solvents are aromatic hydrocarbons, halogenated hydrocarbons, ethers such as diethyl ether, diisopropyl ether, tert-butyl methyl ether, dioxane, anisole and tetrahydrofuran, nitriles, ketones, and also dimethyl sulfoxide, dimethylformamide and dimethylacetamide, particularly preferably dimethylformamide, dimethyl sulfoxide and tetrahydrofuran. It is also possible to employ mixtures of the abovementioned solvents.

Suitable bases are, in general, inorganic compounds, such as alkali metal and alkaline earth metal hydroxides, alkali metal and alkaline earth metal oxides, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, and also alkali metal bicarbonates such as sodium bicarbonate, organometallic compounds, in particular alkali metal alkyls, alkylmagnesium halides, and also alkali metal and alkaline earth metal alkoxides such as sodium methoxide, sodium ethoxide, potassium ethoxide, potassium tert-butoxide and dimethoxymagnesium, furthermore organic bases, for example tertiary amines, pyridine, substituted pyridines and also bicyclic amines. Particular preference is given to sodium hydride, potassium tert-butoxide and potassium carbonate. The bases are generally employed in equimolar amounts, in excess or, if appropriate, as solvent.

The educts are generally reacted with each other in equimolar amounts. In terms of yield, it may be advantageous to employ an excess of Z—OH, based on II$'^\#$.

Phenyl compounds of the formua I$'^\#$ in which Z is a group x may alternatively be obtained from phenols of the formula IIb$'^\#$. IIb$'^\#$ is reacted with a halide Z-Hal to give I$'^\#$.

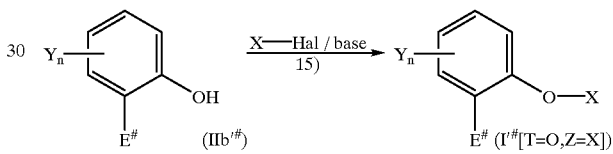

15) This reaction is usually carried out at from –20° C. to 180° C., preferably at from 20° C. to 160° C., in an inert organic solvent in the presence of a base [cf. EP-A 203 608; EP-A 242 081].

Suitable solvents are aromatic hydrocarbons, halogenated hydrocarbons, ethers, nitriles, ketones, and also dimethyl sulfoxide, dimethylformamide and dimethylacetamide, particularly preferably dimethylformamide and dimethyl sulfoxide. It is also possible to employ mixtures of the abovementioned solvents.

Suitable bases are, in general, inorganic compounds, such as alkali metal and alkaline earth metal hydroxides, alkali metal and alkaline earth metal oxides, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, and also alkali metal bicarbonates such as sodium bicarbonate, organometallic compounds, in particular alkali metal alkyls, alkylmagnesium halides, and also alkali metal and alkaline earth metal alkoxides, such as sodium methoxide, sodium ethoxide, potassium ethoxide, potassium tert-butoxide and dimethoxymagnesium, furthermore organic bases, for example tertiary amines, pyridine, substituted pyridine and also bicyclic amines. Particular preference is given to sodium hydride, potassium tert-butoxide and potassium carbonate. The bases are generally employed in equimolar amounts, in excess or, if appropriate, as solvent.

The educts are generally reacted with each other in equimolar amounts. In terms of yield, it may be advantageous to employ an excess of X-Hal, based on IIb$'^\#$.

Phenyl compounds of the formula I'"# are preferably obtained from the benzyl compounds of the formula II'"#. In the formula II'"#, L is a nucleofuge leaving group, such as halogen or alkyl sulfonate or aryl sulfonate, preferably bromine, chlorine, iodine, mesylate, tosylate or triflate, and E# is a group A or B or a precursor thereof.

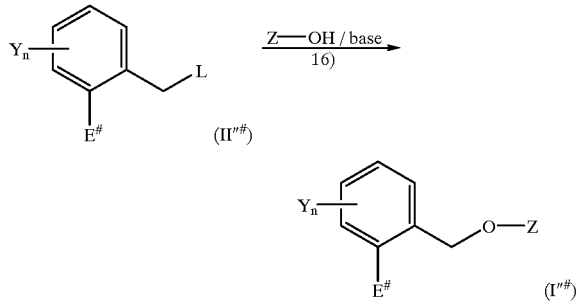

16) This reaction is usually carried out at from 0° C. to 180° C., preferably at from 20° C. to 60° C., in an inert organic solvent in the presence of a base [cf. EP-A 254 426; EP-A 463 488; WO-A 95/18,789; WO-A 95/29, 896].

Suitable solvents are aliphatic hydrocarbons, aromatic hydrocarbons, halogenated hydrocarbons, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols, and also dimethyl sulfoxide, dimethylformamide and dimethylacetamide, particularly preferably dimethylformamide, tetrahydrofuran and acetone. It is also possible to employ mixtures of the abovementioned solvents.

Suitable bases are, in general, inorganic compounds, such as alkali metal and alkaline earth metal hydroxides, alkali metal and alkaline earth metal oxides, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, and also alkali metal bicarbonates such as sodium bicarbonate, organometallic compounds, in particular alkali metal alkyls, alkylmagnesium halides, and also alkali metal and alkaline earth metal alkoxides such as sodium ethoxide, sodium ethoxide, potassium ethoxide, potassium tert-butoxide and dimethoxymagnesium, furthermore organic bases, for example tertiary amines, pyridine, substituted pyridines, and also bicyclic amines. Particular preference is given to sodium hydride, potassium carbonate and sodium methoxide. The bases are generally employed in equimolar amounts, in excess or, if appropriate, as solvent.

The educts are generally reacted with each other in equimolar amounts. In terms of yield, it may be advantageous to employ an excess of Z—OH, based on II'"#.

The starting materials Z—OH required for preparing the compounds I' are known, or they can be prepared in accordance with the literature cited.

17) The benzyl compounds III'"# are obtainable from the corresponding tolyl compounds IIa'"# under customary conditions [cf. J. Amer. Chem. Soc., 71 (1949), p. 2137ff.; ibid 90 (1968), p. 1797ff.].

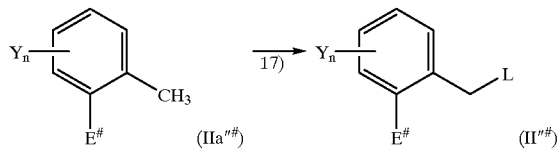

If particular compounds I cannot be obtained by the routes described above, they can be prepared by derivatization of other compounds I.

The reaction mixtures are worked up in a customary manner, for example by mixing with water, phase separation and, if required, chromatographic purification of the crude products. Some intermediates and end products are obtained in the form of colorless or slightly brownish, viscous oils, which are purified or freed from volatile compounds under reduced pressure and at moderately elevated temperature. If the intermediates and end products are obtained as solids, purification can also be carried out by recrystallization or digestion.

Owing to their C=C— and C=N double bonds, the preparation of the compounds I may yield E/Z isomer mixtures which can be separated into the individual compounds in a customary manner, for example by crystallization or chromatography.

However, if the synthesis yields isomer mixtures, a separation is generally not necessarily required since in some cases the individual isomers can be converted into one another during the preparation for use or upon use (for example under the action of light, acids or bases). Similar conversions may also occur after use, for example in the treatment of plants in the treated plant or in the harmful fungus or animal pest to be controlled.

With regard to the —N=C($R^1$)—C($R^2$)=NOR$^3$ double bonds, the trans,trans isomers of the compounds I are generally preferred in terms of their activity (configuration based on the radical T in relation to the C($R^2$)=NOR$^3$ group, or based on the radical OR$^3$ in relation to the T—N=C($R^1$) group).

In the definitions of the symbols given in the above formulae, collective terms were used which generally represent the following substituents:

Halogen: fluorine, chlorine, bromine and iodine;
Alkyl: saturated, straight-chain or branched hydrocarbon radicals having 1 to 4 or 6 carbon atoms, e.g. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;
Haloalkyl: straight-chain or branched alkyl groups having 1 to 10 carbon atoms (as mentioned above), it being possible for some or all of the hydrogen atoms in these groups to be replaced by halogen atoms as mentioned above, e.g. $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2- fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 6 carbon atoms (as mentioned above) and attached to the skeleton via an oxygen atom (—O—);

Haloalkoxy: straight-chain or branched haloalkyl groups having 1 to 6 carbon atoms (as mentioned above) and attached to the skeleton via an oxygen atom (—O—);

Alkenyl: unsaturated, straight-chain or branched hydrocarbon radicals having 2 to 4 or 6 carbon atoms and a double bond in any position, e.g. ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Haloalkenyl: unsaturated, straight-chain or branched hydrocarbon radicals having from 2 to 6 carbon atoms and a double bond in any position (as mentioned above), it being possible for some or all of the hydrogen atoms in these groups to be replaced by halogen atoms as mentioned above, in particular by fluorine, chlorine and bromine;

Alkenyloxy: unsaturated, straight-chain or branched hydrocarbon radicals having 3 to 6 carbon atoms and a double bond in any position which is not adjacent to the heteroatom (as mentioned above) and attached to the skeleton via an oxygen atom (—O—);

Haloalkenyloxy: unsaturated, straight-chain or branched alkenyloxy groups having 3 to 6 carbon atoms (as mentioned above), it being possible for some or all of the hydrogen atoms in these groups to be replaced by halogen atoms as mentioned above, in particular by fluorine, chlorine and bromine;

Alkynyl: straight-chain or branched hydrocarbon groups having 2 to 4 or 6 carbon atoms and a triple bond in any position, e.g. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Haloalkynyl: unsaturated, straight-chain or branched hydrocarbon radicals having 2 to 6 carbon atoms and a triple bond in any position (as mentioned above), it being possible for some or all of the hydrogen atoms in these groups to be replaced by halogen atoms as mentioned above, in particular by fluorine, chlorine and bromine;

Alkynyloxy: unsaturated, straight-chain or branched hydrocarbon radicals having 3 to 6 carbon atoms and a triple bond in any position which is not adjacent to the heteroatom (as mentioned above) and attached to the skeleton via an oxygen atom (—O—);

Haloalkynyloxy: unsaturated, straight-chain or branched alkynyloxy groups having 3 to 6 carbon atoms (as mentioned above), it being possible for some or all of the hydrogen atoms in these groups to be replaced by halogen atoms as mentioned above, in particular by fluorine, chlorine and bromine;

Cycloalkyl: monocyclic, saturated hydrocarbon groups having 3 to 6, 8, 10 or 12 carbon ring members, e.g. $C_3$–$C_8$-cycloalkyl such as cyclopropyl, cyclobutyl, cyclopentyl, cyclohexyl, cycloheptyl and cyclooctyl;

Cycloalkoxy: monocyclic, saturated hydrocarbon groups having 3 to 12 carbon ring members (as mentioned above) and attached to the skeleton via an oxygen atom (—O—);

Saturated or partially unsaturated cyclic radical which, in addition to carbon atoms, may contain heteroatoms from the group oxygen, sulfur or nitrogen as ring members: cycloalkyl having 3 to 12 carbon ring members as mentioned above or 5- or 6-membered heterocycles (heterocyclyl) containing, in addition to carbon ring members, one to three nitrogen atoms and/or one oxygen or sulfur atom or one or two oxygen and/or sulfur atoms, e.g. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5- dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-triazin-2-yl and 1,2,4-tetrahydrotriazin-3-yl;

Aryl: a mono- to trinuclear aromatic ring system containing 6 to 14 carbon ring members, e.g. phenyl, naphthyl and anthracenyl;

Aryloxy: a mono- to trinuclear aromatic ring system (as mentioned above) which is attached to the skeleton via an oxygen atom (—O—);

Arylthio: a mono- to trinuclear aromatic ring system (as mentioned above) which is attached to the skeleton via a sulfur atom (—S—);

Arylamino: a mono- to trinuclear aromatic ring system (as mentioned above) which is attached to the skeleton via an amino group (—NH—);

Hetaryl: aromatic ring system which may, in addition to carbon ring members, contain heteroatoms from the group oxygen, sulfur and nitrogen: aryl as mentioned above or mono- or dinuclear heteroaryl, e.g.

5-membered heteroaryl, containing one to four nitrogen atoms or one to three nitrogen atoms and one sulfur or oxygen atom: 5-membered ring heteroaryl groups which may, in addition to carbon atoms, contain one to four nitrogen atoms or one to three nitrogen atoms and one sulfur or oxygen atom as ring members, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered heteroaryl, containing one to three nitrogen atoms or one nitrogen atom and one oxygen or sulfur atom: 5-membered ring heteroaryl groups which may, in addition to carbon atoms, contain one to four nitrogen atoms or one to three nitrogen atoms and one sulfur or oxygen atom as ring members, and in which two neighboring carbon ring members or one nitrogen and one neighboring carbon ring member may be bridged by a buta-1,3-diene-1,4-diyl group;

5-membered heteroaryl which is attached via nitrogen and contains one to four nitrogen atoms, or benzo-fused 5-membered heteroaryl which is attached via nitrogen and contains one to three nitrogen atoms: 5-membered ring heteroaryl groups which may, in addition to carbon atoms, contain one to four nitrogen atoms or one to three nitrogen atoms as ring members, and in which two neighboring carbon ring members or one nitrogen and one neighboring carbon ring member may be bridged by a buta-1,3-diene-1,4-diyl group, these rings being attached to the skeleton via one of the nitrogen ring members;

6-membered heteroaryl, containing one to three or one to four nitrogen atoms: 6-membered ring heteroaryl groups which may, in addition to carbon atoms, contain one to three or one to four nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

With respect to alkyl, alkenyl and alkynyl groups, the term "with or without substitution" is intended to express that these groups may be partially or fully halogenated [i.e. the halogen atoms of these groups may be partly or wholly replaced by identical or different halogen atoms as mentioned above (preferably fluorine, chlorine or bromine)] and/or carry one to three (preferably one) of the following radicals:

cyano, nitro, hydroxyl, alkoxy, haloalkoxy, alkoxycarbonyl, alkylcarbonyloxy, where the alkyl groups in these radicals preferably contain 1 to 6 carbon atoms, in particular 1 to 4 carbon atoms;

cycloalkyl, cycloalkoxy, heterocyclyl, heterocyclyloxy, without substitution or with substitution by customary groups, where the cyclic systems contain 3 to 12 ring members, preferably 2 to 8 ring members in particular 3 to 6 ring members and the alkyl groups in these radicals preferably contain 1 to 6 carbon atoms, in particular 1 to 4 carbon atoms;

aryl, aryloxy, arylalkoxy, arylalkyl, hetaryl, hetaryloxy, hetarylthio, hetarylamino, hetarylalkoxy, hetarylalkyl, without substitution or with substitution by customary groups, where the alkyl radicals preferably contain 6 to 10 ring members, in particular 6 ring members (phenyl), the hetaryl radicals contain in particular 5 or 6 ring members and the alkyl groups in these radicals preferably contain 1 to 6 carbon atoms, in particular 1 to 4 carbon atoms.

With respect to the cyclic (saturated, unsaturated or aromatic) groups, the term "with or without substitution" is intended to express that these groups may be partially or fully halogenated [i.e. the hydrogen atoms of these groups may be partly or wholly replaced by identical or different halogen atoms as mentioned above (preferably fluorine, chlorine or bromine, in particular fluorine or chlorine)] and/or carry one to four (in particular one to three) of the following radicals:

cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals preferably contain 1 to 6 carbon atoms, in particular 1 to 4 carbon atoms, and the abovementioned alkenyl or alkynyl groups in these radicals contain 2 to 8, preferably 2 to 6, in particular 2 to 4 carbon atoms;

and/or one to three (in particular one) of the following radicals:

cycloalkyl, cycloalkoxy, heterocyclyl, heterocyclyloxy, with or without substitution, where the cyclic systems contain 3 to 12 ring members, preferably 2 to 8 ring members, in particular 3 to 6 ring members and the alkyl groups in these radicals preferably contain 1 to 6 carbon atoms, in particular 1 to 4 carbon atoms;

aryl, aryloxy, arylthio, arylalkoxy, arylalkyl, hetaryl, hetaryloxy, hetarylthio, with or without substitution, where the aryl radicals preferably contain 6 to 10 ring members, in particular 6 ring members (phenyl), the hetaryl radicals contain in particular 5 or 6 ring members and the alkyl groups in these radicals preferably contain 1 to 6 carbon atoms, in particular 1 to 4 carbon atoms, where the abovementioned cyclic groups for their part may be partially or fully halogenated and/or may carry 1 to 3 of the following substituents:

cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy, which may be halogenated, and/or may carry one or two (in particular one) of the following radicals:

$C(=NOR^d)$—$\Gamma_1$—$R^{d_1}$, where $R^d$ is hydrogen or $C_1$–$C_6$-alkyl, $\Gamma$ is oxygen, sulfur or $NR^d$ and 1 is 0 or 1;

and/or where two neighboring carbon atoms of the cyclic systems may carry an oxy-$C_1$–$C_3$-alkylenoxy, oxy-$C_2$–$C_4$-alkenylene, or butadienediyl group, where these groups for their part may be partially or fully halogenated.

Customary groups are in particular the following substituents: cyano, halogen, nitro, hydroxyl, $C_1$–$C_4$-alkyl, $C_1$–$C_4$-haloalkyl, $C_1$–$C_4$-alkoxy and $C_1$–$C_4$-haloalkoxy.

With respect to the intended use of the phenyl compounds of the formula I, the following meanings of the substituents are particularly preferred, in each case either alone or in combination:

Particular preference is given to compounds of the formula I in which T is oxymethylene.

Additionally, particular preference is given to compounds of the formula I in which n=zero (0).

Likewise, particular preference is given to compounds I in which Z is $N=C(R^1)$—$C(R^2)=NOR^3$.

Additionally, particular preference is given to compounds I in which Z is $N=CWR^1$.

Furthermore, particular preference is given to compounds I in which W is phenyl with or without substitution.

Particular preference is also given to compounds I in which Z is a group X.

Furthermore, particular preference is given to compounds I in which $R^2$ is a group W.

Likewise, particular preference is given to compounds I in which $R^2$ is a group W which is attached via oxygen.

Additionally, particular preference is given to compounds I in which X is aryl with or without substitution or hetaryl with or without substitution.

Furthermore, particular preference is given to compounds I in which $R^1$ is methyl or ethyl.

Moreover, particular preference is given to compounds I in which $R^3$ is $C_1$–$C_3$-alkyl, $C_3$–$C_5$-alkenyl or $C_3$–$C_5$-alkynyl.

Additionally, particular preference is given to compounds I in which $R^3$ is methyl, allyl or propargyl.

Furthermore, particular preference is given to compounds of the formula I, in which T is oxygen or oxymethylene, Z is a group X, $N=CWR^1$ or $N=C(R^1)$—$C(R^2)=NOR^3$, where X is heterocyclyl which may be fully or partially halogenated and/or may carry 1 to 3 of the following radicals:

cyano, $C_1$–$C_4$-alkyl, $C_1$–$C_4$-haloalkyl or $C_1$–$C_4$-alkoxy;

aryl, hetaryl, arylmethylene or hetarylmethylene, where the cyclic radicals may be partially or fully halogenated and/or may carry one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, heteroaryl, heteroaryloxy, heteroarylthio, $C_3$–$C_6$-alkynyloxy, $C_1$–$C_4$-alkylenedioxy which may be halogenated, or $C(=NOR^d)$—$\Gamma_1$—$R^{d_1}$, where $R^d$ is hydrogen or $C_1$–$C_6$-alkyl;

$\Gamma$ is oxygen, sulfur or $NR^d$;

1 is 0 or 1 and the cyclic groups may for their part be partially or fully halogenated and/or may carry 1 to 3 of the following substituents: cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy which may be halogenated, W is $C_1$–$C_6$-alkyl, $C_2$–$C_6$-alkenyl or $C_2$–$C_6$-alkynyl, where these groups may be fully or partially halogenated and/or may carry 1 to 3 of the following radicals:

cyano, $C_1$–$C_6$-alkoxy, $C_1$–$C_6$-haloalkoxy, $C_1$–$C_6$-alkoxycarbonyl, $C_3$–$C_6$-cycloalkyl, heterocyclyl, aryl or hetaryl, where the cyclic groups may for their part be partially or fully halogenated and/or may carry 1 to 3 of the following radicals:

cyano, nitro, $C_1$–$C_4$-alkyl, $C_1$–$C_4$-haloalkyl, $C_1$–$C_4$-alkoxy, $C_1$–$C_4$-haloalkoxy; or is $C_3$–$C_6$-cycloalkyl, $C_3$–$C_6$-cycloalkenyl or heterocyclyl, where these groups may be fully or partially halogenated and/or may carry 1 to 3 of the following radicals:

cyano, $C_1$–$C_4$-alkyl, $C_1$–$C_4$-haloalkyl or $C_1$–$C_4$-alkoxy; or is aryl or heteroaryl, where these radicals may be partially or fully halogenated and/or may carry one to three of the following groups:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, heteroaryl, heteroaryloxy, heteroarylthio, $C_3$–$C_6$-alkynyloxy, $C_1$–$C_4$-alkylenedioxy which may be halogenated, or $C(=NOR^d)$—$\Gamma_1$—$R^{d_1}$, where $R^d$ is hydrogen or $C_1$–$C_6$-alkyl;

$\Gamma$ is oxygen, sulfur or $NR^d$;

1 is 0 or 1 and the cyclic groups may for their part be partially or fully halogenated and/or may carry 1 to 3 of the following substituents:

cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy which may be halogenated;

$R^2$ is hydrogen, cyano, halogen, $C(R^d)=NOR^3$ or W, OW, SW or NRCW, where $R^c$ is hydrogen, $C_1$–$C_6$-alkyl, $C_2$–$C_6$-alkenyl or $C_2$–$C_6$-alkynyl;

$R^d$ is hydrogen or $C_1$–$C_4$-alkyl; and $R^3$ hydrogen, $C_1$–$C_6$-alkyl, $C_1$–$C_6$-cyanoalkyl, $C_2$–$C_6$-alkenyl, $C_2$–$C_6$-alkynyl, $C_1$–$C_4$-alkoxy-$C_1$–$C_6$-alkyl or $C_3$–$C_6$-cycloalkyl–$C_1$–$C_4$-alkyl, where these groups may be partially or fully halogenated and the cycloalkyl groups may additionally carry 1 to 3 $C_1$–$C_4$-alkyl radicals.

With respect to the variables, the particularly preferred embodiments of the intermediates correspond to those of the radicals T, Z, W, $R^\alpha$, $R^\beta$, $Y_n$, $R^1$, $R^2$ and $R^3$ of formula I.

Additionally, particular preference is given to compounds of the formula IA in which $R^\alpha$ is $C_1$–$C_4$-alkyl or $C_1$–$C_4$-haloalkyl.

Particular preference is given to compounds IA in which $R^\alpha$ is methyl.

Likewise, particular preference is given to compounds IA in which $R^\alpha$ is trifluoromethyl.

Particular preference is given to compounds IA.1' in which $R^\alpha$ is methyl, ethyl, trifluoromethyl or cyclopropyl and Z is phenyl, pyridinyl, pyrimidinyl, quinazolinyl, furanyl, thienyl, pyrrolyl, benzofuranyl, benzothiophenyl, indolyl, pyrazolyl, isoxazolyl, isothiazolyl, oxazolyl, thiazolyl, imidazolyl, triazolyl, tetrazolyl, thiadiazolyl, benzoxazolyl, benzisoxazolyl, benzothiazolyl, benzisothiazolyl or indazolyl, with or without substitution.

(IA.1')

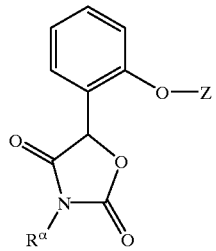

Additionally, particular preference is given to compounds IA.1' in which Z is phenyl which is substituted by halogen, methyl, trifluoromethyl or methoxy.

Additionally, preference is given to compounds IA.1" n which $R^\alpha$ is methyl, ethyl, trifluoromethyl or cyclopropyl and Z is phenyl, naphthyl, pyridinyl, pyrimidinyl, quinolyl, triazolyl, pyrazinyl, thienyl, quinoxalinyl, benzoxazolyl, benzothiazolyl or pyrazolyl, with or without substitution.

(IA.1")

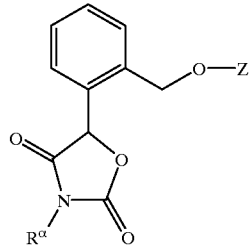

Furthermore, particular preference is given to compounds IA.1" in which Z is phenyl which is substituted by halogen, methyl, trifluoromethyl or $C(=NOR^d)R^{d_1}$.

Likewise, preference is given to compounds IA.2' in which $R^\alpha$ is methyl, ethyl, trifluoromethyl or cyclopropyl and Z is phenyl, naphthyl, pyridinyl, pyrimidinyl, quinolyl, pyrazinyl, thienyl, quinoxalinyl, benzoxazolyl, benzothiazolyl or pyrazolyl, with or without substitution.

(IA.2')

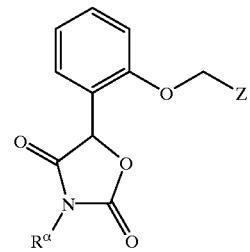

Additionally, particular preference is given to compounds IA.2' in which Z is phenyl which is substituted by halogen, methyl, trifluoromethyl or $C(=NOR^d)R^{d_1}$.

Likewise, particular preference is given to compounds IA.3' in which $R^\alpha$ is methyl, ethyl, trifluoromethyl or cyclopropyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl and $R^1$ is methyl or methoxy.

(IA.3')

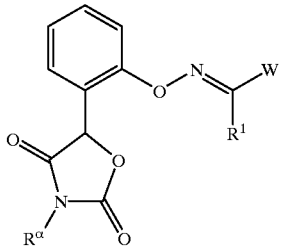

Additionally, preference is given to compounds IA.3" in which $R^\alpha$ is methyl, ethyl, trifluoromethyl or cyclopropyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl and $R^1$ is methyl or methoxy.

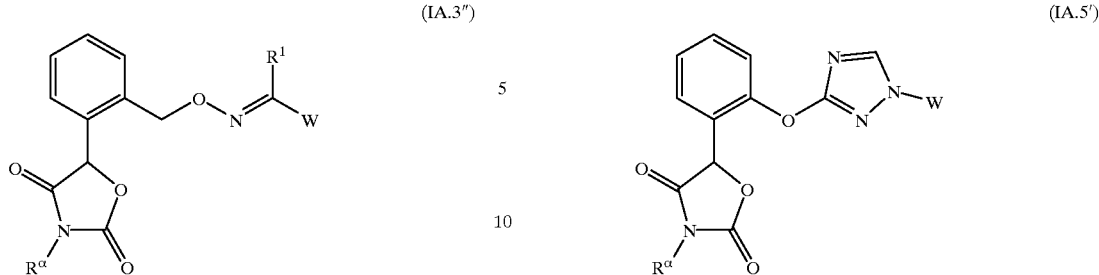

(IA.3″)

(IA.5′)

Furthermore, preference is given to compounds IA.4′ in which $R^\alpha$ is methyl, ethyl, trifluoromethyl or cyclopropyl, $R^1$ is methyl or methoxy, $R^2$ is halogen, cyano, $C(=NOR^{d'})R^{d'}$, is $C_1$–$C_4$-alkyl, $C_1$–$C_4$-cycloalkyl, $C_1$–$C_4$-haloalkyl, $C_1$–$C_4$-alkoxy, $C_1$–$C_4$-alkylthio, $C_1$–$C_4$-cycloalkoxy, $C_1$–$C_4$-alkylamino, $C_2$–$C_4$-alkenyl or phenyl, with or without substitution, and $R^3$ is hydrogen, propargyl or allyl or $C_1$–$C_4$-alkyl with or without substitution.

Particular preference is given to compounds IA.5″ in which $R^\alpha$ is methyl, ethyl, trifluoromethyl or cyclopropyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

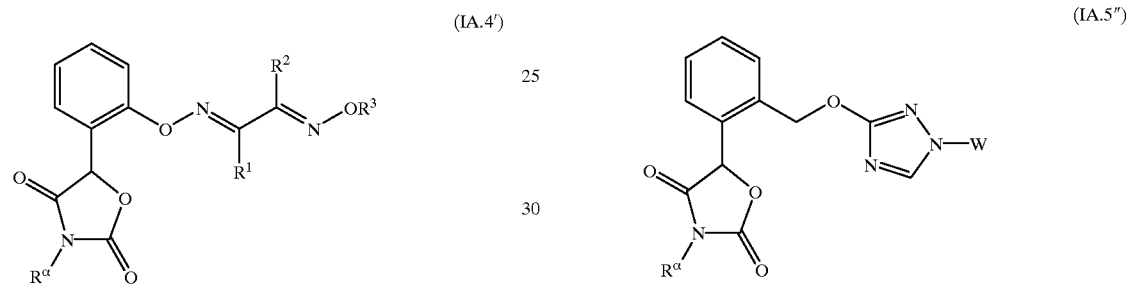

(IA.4′)

(IA.5″)

Moreover, preference is given to compounds IA.4″ in which, $R^\alpha$ is methyl, ethyl, trifluoromethyl or cyclopropyl, $R^1$ is methyl or methoxy, $R^2$ is halogen, cyano, $C(=NOR^{d'})R^{d'}$, is $C_1$–$C_4$-alkyl, $C_1$–$C_4$-cycloalkyl, $C_1$–$C_4$-haloalkyl, $C_1$–$C_4$-alkoxy, $C_1$–$C_4$-alkylthio, $C_1$–$C_4$-cycloalkoxy, $C_1$–$C_4$-alkylamino, $C_2$–$C_4$-alkenyl or phenyl, with or without substitution, and $R^3$ is hydrogen, propargyl or allyl or $C_1$–$C_4$-alkyl with or without substitution.

Moreover, preference is given to compounds IA.6′ in which $R^\alpha$ is methyl, ethyl, trifluoromethyl or cyclopropyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

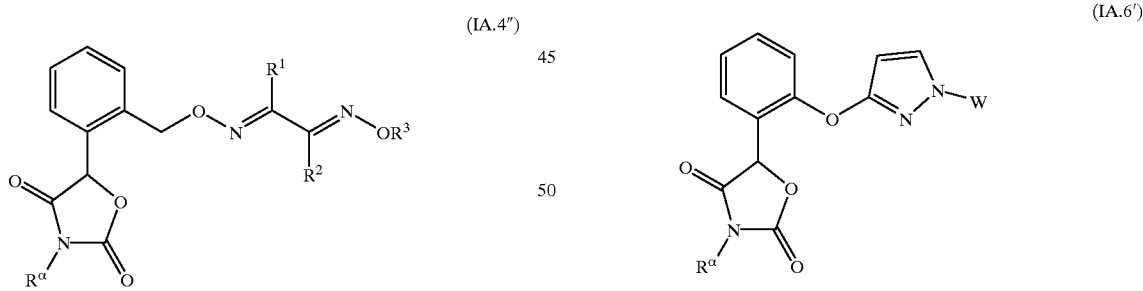

(IA.4″)

(IA.6′)

Furthermore, preference is given to compounds IA.5′ in which $R^\alpha$ is methyl, ethyl, trifluoromethyl or cyclopropyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

Likewise, preference is given to compounds IA.6″, in which $R^\alpha$ is methyl, ethyl, trifluoromethyl or cyclopropyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

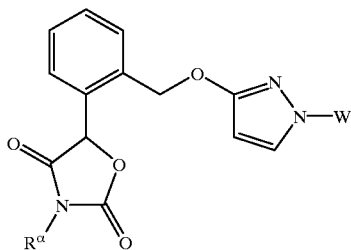

(IA.6″)

Additionally, preference is given to compounds IA.7′ in which $R^\alpha$ is methyl, ethyl, trifluoromethyl or cyclopropyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

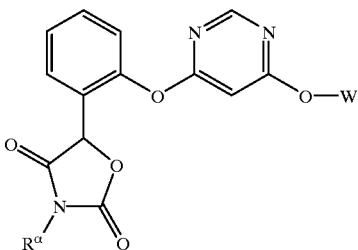

(IA.7′)

Moreover, preference is also given to compounds IA.8′ in which $R^\alpha$ is methyl, ethyl, trifluoromethyl or cyclopropyl, T is nitrogen or carbon and W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

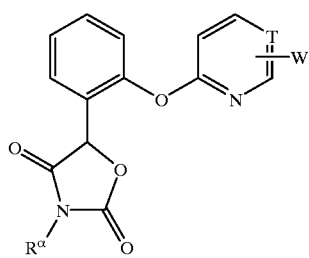

(IA.8′)

Particular preference is given to compounds IB in which $R^\alpha$ is methyl, ethyl, trifluoromethyl or cyclopropyl.

Additionally, preference is given to compounds IB in which $R^\alpha$ is hydrogen, methyl, ethyl, trifluoromethyl or cyclopropyl.

Furthermore, particular preference is given to compounds IB in which $R^\alpha$ is benzyl.

Likewise, particular preference is given to compounds IB, in which n is zero and $R^\alpha$ and $R^\beta$ are $C_1$–$C_4$-alkyl.

Particular preference is given to compounds IB.1′ in which $R^\alpha$ is methyl, ethyl, trifluoromethyl or cyclopropyl, $R^\beta$ is hydrogen, methyl, ethyl, trifluoromethyl, cyclopropyl or benzyl and Z is phenyl, pyridinyl, pyrimidinyl, quinazolinyl, furanyl, thienyl, pyrrolyl, benzofuranyl, benzothiophenyl, indolyl, pyrazolyl, isoxazolyl, isothiazolyl, oxazolyl, thiazolyl, imidazolyl, triazolyl, tetrazolyl, thiadiazolyl, benzoxazolyl, benzisoxazolyl, benzothiazolyl, benzisothiazolyl or indazolyl, with or without substitution.

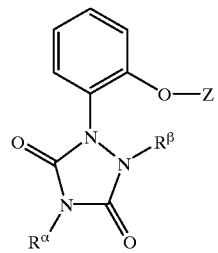

(IB.1′)

Additionally, particular preference is given to compounds IB.1′ in which Z is phenyl which is substituted by halogen, methyl, trifluoromethyl or methoxy.

Moreover, preference is given to compounds IB.1″ in which $R^\alpha$ is methyl, ethyl, trifluoromethyl or cyclopropyl, $R^\alpha$ is hydrogen, methyl, ethyl, trifluoromethyl, cyclopropyl or benzyl and Z is phenyl, naphthyl, pyridinyl, pyrimidinyl, quinolyl, triazolyl, pyrazinyl, thienyl, quinoxalinyl, benzoxazolyl, benzothiazolyl or pyrazolyl, with or without substitution.

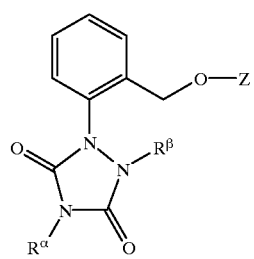

(IB.1″)

Furthermore, particular preference is given to compounds IB.1″ in which Z is phenyl which is substituted by halogen, methyl, trifluoromethyl or $C(=NOR^d)R^{d'}$.

Likewise, preference is given to compounds IB.2′ in which $R^\alpha$ is methyl ethyl, trifluoromethyl or cyclopropyl, $R^\beta$ is hydrogen, methyl, ethyl, trifluoromethyl, cyclopropyl or benzyl and Z is phenyl, naphthyl, pyridinyl, pyrimidinyl, quinolyl, pyrazinyl, thienyl, quinoxalinyl, benzoxazolyl, benzothiazolyl or pyrazolyl with or without substitution.

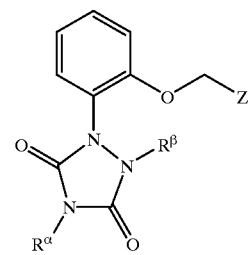

(IB.2′)

Additionally, particular preference is given to compounds IB.2′ in which Z is phenyl which is substituted by halogen, methyl, trifluoromethyl or $C(=NOR^d)R^{d'}$.

Likewise, particular preference is given to compouns IB.3′, in which $R^\alpha$ is methyl, ethyl, trifluoromethyl or cyclopropyl, $R^\beta$ is hydrogen, methyl, ethyl, trifluoromethyl, cyclopropyl or benzyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl and $R^1$ is methyl or methoxy.

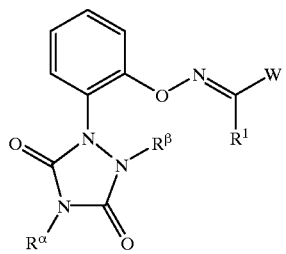

(IB.3')

Additionally, preference is given to compounds IB.3" in which $R^\alpha$ is methyl, ethyl, trifluoromethyl or cyclopropyl, $R^\beta$ is hydrogen, methyl, ethyl, trifluoromethyl, cyclopropyl or benzyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl and $R^1$ is methyl or methoxy.

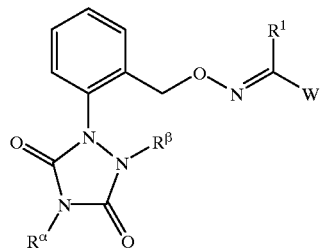

(IB.3")

Furthermore, preference is given to compounds IB.4' in which $R^\alpha$ is methyl, ethyl, trifluoromethyl or cyclopropyl, $R^\beta$ is hydrogen, methyl, ethyl, trifluoromethyl, cyclopropyl or benzyl, $R^1$ is methyl or methoxy, $R^2$ is halogen, cyano, $C(=NOR^{d'})R^{d'}$, is $C_1$–$C_4$-alkyl, $C_1$–$C_4$-cycloalkyl, $C_1$–$C_4$-haloalkyl, $C_1$–$C_4$-alkoxy, $C_1$–$C_4$-alkylthio, $C_1$–$C_4$-cycloalkoxy, $C_1$–$C_4$-alkylamino, $C_2$–$C_4$-alkenyl or phenyl, with or without substitution, and $R^3$ is hydrogen, propargyl or allyl or $C_1$–$C_4$-alkyl with or without substitution.

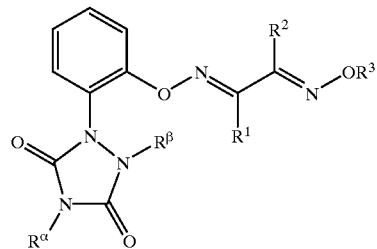

(IB.4')

Moreover, preference is given to compounds IB.4", in which $R^\alpha$ is methyl, ethyl, trifluoromethyl or cyclopropyl, $R^\beta$ is hydrogen, methyl, ethyl, trifluoromethyl, cyclopropyl or benzyl, $R^1$ is methyl or methoxy, $R^2$ is halogen, cyano, $C(=NOR^{d'})R^{d'}$, is $C_1$–$C_4$-alkyl, $C_1$–$C_4$-cycloalkyl, $C_1$–$C_4$-haloalkyl, $C_1$–$C_4$-alkoxy, $C_1$–$C_4$-alkylthio, $C_1$–$C_4$-cycloalkoxy, $C_1$–$C_4$-alkylamino, $C_2$–$C_4$-alkenyl or phenyl, with or without substitution, and $R^3$ is hydrogen, propargyl or allyl or $C_1$–$C_4$-alkyl with or without substitution.

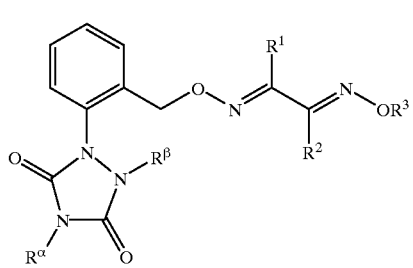

(IB.4")

Furthermore, preference is given to compounds IB.5' in which $R^\alpha$ is methyl, ethyl, trifluoromethyl or cyclopropyl, $R^\beta$ is hydrogen, methyl, ethyl, trifluoromethyl, cyclopropyl or benzyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

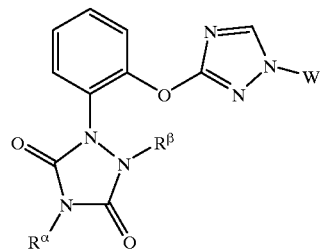

(IB.5')

Particular preference is given to compounds IB.5" in which, $R^\alpha$ is methyl, ethyl, trifluoromethyl or cyclopropyl, $R^\beta$ is hydrogen, methyl, ethyl, trifluoromethyl, cyclopropyl or benzyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

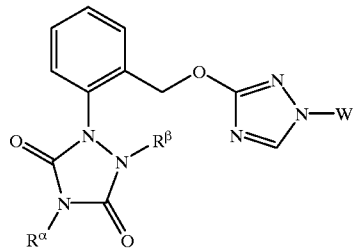

(IB.5")

Moreover, preference is given to compounds IB.6' in which $R^\alpha$ is methyl, ethyl, trifluoromethyl or cyclopropyl, $R^\beta$ is hydrogen, methyl, ethyl, trifluoromethyl, cyclopropyl or benzyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

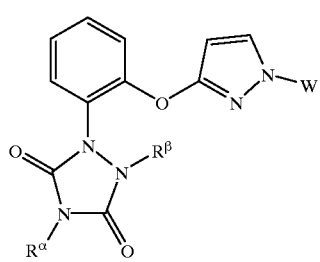

(IB.6')

Likewise, preference is given to compounds IB.6", in which $R^\alpha$ is methyl, ethyl, trifluoromethyl or cyclopropyl, $R^\beta$ is hydrogen, methyl, ethyl, trifluoromethyl, cyclopropyl or benzyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

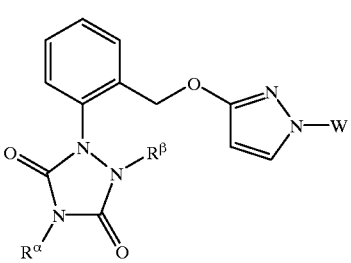

(IB.6")

Additionally, preference is given to compounds IB.7' in which $R^\alpha$ is methyl, ethyl, trifluoromethyl or cyclopropyl, $R^\beta$ is hydrogen, methyl, ethyl, trifluoromethyl, cyclopropyl or benzyl, W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

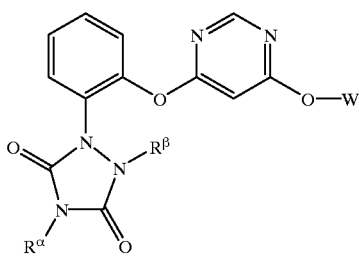

(IB.7')

Moreover, preference is also given to compounds IB.8' in which $R^\alpha$ is methyl, ethyl, trifluoromethyl or cyclopropyl, $R^\beta$ is hydrogen, methyl, ethyl, trifluoromethyl, cyclopropyl or benzyl, T is nitrogen or carbon and W is phenyl, naphthyl, anthryl, benzyl, phenylethyl, phenylpropyl, pyridinyl, pyrimidinyl, thienyl, furyl, thiazolyl, benzothiazolyl, dioxanyl, $C_3$–$C_6$-cycloalkyl, with or without substitution, and also $C_1$–$C_4$-alkyl, allyl, propargyl or trifluoromethyl.

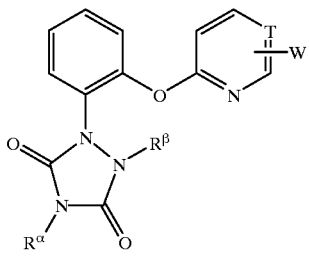

(IB.8')

With respect to their use, particular preference is given to the compounds I which are listed in the tables that follow. The groups mentioned in the tables for a substituent additionally represent, on their own and in independently of the combination in which they are mentioned, a particularly preferred embodiment of the respective substituent.

Table 1
Compounds of the formula IA.1', in which $R^\alpha$ is methyl and for each compound Z corresponds to one row of Table A Table 2
Compounds of the formula IA.1", in which $R^\alpha$ is methyl and for each compound Z corresponds to one row of Table B Table 3
Compounds of the formula IA.2', in which $R^\alpha$ is methyl and for each compound Z corresponds to one row of Table B Table 4
Compounds of the formula IA.3', in which $R^\alpha$ is methyl, $R^1$ is methyl and for each compound W corresponds to one row of Table C Table 5
Compounds of the formula IA.3", in which $R^\alpha$ is methyl, $R^1$ is methyl and for each compound W corresponds to one row of Table C Table 6
Compounds of the formula IA.4', in which $R^\alpha$ is methyl, $R^1$ is methyl and for each compound the combination of the radicals $R^2$ and $R^3$ corresponds to one row of Table D Table 7
Compounds of the formula IA.4', in which $R^\alpha$ is methyl, $R^1$ is methoxy and for each compound the combination of the radicals $R^2$ and $R^3$ corresponds to one row of Table D Table 8
Compounds of the formula IA.4", in which $R^\alpha$ is methyl, $R^1$ is methyl and for each compound the combination of the radicals $R^2$ and $R^3$ corresponds to one row of Table D Table 9
Compounds of the formula IA.4", in which $R^\alpha$ is methyl, $R^1$ is methoxy and for each compound the combination of the radicals $R^2$ and $R^3$ corresponds to one row of Table D Table 10
Compounds of the formula IA.5", in which $R^\alpha$ is methyl and for each compound W corresponds to one row of Table C Table 11
Compounds of the formula IA.6', in which $R^\alpha$ is methyl and for each compound W corresponds to one row of Table C Table 12
Compounds of the formula IA.6", in which $R^\alpha$ is methyl and for each compound W corresponds to one row of Table C Table 13
Compounds of the formula IA.7', in which $R^\alpha$ is methyl and for each compound W corresponds to one row of Table C Table 14
Compounds of the formula IA.1', in which $R^\alpha$ is ethyl and for each compound Z corresponds to one row of Table A Table 15
Compounds of the formula IA.1", in which $R^\alpha$ is ethyl and for each compound Z corresponds to one row of Table B Table 16
Compounds of the formula IA.2', in which $R^\alpha$ is ethyl and for each compound Z corresponds to one row of Table B Table 17
Compounds of the formula IA.3', in which $R^\alpha$ is ethyl, $R^1$ is methyl and for each compound W corresponds to one row of Table C Table 18
Compounds of the formula IA.3", in which $R^\alpha$ is ethyl, $R^1$ is methyl and for each compound W corresponds to one row of Table C Table 19
Compounds of the formula IA.4', in which $R^\alpha$ is ethyl, $R^1$ is methyl and for each compound the combination of the radicals $R^2$ and $R^3$ corresponds to one row of Table D Table 20
Compounds of the formula IA.4', in which $R^\alpha$ is ethyl, $R^1$ is methoxy and for each compound the combination of the radicals $R^2$ and $R^3$ corresponds to one row of Table D Table 21
Compounds of the formula IA.4", in which $R^\alpha$ is ethyl, $R^1$ is methyl and for each compound the combination of the radicals $R^2$ and $R^3$ corresponds to one row of Table D Table 22
Compounds of the formula IA.4", in which $R^\alpha$ is ethyl, $R^1$ is methoxy and for each compound the combination of the radicals $R^2$ and $R^3$ corresponds to one row of Table D Table 23
Compounds of the formula IA.5", in which $R^\alpha$ is ethyl and for each compound W corresponds to one row of Table C Table 24
Compounds of the formula IA.6', in which $R^\alpha$ is ethyl and for each compound W corresponds to one row of Table C Table 25
Compounds of the formula IA.6", in which $R^\alpha$ is ethyl and for each compound W corresponds to one row of Table C Table 26
Compounds of the formula IA.7', in which $R^\alpha$ is ethyl and for each compound W corresponds to one row of Table C Table 27
Compounds of the formula IA.1', in which $R^\alpha$ is trifluoromethyl and for each compound Z corresponds to one row of Table A Table 28
Compounds of the formula IA.1", in which $R^\alpha$ is trifluoromethyl and for each compound Z corresponds to one row of Table B Table 29
Compounds of the formula IA.2', in which $R^\alpha$ is trifluoromethyl and for each compound Z corresponds to one row of Table B Table 30
Compounds of the formula IA.3', in which $R^\alpha$ is trifluoromethyl, $R^1$ is methyl and for each compound W corresponds to one row of Table C Table 31
Compounds of the formula IA.3", in which $R^\alpha$ is trifluoromethyl, $R^1$ is methyl and for each compound W corresponds to one row of Table C Table 32
Compounds of the formula IA.4', in which $R^\alpha$ is trifluoromethyl, $R^1$ is methyl and for each compound the combination of the radicals $R^2$ and $R^3$ corresponds to one row of Table D Table 33
Compounds of the formula IA.4", in which $R^\alpha$ is trifluoromethyl, $R^1$ is methoxy and for each compound the combination of the radicals $R^2$ and $R^3$ corresponds to one row of Table D Table 34
Compounds of the formula IA.4", in which $R^\alpha$ is trifluoromethyl, $R^1$ is methyl and for each compound the combination of the radicals $R^2$ and $R^3$ corresponds to one row of Table D Table 35
Compounds of the formula IA.4", in which $R^\alpha$ is trifluoromethyl, $R^1$ is methoxy and for each compound the combination of the radicals $R^2$ and $R^3$ corresponds to one row of Table D Table 36
Compounds of the formula IA.5", in which $R^\alpha$ is trifluoromethyl and for each compound W corresponds to one row of Table C Table 37
Compounds of the formula IA.6', in which $R^\alpha$ is trifluoromethyl and for each compound W corresponds to one row of Table C Table 38
Compounds of the formula IA.6", in which $R^\alpha$ is trifluoromethyl and for each compound W corresponds to one row of Table C Table 39
Compounds of the formula IA.7', in which $R^\alpha$ is trifluoromethyl and for each compound W corresponds to one row of Table C Table 40
Compounds of the formula IA.1', in which $R^\alpha$ is cyclopropyl and for each compound Z corresponds to one row of Table A Table 41
Compounds of the formula IA.1", in which $R^\alpha$ is cyclopropyl and for each compound Z corresponds to one row of Table B Table 42
Compounds of the formula IA.2', in which $R^\alpha$ is cyclopropyl and for each compound Z corresponds to one row of Table B Table 43
Compounds of the formula IA.3', in which $R^\alpha$ is cyclopropyl, $R^1$ is methyl and for each compound W corresponds to one row of Table C Table 44
Compounds of the formula IA.3", in which $R^\alpha$ is cyclopropyl, $R^1$ is methyl and for each compound W corresponds to one row of Table C Table 45
Compounds of the formula IA.4', in which $R^\alpha$ is cyclopropyl, $R^1$ is methyl and for each compound the combination of the radicals $R^2$ and $R^3$ corresponds to one row of Table D Table 46
Compounds of the formula IA.4', in which $R^\alpha$ is cyclopropyl, $R^1$ is methoxy and for each compound the combination of the radicals $R^2$ and $R^3$ corresponds to one row of Table D Table 47
Compounds of the formula IA.4", in which $R^\alpha$ is cyclopropyl, $R^1$ is methyl and for each compound the combination of the radicals $R^2$ and $R^3$ corresponds to one row of Table D Table 48
Compounds of the formula IA.4", in which $R^\alpha$ is cyclopropyl, $R^1$ is methoxy and for each compound the combination of the radicals $R^2$ and $R^3$ corresponds to one row of Table D Table 49
Compounds of the formula IA.5", in which $R^\alpha$ is cyclopropyl and for each compound W corresponds to one row of Table C Table 50
Compounds of the formula IA.6', in which $R^\alpha$ is cyclopropyl and for each compound W corresponds to one row of Table C Table 51
Compounds of the formula IA.6", in which $R^\alpha$ is cyclopropyl and for each compound W corresponds to one row of Table C Table 52
Compounds of the formula IA.7', in which $R^\alpha$ is cyclopropyl and for each compound W corresponds to one row of Table C Table 53
Compounds of the formula IB.1', in which $R^\alpha$ is methyl and $R^\beta$ is hydrogen and for each compound Z corresponds to one row of Table A Table 54
Compounds of the formula IB.1", in which $R^\alpha$ is methyl and $R^\beta$ is hydrogen and for each compound Z corresponds to one row of Table B Table 55
Compounds of the formula IB.2', in which $R^\alpha$ is methyl and $R^\beta$ is hydrogen and for each compound Z corresponds to one row of Table B Table 56
Compounds of the formula IB.3', in which $R^\alpha$ is methyl and $R^\beta$ is hydrogen, $R^1$ is methyl and for each compound W corresponds to one row of Table C Table 57
Compounds of the formula IB.3", in which $R^\alpha$ is methyl and $R^\beta$ is hydrogen, $R^1$ is methyl and for each compound W corresponds to one row of Table C Table 58
Compounds of the formula IB.4', in which $R^\alpha$ is methyl and $R^\beta$ is hydrogen and $R^1$ is methyl and for each compound the combination of the radicals $R^2$ and $R^3$ corresponds to one row of Table D Table 59
Compounds of the formula IB.4', in which $R^\alpha$ is methyl and $R^\beta$ is hydrogen, $R^1$ is methoxy and for each compound the combination of the radicals $R^2$ and $R^3$ corresponds to one row of Table D Table 60
Compounds of the formula IB.4", in which $R^\alpha$ is methyl and $R^\beta$ is hydrogen and $R^1$ is methyl and for each compound the combination of the radicals $R^2$ and $R^3$ corresponds to one row of Table D Table 61
Compounds of the formula IB.4", in which $R^\alpha$ is methyl and $R^\beta$ is hydrogen, $R^1$ is methoxy and for each compound the combination of the radicals $R^2$ and $R^3$ corresponds to one row of Table D Table 62
Compounds of the formula IB.5", in which $R^\alpha$ is methyl and $R^\beta$ is hydrogen and for each compound W corresponds to one row of Table C Table 63
Compounds of the formula IB.6', in which $R^\alpha$ is methyl and $R^\beta$ is hydrogen and for each compound W corresponds to one row of Table C Table 64
Compounds of the formula IB.6", in which $R^\alpha$ is methyl and $R^\beta$ is hydrogen and for each compound W corresponds to one row of Table C Table 65
Compounds of the formula IB.7", in which $R^\alpha$ is methyl and $R^\beta$ is hydrogen and for each compound W corresponds to one row of Table B Table 66
Compounds of the formula IB.1', in which $R^\alpha$ and $R^\beta$ are methyl and for each compound Z corresponds to one row of Table A Table 67
Compounds of the formula IB.1", in which $R^\alpha$ and $R^\beta$ are methyl and for each compound Z corresponds to one row of Table B Table 68
Compounds of the formula IB.2', in which $R^\alpha$ and $R^\beta$ are methyl and for each compound Z corresponds to one row of Table B Table 69
Compounds of the formula IB.3', in which $R^\alpha$ and $R^\beta$ are methyl, $R^1$ is methyl and for each compound W corresponds to one row of Table C Table 70
Compounds of the formula IB.3", in which $R^\alpha$ and $R^\beta$ are methyl, $R^1$ is methyl and for each compound W corresponds to one row of Table C Table 71
Compounds of the formula IB.4', in which $R^\alpha$, $R^\beta$ and $R^1$ are methyl and for each compound the combination of the radicals $R^2$ and $R^3$ corresponds to one row of Table D Table 72
Compounds of the formula IB.4", in which $R^\alpha$ and $R^\beta$ are methyl, $R^1$ is methoxy and for each compound the combination of the radicals $R^2$ and $R^3$ corresponds to one row of Table D Table 73
Compounds of the formula IB.4", in which $R^\alpha$, $R^\beta$ and $R^1$ are methyl and for each compound the combination of the radicals $R^2$ and $R^3$ corresponds to one row of Table D Table 74
Compounds of the formula IB.4", in which $R^\alpha$ and $R^\beta$ are methyl, $R^1$ is methoxy and for each compound the combination of the radicals $R^2$ and $R^3$ corresponds to one row of Table D Table 75
Compounds of the formula IB.5", in which $R^\alpha$ and $R^\beta$ are methyl and for each compound W corresponds to one row of Table C Table 76
Compounds of the formula IB.6', in which $R^\alpha$ and $R^\beta$ are methyl and for each compound W corresponds to one row of Table C Table 77
Compounds of the formula IB.6", in which $R^\alpha$ and $R^\beta$ are methyl and for each compound W corresponds to one row of Table C Table 78
Compounds of the formula IB.7', in which $R^\alpha$ and $R^\beta$ are methyl and for each compound W corresponds to one row of Table C Table 79
Compounds of the formula IB.1', in which $R^\alpha$ is methyl, $R^\beta$ is ethyl and for each compound Z corresponds to one row of Table A Table 80
Compounds of the formula IB.1", in which $R^\alpha$ is methyl, $R^\beta$ is ethyl and for each compound Z corresponds to one row of Table B Table 81
Compounds of the formula IB.2', in which $R^\alpha$ is methyl, $R^\beta$ is ethyl and for each compound Z corresponds to one row of Table B Table 82
Compounds of the formula IB.3', in which $R^\alpha$ is methyl, $R^\beta$ is ethyl, $R^1$ is methyl and for each compound W corresponds to one row of Table C Table 83
Compounds of the formula IB.3", in which $R^\alpha$ is methyl, $R^\beta$ is ethyl, $R^1$ is methyl and for each compound W corresponds to one row of Table C Table 84
Compounds of the formula IB.4', in which $R^\alpha$ is methyl, $R^\beta$ is ethyl, $R^1$ is methyl and for each compound the combination of the radicals $R^2$ and $R^3$ corresponds to one row of Table D Table 85
Compounds of the formula IB.4', in which $R^\alpha$ is methyl, $R^\beta$ is ethyl, $R^1$ is methoxy and for each compound the combination of the radicals $R^2$ and $R^3$ corresponds to one row of Table D Table 86
Compounds of the formula IB.4", in which $R^\alpha$ is methyl, $R^\beta$ is ethyl, $R^1$ is methyl and for each compound the combination of the radicals $R^2$ and $R^3$ corresponds to one row of Table D Table 87
Compounds of the formula IB.4", in which $R^\alpha$ is methyl, $R^\beta$ is ethyl, $R^1$ is methoxy and for each compound the combination of the radicals $R^2$ and $R^3$ corresponds to one row of Table D Table 88
Compounds of the formula IB.5", in which $R^\alpha$ is methyl, $R^\beta$ is ethyl and for each compound W corresponds to one row of Table C Table 89
Compounds of the formula IB.6', in which $R^\alpha$ is methyl, $R^\beta$ is ethyl and for each compound W corresponds to one row of Table C Table 90
Compounds of the formula IB.6", in which $R^\alpha$ is methyl, $R^\beta$ is ethyl and for each compound W corresponds to one row of Table C Table 91
Compounds of the formula IB.7', in which $R^\alpha$ is methyl, $R^\beta$ is ethyl and for each compound W corresponds to one row of Table C Table 92
Compounds of the formula IB.1', in which $R^\alpha$ is methyl, $R^\beta$ is trifluoromethyl and for each compound Z corresponds to one row of Table A Table 93
Compounds of the formula IB.1", in which $R^\alpha$ is methyl, $R^\beta$ is trifluoromethyl and for each compound Z corresponds to one row of Table B Table 94
Compounds of the formula IB.2', in which $R^\alpha$ is methyl, $R^\beta$ is trifluoromethyl and for each compound Z corresponds to one row of Table B Table 95
Compounds of the formula IB.3', in which $R^\alpha$ is methyl, $R^\beta$ is trifluoromethyl, $R^1$ is methyl and for each compound W corresponds to one row of Table C Table 96
Compounds of the formula IB.3", in which $R^\alpha$ is methyl, $R^\beta$ is trifluoromethyl, $R^1$ is methyl and for each compound W corresponds to one row of Table C Table 97
Compounds of the formula IB.4', in which $R^\alpha$ is methyl, $R^\beta$ is trifluoromethyl, $R^1$ is methyl and for each compound the combination of the radicals $R^2$ and $R^3$ corresponds to one row of Table D Table 98
Compounds of the formula IB.4', in which $R^\alpha$ is methyl, $R^\beta$ is trifluoromethyl, $R^1$ is methoxy and for each compound the combination of the radicals $R^2$ and $R^3$ corresponds to one row of Table D Table 99
Compounds of the formula IB.4", in which $R^\alpha$ is methyl, $R^\beta$ is trifluoromethyl, $R^1$ is methyl and for each compound the combination of the radicals $R^2$ and $R^3$ corresponds to one row of Table D Table 100
Compounds of the formula IB.4", in which $R^\alpha$ is methyl, $R^\beta$ is trifluoromethyl, $R^1$ is methoxy and for each compound the combination of the radicals $R^2$ and $R^3$ corresponds to one row of Table D Table 101
Compounds of the formula IB.5", in which $R^\alpha$ is methyl, $R^\beta$ is trifluoromethyl and for each compound W corresponds to one row of Table C Table 102
Compounds of the formula IB.6', in which $R^\alpha$ is methyl, $R^\beta$ is trifluoromethyl and for each compound W corresponds to one row of Table C Table 103
Compounds of the formula IB.6", in which $R^\alpha$ is methyl, $R^\beta$ is trifluoromethyl and for each compound W corresponds to one row of Table C Table 104
Compounds of the formula IB.7', in which $R^\alpha$ is methyl, $R^\beta$ is trifluoromethyl and for each compound W corresponds to one row of Table C Table 105
Compounds of the formula IB.1', in which $R^\alpha$ is methyl, $R^\beta$ is cyclopropyl and for each compound Z corresponds to one row of Table A Table 106
Compounds of the formula IB.1", in which $R^\alpha$ is methyl, $R^\beta$ is cyclopropyl and for each compound Z corresponds to one row of Table B Table 107
Compounds of the formula IB.2', in which $R^\alpha$ is methyl, $R^\beta$ is cyclopropyl, and for each compound Z corresponds to one row of Table B Table 108
Compounds of the formula IB.3', in which $R^\alpha$ is methyl, $R^\beta$ is cyclopropyl, $R^1$ is methyl and for each compound W corresponds to one row of Table C Table 109
Compounds of the formula IB.3", in which $R^\alpha$ is methyl, $R^\beta$ is cyclopropyl, $R^1$ is methyl and for each compound W corresponds to one row of Table C Table 110
Compounds of the formula IB.4', in which $R^\alpha$ is methyl, $R^\beta$ is cyclopropyl, $R^1$ is methyl and for each compound the combination of the radicals $R^2$ and $R^3$ corresponds to one row of Table D Table 111
Compounds of the formula IB.4', in which $R^\alpha$ is methyl, $R^\beta$ is cyclopropyl, $R^1$ is methoxy and for each compound the combination of the radicals $R^2$ and $R^3$ corresponds to one row of Table D Table 112
Compounds of the formula IB.4", in which $R^\alpha$ is methyl, $R^\beta$ is cyclopropyl, $R^1$ is methyl and for each compound the combination of the radicals $R^2$ and $R^3$ corresponds to one row of Table D Table 113
Compounds of the formula IB.4", in which $R^\alpha$ is methyl, $R^\beta$ is cyclopropyl, $R^1$ is methoxy and for each compound the combination of the radicals $R^2$ and $R^3$ corresponds to one row of Table D Table 114
Compounds of the formula IB.5", in which $R^\alpha$ is methyl, $R^\beta$ is cyclopropyl and for each compound W corresponds to one row of Table C Table 115
Compounds of the formula IB.6', in which $R^\alpha$ is methyl, $R^\beta$ is cyclopropyl and for each compound W corresponds to one row of Table C Table 116
Compounds of the formula IB.6", in which $R^\alpha$ is methyl, $R^\beta$ is cyclopropyl and for each compound W corresponds to one row of Table C Table 117
Compounds of the formula IB.7', in which $R^\alpha$ is methyl, $R^\beta$ is cyclopropyl and for each compound W corresponds to one row of Table C Table 118
Compounds of the formula IB.1', in which $R^\alpha$ is methyl, $R^\beta$ is benzyl and for each compound Z corresponds to one row of Table A Table 119
Compounds of the formula IB.1", in which $R^\alpha$ is methyl, $R^\beta$ is benzyl and for each compound Z corresponds to one row of Table B Table 120
Compounds of the formula IB.2', in which $R^\alpha$ is methyl, $R^\beta$ is benzyl and for each compound Z corresponds to one row of Table B Table 121
Compounds of the formula IB.3', in which $R^\alpha$ is methyl, $R^\beta$ is benzyl, $R^1$ is methyl and for each compound W corresponds to one row of Table C Table 122
Compounds of the formula IB.3", in which $R^\alpha$ is methyl, $R^\beta$ is benzyl, $R^1$ is methyl and for each compound W corresponds to one row of Table C Table 123
Compounds of the formula IB.4', in which $R^\alpha$ is methyl, $R^\beta$ is benzyl, $R^1$ is methyl and for each compound the combination of the radicals $R^2$ and $R^3$ corresponds to one row of Table D Table 124
Compounds of the formula IB.4', in which $R^\alpha$ is methyl, $R^\beta$ is benzyl, $R^1$ is methoxy and for each compound the combination of the radicals $R^2$ and $R^3$ corresponds to one row of Table D Table 125
Compounds of the formula IB.4", in which $R^\alpha$ is methyl, $R^\beta$ is benzyl, $R^1$ is methyl and for each compound the combination of the radicals $R^2$ and $R^3$ corresponds to one row of Table D Table 126
Compounds of the formula IB.4", in which $R^\alpha$ is methyl, $R^\beta$ is benzyl, $R^1$ is methoxy and for each compound the combination of the radicals $R^2$ and $R^3$ corresponds to one row of Table D Table 127
Compounds of the formula IB.5", in which $R^\alpha$ is methyl, $R^\beta$ is benzyl and for each compound W corresponds to one row of Table C Table 128
Compounds of the formula IB.6', in which $R^\alpha$ is methyl, $R^\beta$ is benzyl and for each compound W corresponds to one row of Table C Table 129
Compounds of the formula IB.6", in which $R^\alpha$ is methyl, $R^\beta$ is benzyl and for each compound W corresponds to one row of Table C Table 130
Compounds of the formula IB.7', in which $R^\alpha$ is methyl, $R^\beta$ is benzyl and for each compound W corresponds to one row of Table C Table 131
Compounds of the formula IB.1', in which $R^\alpha$ is ethyl and $R^\beta$ is hydrogen and for each compound Z corresponds to one row of Table A Table 132
Compounds of the formula IB.1", in which $R^\alpha$ is ethyl and $R^\beta$ is hydrogen and for each compound Z corresponds to one row of Table B Table 133
Compounds of the formula IB.2', in which $R^\alpha$ is ethyl and $R^\beta$ is hydrogen and for each compound Z corresponds to one row of Table B Table 134
Compounds of the formula IB.3', in which $R^\alpha$ is ethyl and $R^\beta$ is hydrogen, $R^1$ is methyl and for each compound W corresponds to one row of Table C Table 135
Compounds of the formula IB.3", in which $R^\alpha$ is ethyl and $R^\beta$ is hydrogen, $R^1$ is methyl and for each compound W corresponds to one row of Table C Table 136
Compounds of the formula IB.4', in which $R^\alpha$ is ethyl and $R^\beta$ is hydrogen and $R^1$ is methyl and for each compound the combination of the radicals $R^2$ and $R^3$ corresponds to one row of Table D Table 137
Compounds of the formula IB.4', in which $R^\alpha$ is ethyl and $R^\beta$ is hydrogen and $R^1$ is methoxy and for each compound the combination of the radicals $R^2$ and $R^3$ corresponds to one row of Table D Table 138
Compounds of the formula IB.4", in which $R^\alpha$ is ethyl and $R^\beta$ is hydrogen and $R^1$ is methyl and for each compound the combination of the radicals $R^2$ and $R^3$ corresponds to one row of Table D Table 139
Compounds of the formula IB.4", in which $R^\alpha$ is ethyl and $R^\beta$ is hydrogen, $R^1$ is methoxy and for each compound the combination of the radicals $R^2$ and $R^3$ corresponds to one row of Table D Table 140
Compounds of the formula IB.5", in which $R^\alpha$ is ethyl and $R^\beta$ is hydrogen and for each compound W corresponds to one row of Table C Table 141
Compounds of the formula IB.6', in which $R^\alpha$ is ethyl and $R^\beta$ is hydrogen and for each compound W corresponds to one row of Table C Table 142
Compounds of the formula IB.6", in which $R^\alpha$ is ethyl and $R^\beta$ is hydrogen and for each compound W corresponds to one row of Table C Table 143
Compounds of the formula IB.7', in which $R^\alpha$ is ethyl and $R^\beta$ is hydrogen and for each compound W corresponds to one row of Table C Table 144
Compounds of the formula IB.1', in which $R^\alpha$ is ethyl, $R^\beta$ is methyl and for each compound Z corresponds to one row of Table A Table 145
Compounds of the formula IB.1", in which $R^\alpha$ is ethyl, $R^\beta$ is methyl and for each compound Z corresponds to one row of Table B Table 146
Compounds of the formula IB.2', in which $R^\alpha$ is ethyl, $R^\beta$ is methyl and for each compound Z corresponds to one row of Table B Table 147
Compounds of the formula IB.3', in which $R^\alpha$ is ethyl, $R^\beta$ is methyl, $R^1$ is methyl and for each compound W corresponds to one row of Table C Table 148
Compounds of the formula IB.3", in which $R^\alpha$ is ethyl, $R^\beta$ is methyl, $R^1$ is methyl and for each compound W corresponds to one row of Table C Table 149
Compounds of the formula IB.4', in which $R^\alpha$ is ethyl, $R^\beta$ and $R^1$ is methyl and for each compound the combination of the radicals $R^2$ and $R^3$ corresponds to one row of Table D Table 150
Compounds of the formula IB.4', in which $R^\alpha$ is ethyl, $R^\beta$ is methyl, $R^1$ is methoxy and for each compound the combination of the radicals $R^2$ and $R^3$ corresponds to one row of Table D Table 151
Compounds of the formula IB.4", in which $R^\alpha$ is ethyl, $R^\beta$ and $R^1$ are methyl and for each compound the combination of the radicals $R_2$ and $R^3$ corresponds to one row of Table D Table 152
Compounds of the formula IB.4", in which $R^\alpha$ is ethyl, $R^\beta$ is methyl, $R^1$ is methoxy and for each compound the combination of the radicals $R^2$ and $R^3$ corresponds to one row of Table D Table 153
Compounds of the formula IB.5", in which $R^\alpha$ is ethyl, $R^\beta$ is methyl and for each compound W corresponds to one row of Table C Table 154
Compounds of the formula IB.6', in which $R^\alpha$ is ethyl, $R^\beta$ is methyl and for each compound W corresponds to one row of Table C Table 155
Compounds of the formula IB.6", in which $R^\alpha$ is ethyl, $R^\beta$ is methyl and for each compound W corresponds to one row of Table C Table 156
Compounds of the formula IB.7', in which $R^\alpha$ is ethyl, $R^\beta$ is methyl and for each compound W corresponds to one row of Table C Table 157
Compounds of the formula IB.1', in which $R^\alpha$ and $R^\beta$ are ethyl and for each compound Z corresponds to one row of Table A Table 158
Compounds of the formula IB.1", in which $R^\alpha$ and $R^\beta$ are ethyl and for each compound Z corresponds to one row of Table B Table 159
Compounds of the formula IB.2', in which $R^\alpha$ and $R^\beta$ are ethyl and for each compound Z corresponds to one row of Table B Table 160
Compounds of the formula IB.3', in which $R^\alpha$ and $R^\beta$ are ethyl, $R^1$ is methyl and for each compound W corresponds to one row of Table C Table 161
Compounds of the formula IB.3", in which $R^\alpha$ and $R^\beta$ are ethyl, $R^1$ is methyl and for each compound W corresponds to one row of Table C Table 162
Compounds of the formula IB.4', in which $R^\alpha$ and $R^\beta$ are ethyl, $R^1$ is methyl and for each compound the combination of the radicals $R^2$ and $R^3$ corresponds to one row of Table D Table 163
Compounds of the formula IB.4', in which $R^\alpha$ and $R^\beta$ are ethyl, $R^1$ is methoxy and for each compound the combination of the radicals $R^2$ and $R^3$ corresponds to one row of Table D Table 164
Compounds of the formula IB.4", in which $R^\alpha$ and $R^\beta$ are ethyl, $R^1$ is methyl and for each compound the combination of the radicals $R^2$ and $R^3$ corresponds to one row of Table D Table 165
Compounds of the formula IB.4", in which $R^\alpha$ and $R^\beta$ are ethyl, $R^1$ is methoxy and for each compound the combination of the radicals $R^2$ and $R^3$ corresponds to one row of Table D Table 166
Compounds of the formula IB.5", in which $R^\alpha$ and $R^\beta$ are ethyl and for each compound W corresponds to one row of Table C Table 167
Compounds of the formula IB.6', in which $R^\alpha$ and $R^\beta$ are ethyl and for each compound W corresponds to one row of Table C Table 168
Compounds of the formula IB.6", in which $R^\alpha$ and $R^\beta$ are ethyl and for each compound W corresponds to one row of Table C Table 169
Compounds of the formula IB.7', in which $R^\alpha$ and $R^\beta$ are ethyl and for each compound W corresponds to one row of Table C Table 170
Compounds of the formula IB.1', in which $R^\alpha$ is ethyl, $R^\beta$ is trifluoromethyl and for each compound Z corresponds to one row of Table A Table 171
Compounds of the formula IB.1", in which $R^\alpha$ is ethyl, $R^\beta$ is trifluoromethyl and for each compound Z corresponds to one row of Table B Table 172
Compounds of the formula IB.2', in which $R^\alpha$ is ethyl, $R^\beta$ is trifluoromethyl and for each compound Z corresponds to one row of Table B Table 173
Compounds of the formula IB.3', in which $R^\alpha$ is ethyl, $R^\beta$ is trifluoromethyl, $R^1$ is methyl and for each compound W corresponds to one row of Table C Table 174
Compounds of the formula IB.3", in which $R^\alpha$ is ethyl, $R^\beta$ is trifluoromethyl, $R^1$ is methyl and for each compound W corresponds to one row of Table C Table 175
Compounds of the formula IB.4', in which $R^\alpha$ is ethyl, $R^\beta$ is trifluoromethyl, $R^1$ is methyl and for each compound the combination of the radicals $R^2$ and $R^3$ corresponds to one row of Table D Table 176
Compounds of the formula IB.4', in which $R^\alpha$ is ethyl, $R^\beta$ is trifluoromethyl, $R^1$ is methoxy and for each compound the combination of the radicals $R^2$ and $R^3$ corresponds to one row of Table D Table 177
Compounds of the formula IB.4", in which $R^\alpha$ is ethyl, $R^\beta$ is trifluoromethyl, $R^1$ is methyl and for each compound the combination of the radicals $R^2$ and $R^3$ corresponds to one row of Table D Table 178
Compounds of the formula IB.4", in which $R^\alpha$ is ethyl, $R^\beta$ is trifluoromethyl, $R^1$ is methoxy and for each compound the combination of the radicals $R^2$ and $R^3$ corresponds to one row of Table D Table 179
Compounds of the formula IB.5", in which $R^\alpha$ is ethyl, $R^\beta$ is trifluoromethyl and for each compound W corresponds to one row of Table C Table 180
Compounds of the formula IB.6', in which $R^\alpha$ is ethyl, $R^\beta$ is trifluoromethyl and for each compound W corresponds to one row of Table C Table 181
Compounds of the formula IB.6", in which $R^\alpha$ is ethyl, $R^\beta$ is trifluoromethyl and for each compound W corresponds to one row of Table C Table 182
Compounds of the formula IB.7', in which $R^\alpha$ is ethyl, $R^\beta$ is rifluoromethyl and for each compound W corresponds to one row of Table C Table 183
Compounds of the formula IB.1', in which $R^\alpha$ is ethyl, $R^\beta$ is cyclopropyl and for each compound Z corresponds to one row of Table A Table 184
Compounds of the formula IB.1", in which $R^\alpha$ is ethyl, $R^\beta$ is cyclopropyl and for each compound Z corresponds to one row of Table B Table 185
Compounds of the formula IB.2', in which $R^\alpha$ is ethyl, $R^\beta$ is cyclopropyl and for each compound Z corresponds to one row of Table B Table 186
Compounds of the formula IB.3', in which $R^\alpha$ is ethyl, $R^\beta$ is cyclopropyl, $R^1$ is methyl and for each compound W corresponds to one row of Table C Table 187
Compounds of the formula IB.3", in which $R^\alpha$ is ethyl, $R^\beta$ is cyclopropyl, $R^1$ is methyl and for each compound W corresponds to one row of Table C Table 188
Compounds of the formula IB.4', in which $R^\alpha$ is ethyl, $R^\beta$ is cyclopropyl, $R^1$ is methyl and for each compound the combination of the radicals $R^2$ and $R^3$ corresponds to one row of Table D Table 189
Compounds of the formula IB.4', in which $R^\alpha$ is ethyl, $R^\beta$ is cyclopropyl, $R^1$ is methoxy and for each compound the combination of the radicals $R^2$ and $R^3$ corresponds to one row of Table D Table 190
Compounds of the formula IB.4", in which $R^\alpha$ is ethyl, $R^\beta$ is cyclopropyl, $R^1$ is methyl and for each compound the combination of the radicals $R^2$ and $R^3$ corresponds to one row of Table D Table 191
Compounds of the formula IB.4", in which $R^\alpha$ is ethyl, $R^\beta$ is cyclopropyl, $R^1$ is methoxy and for each compound the combination of the radicals $R^2$ and $R^3$ corresponds to one row of Table D Table 192
Compounds of the formula IB.5", in which $R^\alpha$ is ethyl, $R^\beta$ is cyclopropyl and for each compound W corresponds to one row of Table C Table 193
Compounds of the formula IB.6', in which $R^\alpha$ is ethyl, $R^\beta$ is cyclopropyl and for each compound W corresponds to one row of Table C Table 194
Compounds of the formula IB.6', in which $R^\alpha$ is ethyl, $R^\beta$ is cyclopropyl and for each compound W corresponds to one row of Table C Table 195
Compounds of the formula IB.7', in which $R^\alpha$ is ethyl, $R^\beta$ is cyclopropyl and for each compound W corresponds to one row of Table C Table 196
Compounds of the formula IB.1', in which $R^\alpha$ is ethyl, $R^\beta$ is benzyl and for each compound Z corresponds to one row of Table A Table 197
Compounds of the formula IB.1", in which $R^\alpha$ is ethyl, $R^\beta$ is benzyl and for each compound Z corresponds to one row of Table B Table 198
Compounds of the formula IB.2', in which $R^\alpha$ is ethyl, $R^\beta$ is benzyl and for each compound Z corresponds to one row of Table B Table 199
Compounds of the formula IB.3', in which $R^\alpha$ is ethyl, $R^\beta$ is benzyl, $R^1$ is methyl and for each compound W corresponds to one row of Table C Table 200
Compounds of the formula IB.3", in which $R^\alpha$ is ethyl, $R^\beta$ is benzyl, $R^1$ is methyl and for each compound W corresponds to one row of Table C Table 201
Compounds of the formula IB.4', in which $R^\alpha$ is ethyl, $R^\beta$ is benzyl, $R^1$ is methyl and for each compound the combination of the radicals $R^2$ and $R^3$ corresponds to one row of Table D Table 202
Compounds of the formula IB.4', in which $R^\alpha$ is ethyl, $R^\beta$ is benzyl, $R^1$ is methoxy and for each compound the combination of the radicals $R^2$ and $R^3$ corresponds to one row of Table D Table 203
Compounds of the formula IB.4", in which $R^\alpha$ is ethyl, $R^\beta$ is benzyl, $R^1$ is methyl and for each compound the combination of the radicals $R^2$ and $R^3$ corresponds to one row of Table D Table 204
Compounds of the formula IB.4", in which $R^\alpha$ is ethyl, $R^\beta$ is benzyl, $R^1$ is methoxy and for each compound the combination of the radicals $R^2$ and $R^3$ corresponds to one row of Table D Table 205
Compounds of the formula IB.5", in which $R^\alpha$ is ethyl, $R^\beta$ is benzyl and for each compound W corresponds to one row of Table C Table 206
Compounds of the formula IB.6', in which $R^\alpha$ is ethyl, $R^\beta$ is benzyl and for each compound W corresponds to one row of Table C Table 207
Compounds of the formula IB.6", in which $R^\alpha$ is ethyl, $R^\beta$ is benzyl and for each compound W corresponds to one row of Table C Table 208
Compounds of the formula IB.7', in which $R^\alpha$ is ethyl, $R^\beta$ is benzyl and for each compound W corresponds to one row of Table C Table 209
Compounds of the formula IB.1', in which $R^\alpha$ is trifluoromethyl and $R^\beta$ is hydrogen and for each compound Z corresponds to one row of Table A Table 210
Compounds of the formula IB.1", in which $R^\alpha$ is trifluoromethyl and $R^\beta$ is hydrogen and for each compound Z corresponds to one row of Table B Table 211
Compounds of the formula IB.2', in which $R^\alpha$ is trifluoromethyl and $R^\beta$ is hydrogen and for each compound Z corresponds to one row of Table B Table 212
Compounds of the formula IB.3', in which $R^\alpha$ is trifluoromethyl and $R^\beta$ is hydrogen, $R^1$ is methyl and for each compound W corresponds to one row of Table C Table 213
Compounds of the formula IB.3", in which $R^\alpha$ is trifluoromethyl and $R^\beta$ is hydrogen, $R^1$ is methyl and for each compound W corresponds to one row of Table C Table 214
Compounds of the formula IB.4', in which $R^\alpha$ is trifluoromethyl and $R^\beta$ is hydrogen and $R^1$ is methyl and for each compound the combination of the radicals $R^2$ and $R^3$ corresponds to one row of Table D Table 215
Compounds of the formula IB.4', in which $R^\alpha$ is trifluoromethyl and $R^\beta$ is hydrogen, $R^1$ is methoxy and for each compound the combination of the radicals $R^2$ and $R^3$ corresponds to one row of Table D Table 216
Compounds of the formula IB.4", in which $R^\alpha$ is trifluoromethyl and $R^\beta$ is hydrogen and $R^1$ is methyl and for each compound the combination of the radicals $R^2$ and $R^3$ corresponds to one row of Table D Table 217
Compounds of the formula IB.4", in which $R^\alpha$ is trifluoromethyl and $R^\beta$ is hydrogen, $R^1$ is methoxy and for each compound the combination of the radicals $R^2$ and $R^3$ corresponds to one row of Table D Table 218
Compounds of the formula IB.5", in which $R^\alpha$ is trifluoromethyl and $R^\beta$ is hydrogen and for each compound W corresponds to one row of Table C Table 219
Compounds of the formula IB.6', in which $R^\alpha$ is trifluoromethyl and $R^\beta$ is hydrogen and for each compound W corresponds to one row of Table C Table 220
Compounds of the formula IB.6", in which $R^\alpha$ is trifluoromethyl and $R^\beta$ is hydrogen and for each compound W corresponds to one row of Table C Table 221
Compounds of the formula IB.7', in which $R^\alpha$ is trifluoromethyl and $R^\beta$ is hydrogen and for each compound W corresponds to one row of Table C Table 222
Compounds of the formula IB.1', in which $R^\alpha$ is trifluoromethyl, $R^\beta$ is methyl and for each compound Z corresponds to one row of Table A Table 223
Compounds of the formula IB.1", in which $R^\alpha$ is trifluoromethyl, $R^\beta$ is methyl and for each compound Z corresponds to one row of Table B Table 224
Compounds of the formula IB.2', in which $R^\alpha$ is trifluoromethyl, $R^\beta$ is methyl and for each compound Z corresponds to one row of Table B Table 225
Compounds of the formula IB.3', in which $R^\alpha$ is trifluoromethyl, $R^\beta$ is methyl, $R^1$ is methyl and for each compound W corresponds to one row of Table C Table 226
Compounds of the formula IB.3", in which $R^\alpha$ is trifluoromethyl, $R^\beta$ is methyl, $R^1$ is methyl and for each compound W corresponds to one row of Table C Table 227
Compounds of the formula IB.4', in which $R^\alpha$ is trifluoromethyl, $R^\beta$ and $R^1$ is methyl and for each compound the combination of the radicals $R^2$ and $R^3$ corresponds to one row of Table D Table 228
Compounds of the formula IB.4', in which $R^\alpha$ is trifluoromethyl, $R^\beta$ is methyl, $R^1$ is methoxy and for each compound the combination of the radicals $R^2$ and $R^3$ corresponds to one row of Table D Table 229
Compounds of the formula IB.4", in which $R^\alpha$ is trifluoromethyl, $R^\beta$ and $R^1$ are methyl and for each compound the combination of the radicals $R^2$ and $R^3$ corresponds to one row of Table D Table 230
Compounds of the formula IB.4", in which $R^\alpha$ is trifluoromethyl, $R^\beta$ is methyl, $R^1$ is methoxy and for each compound the combination of the radicals $R^2$ and $R^3$ corresponds to one row of Table D Table 231
Compounds of the formula IB.5", in which $R^\alpha$ is trifluoromethyl, $R^\beta$ is methyl and for each compound W corresponds to one row of Table C Table 232
Compounds of the formula IB.6', in which $R^\alpha$ is trifluoromethyl, $R^\beta$ is methyl and for each compound W corresponds to one row of Table C Table 233
Compounds of the formula IB.6", in which $R^\alpha$ is trifluoromethyl, $R^\beta$ is methyl and for each compound W corresponds to one row of Table C Table 234
Compounds of the formula IB.7', in which $R^\alpha$ is trifluoromethyl, $R^\beta$ is methyl and for each compound W corresponds to one row of Table C Table 235
Compounds of the formula IB.1', in which $R^\alpha$ and $R^\beta$ are ethyl and for each compound Z corresponds to one row of Table A Table 236
Compounds of the formula IB.1", in which $R^\alpha$ is trifluoromethyl and $R^\beta$ is ethyl and for each compound Z corresponds to one row of Table B Table 237
Compounds of the formula IB.2', in which $R^\alpha$ is trifluoromethyl and $R^\beta$ is ethyl and for each compound Z corresponds to one row of Table B Table 238
Compounds of the formula IB.3', in which $R^\alpha$ is trifluoromethyl and $R^\beta$ is ethyl, $R^1$ is methyl and for each compound W corresponds to one row of Table C Table 239
Compounds of the formula IB.3", in which $R^\alpha$ is trifluoromethyl and $R^\beta$ is ethyl, $R^1$ is methyl and for each compound W corresponds to one row of Table C Table 240
Compounds of the formula IB.4', in which $R^\alpha$ is trifluoromethyl and $R^\beta$ is ethyl, $R^1$ is methyl and for each compound the combination of the radicals $R^2$ and $R^3$ corresponds to one row of Table D Table 241
Compounds of the formula IB.4', in which $R^\alpha$ is trifluoromethyl and $R^\beta$ is ethyl, $R^1$ is methoxy and for each compound the combination of the radicals $R^2$ and $R^3$ corresponds to one row of Table D Table 242
Compounds of the formula IB.4", in which $R^\alpha$ is trifluoromethyl and $R^\beta$ is ethyl, $R^1$ is methyl and for each compound the combination of the radicals $R^2$ and $R^3$ corresponds to one row of Table D Table 243
Compounds of the formula IB.4", in which $R^\alpha$ is trifluoromethyl and $R^\beta$ is ethyl, $R^1$ is methoxy and for each compound the combination of the radicals $R^2$ and $R^3$ corresponds to one row of Table D Table 244
Compounds of the formula IB.5", in which $R^\alpha$ is trifluoromethyl and $R^\beta$ is ethyl and for each compound W corresponds to one row of Table C Table 245
Compounds of the formula IB.6', in which $R^\alpha$ is trifluoromethyl and $R^\beta$ is ethyl and for each compound W corresponds to one row of Table C Table 246
Compounds of the formula IB.6", in which $R^\alpha$ is trifluoromethyl and $R^\beta$ is ethyl and for each compound W corresponds to one row of Table C Table 247
Compounds of the formula IB.7', in which $R^\alpha$ is trifluoromethyl and $R^\beta$ is ethyl and for each compound W corresponds to one row of Table C Table 248
Compounds of the formula IB.1', in which $R^\alpha$ and $R^\beta$ are trifluoromethyl and for each compound Z corresponds to one row of Table A Table 249
Compounds of the formula IB.1", in which $R^\alpha$ and $R^\beta$ are trifluoromethyl and for each compound Z corresponds to one row of Table B Table 250
Compounds of the formula IB.2', in which $R^\alpha$ and $R^\beta$ are trifluoromethyl and for each compound Z corresponds to one row of Table B Table 251
Compounds of the formula IB.3', in which $R^\alpha$ and $R^\beta$ are trifluoromethyl, $R^1$ is methyl and for each compound W corresponds to one row of Table C Table 252
Compounds of the formula IB.3", in which $R^\alpha$ and $R^\beta$ are trifluoromethyl, $R^1$ is methyl and for each compound W corresponds to one row of Table C Table 253
Compounds of the formula IB.4', in which $R^\alpha$ and $R^\beta$ are trifluoromethyl, $R^1$ is methyl and for each compound the combination of the radicals $R^2$ and $R^3$ corresponds to one row of Table D Table 254
Compounds of the formula IB.4', in which $R^\alpha$ and $R^\beta$ are trifluoromethyl, $R^1$ is methoxy and for each compound the combination of the radicals $R^2$ and $R^3$ corresponds to one row of Table D Table 255
Compounds of the formula IB.4", in which $R^\alpha$ and $R^\beta$ are trifluoromethyl, $R^1$ is methyl and for each compound the combination of the radicals $R^2$ and $R^3$ corresponds to one row of Table D Table 256
Compounds of the formula IB.4", in which $R^\alpha$ and $R^\beta$ are trifluoromethyl, $R^1$ is methoxy and for each compound the combination of the radicals $R^2$ and $R^3$ corresponds to one row of Table D Table 257
Compounds of the formula IB.5", in which $R^\alpha$ and $R^\beta$ are trifluoromethyl and for each compound W corresponds to one row of Table C Table 258
Compounds of the formula IB.6', in which $R^\alpha$ and $R^\beta$ are trifluoromethyl and for each compound W corresponds to one row of Table C Table 259
Compounds of the formula IB.6", in which $R^\alpha$ and $R^\beta$ are trifluoromethyl and for each compound W corresponds to one row of Table C Table 260
Compounds of the formula IB.7', in which $R^\alpha$ and $R^\beta$ are trifluoromethyl and for each compound W corresponds to one row of Table C Table 261
Compounds of the formula IB.1', in which $R^\alpha$ is trifluoromethyl and $R^\beta$ is cyclopropyl and for each compound Z corresponds to one row of Table A Table 262
Compounds of the formula IB.1", in which $R^\alpha$ is trifluoromethyl, $R^\beta$ is cyclopropyl and for each compound Z corresponds to one row of Table B Table 263
Compounds of the formula IB.2', in which $R^\alpha$ is trifluoromethyl, $R^\beta$ is cyclopropyl and for each compound Z corresponds to one row of Table B Table 264
Compounds of the formula IB.3', in which $R^\alpha$ is trifluoromethyl, $R^\beta$ is cyclopropyl, $R^1$ is methyl and for each compound W corresponds to one row of Table C Table 265
Compounds of the formula IB.3", in which $R^\alpha$ is trifluoromethyl, $R^\beta$ is cyclopropyl, $R^1$ is methyl and for each compound W corresponds to one row of Table C Table 266
Compounds of the formula IB.4', in which $R^\alpha$ is trifluoromethyl, $R^\beta$ is cyclopropyl, $R^1$ is methyl and for each compound the combination of the radicals $R^2$ and $R^3$ corresponds to one row of Table D Table 267
Compounds of the formula IB.4', in which $R^\alpha$ is trifluoromethyl, $R^\beta$ is cyclopropyl, $R^1$ is methoxy and for each compound the combination of the radicals $R^2$ and $R^3$ corresponds to one row of Table D Table 268
Compounds of the formula IB.4", in which $R^\alpha$ is trifluoromethyl, $R^\beta$ is cyclopropyl, $R^1$ is methyl and for each compound the combination of the radicals $R^2$ and $R^3$ corresponds to one row of Table D Table 269
Compounds of the formula IB.4", in which $R^\alpha$ is trifluoromethyl, $R^\beta$ is cyclopropyl, $R^1$ is methoxy and for each compound the combination of the radicals $R^2$ and $R^3$ corresponds to one row of Table D Table 270
Compounds of the formula IB.5", in which $R^\alpha$ is trifluoromethyl, $R^\beta$ is cyclopropyl and for each compound W corresponds to one row of Table C Table 271
Compounds of the formula IB.6', in which $R^\alpha$ is trifluoromethyl, $R^\beta$ is cyclopropyl and for each compound W corresponds to one row of Table C Table 272
Compounds of the formula IB.6", in which $R^\alpha$ is trifluoromethyl, $R^\beta$ is cyclopropyl and for each compound W corresponds to one row of Table C Table 273
Compounds of the formula IB.7', in which $R^\alpha$ is trifluoromethyl, $R^\beta$ is cyclopropyl and for each compound W corresponds to one row of Table C Table 274
Compounds of the formula IB.1', in which $R^\alpha$ is trifluoromethyl, $R^\beta$ is benzyl and for each compound Z corresponds to one row of Table A Table 275
Compounds of the formula IB.1", in which $R^\alpha$ is trifluoromethyl, $R^\beta$ is benzyl and for each compound Z corresponds to one row of Table B Table 276
Compounds of the formula IB.2', in which $R^\alpha$ is trifluoromethyl, $R^\beta$ is benzyl and for each compound Z corresponds to one row of Table B Table 277
Compounds of the formula IB.3', in which $R^\alpha$ is trifluoromethyl, $R^\beta$ is benzyl, $R^1$ is methyl and for each compound W corresponds to one row of Table C Table 278
Compounds of the formula IB.3", in which $R^\alpha$ is trifluoromethyl, $R^\beta$ is benzyl, $R^1$ is methyl and for each compound W corresponds to one row of Table C Table 279
Compounds of the formula IB.4', in which $R^\alpha$ is trifluoromethyl, $R^\beta$ is benzyl, $R^1$ is methyl and for each compound the combination of the radicals $R^2$ and $R^3$ corresponds to one row of Table D Table 280
Compounds of the formula IB.4', in which $R^\alpha$ is trifluoromethyl, $R^\beta$ is benzyl, $R^1$ is methoxy and for each compound the combination of the radicals $R^2$ and $R^3$ corresponds to one row of Table D Table 281
Compounds of the formula IB.4", in which $R^\alpha$ is trifluoromethyl, $R^\beta$ is benzyl, $R^1$ is methyl and for each compound the combination of the radicals $R^2$ and $R^3$ corresponds to one row of Table D Table 282
Compounds of the formula IB.4", in which $R^\alpha$ is trifluoromethyl, $R^\beta$ is benzyl, $R^1$ is methoxy and for each compound the combination of the radicals $R^2$ and $R^3$ corresponds to one row of Table D Table 283
Compounds of the formula IB.5", in which $R^\alpha$ is trifluoromethyl, $R^\beta$ is benzyl and for each compound W corresponds to one row of Table C Table 284
Compounds of the formula IB.6', in which $R^\alpha$ is trifluoromethyl, $R^\beta$ is benzyl and for each compound W corresponds to one row of Table C Table 285
Compounds of the formula IB.6", in which $R^\alpha$ is trifluoromethyl, $R^\beta$ is benzyl and for each compound W corresponds to one row of Table C Table 286
Compounds of the formula IB.7', in which $R^\alpha$ is trifluoromethyl, $R^\beta$ is benzyl and for each compound W corresponds to one row of Table C Table 287
Compounds of the formula IB.1', in which $R^\alpha$ is cyclopropyl and $R^\beta$ is hydrogen and for each compound Z corresponds to one row of Table A Table 288
Compounds of the formula IB.1", in which $R^\alpha$ is cyclopropyl and $R^\beta$ is hydrogen and for each compound Z corresponds to one row of Table B Table 289
Compounds of the formula IB.2', in which $R^\alpha$ is cyclopropyl and $R^\beta$ is hydrogen and for each compound Z corresponds to one row of Table B Table 290
Compounds of the formula IB.3', in which $R^\alpha$ is cyclopropyl and $R^\beta$ is hydrogen, $R^1$ is methyl and for each compound W corresponds to one row of Table C Table 291
Compounds of the formula IB.3", in which $R^\alpha$ is cyclopropyl and $R^\beta$ is hydrogen, $R^1$ is methyl and for each compound W corresponds to one row of Table C Table 292
Compounds of the formula IB.4', in which $R^\alpha$ is cyclopropyl and $R^\beta$ is hydrogen and $R^1$ is methyl and for each compound the combination of the radicals $R^2$ and $R^3$ corresponds to one row of Table D Table 293
Compounds of the formula IB.4', in which $R^\alpha$ is cyclopropyl and $R^\beta$ is hydrogen, $R^1$ is methoxy and for each compound the combination of the radicals $R^2$ and $R^3$ corresponds to one row of Table D Table 294
Compounds of the formula IB.4", in which $R^\alpha$ is cyclopropyl and $R^\beta$ is hydrogen and $R^1$ is methyl and for each compound the combination of the radicals $R^2$ and $R^3$ corresponds to one row of Table D Table 295
Compounds of the formula IB.4", in which $R^\alpha$ is cyclopropyl and $R^\beta$ is hydrogen, $R^1$ is methoxy and for each compound the combination of the radicals $R^2$ and $R^3$ corresponds to one row of Table D Table 296
Compounds of the formula IB.5", in which $R^\alpha$ is cyclopropyl and $R^\beta$ is hydrogen and for each compound W corresponds to one row of Table C Table 297
Compounds of the formula IB.6', in which $R^\alpha$ is cyclopropyl and $R^\beta$ is hydrogen and for each compound W corresponds to one row of Table C Table 298
Compounds of the formula IB.6", in which $R^\alpha$ is cyclopropyl and $R^\beta$ is hydrogen and for each compound W corresponds to one row of Table C Table 299
Compounds of the formula IB.7', in which $R^\alpha$ is cyclopropyl and $R^\beta$ is hydrogen and for each compound W corresponds to one row of Table C Table 300
Compounds of the formula IB.1', in which $R^\alpha$ is cyclopropyl, $R^\beta$ is methyl and for each compound Z corresponds to one row of Table A Table 301
Compounds of the formula IB.1", in which $R^\alpha$ is cyclopropyl, $R^\beta$ is methyl and for each compound Z corresponds to one row of Table B Table 302
Compounds of the formula IB.2', in which $R^\alpha$ is cyclopropyl, $R^\beta$ is methyl and for each compound Z corresponds to one row of Table B Table 303
Compounds of the formula IB.3', in which $R^\alpha$ is cyclopropyl, $R^\beta$ is methyl, $R^1$ is methyl and for each compound W corresponds to one row of Table C Table 304
Compounds of the formula IB.3", in which $R^\alpha$ is cyclopropyl, $R^\beta$ is methyl, $R^1$ is methyl and for each compound W corresponds to one row of Table C Table 305
Compounds of the formula IB.4', in which $R^\alpha$ is cyclopropyl, $R^\beta$ and $R^1$ are methyl and for each compound the combination of the radicals $R^2$ and $R^3$ corresponds to one row of Table D Table 306
Compounds of the formula IB.4', in which $R^\alpha$ is cyclopropyl, $R^\beta$ is methyl, $R^1$ is methoxy and for each compound the combination of the radicals $R^2$ and $R^3$ corresponds to one row of Table D Table 307
Compounds of the formula IB.4", in which $R^\alpha$ is cyclopropyl, $R^\beta$ and $R^1$ are methyl and for each compound the combination of the radicals $R^2$ and $R^3$ corresponds to one row of Table D Table 308
Compounds of the formula IB.4", in which $R^\alpha$ is cyclopropyl, $R^\beta$ is methyl, $R^1$ is methoxy and for each compound the combination of the radicals $R^2$ and $R^3$ corresponds to one row of Table D Table 309
Compounds of the formula IB.5", in which $R^\alpha$ is cyclopropyl, $R^\beta$ is methyl and for each compound W corresponds to one row of Table C Table 310
Compounds of the formula IB.6', in which $R^\alpha$ is cyclopropyl, $R^\beta$ is methyl and for each compound W corresponds to one row of Table C Table 311
Compounds of the formula IB.6", in which $R^\alpha$ is cyclopropyl, $R^\beta$ is methyl and for each compound W corresponds to one row of Table C Table 312
Compounds of the formula IB.7', in which $R^\alpha$ is cyclopropyl, $R^\beta$ is methyl and for each compound W corresponds to one row of Table C Table 313
Compounds of the formula IB.1', in which $R^\alpha$ is cyclopropyl and $R^\beta$ is ethyl and for each compound Z corresponds to one row of Table A Table 314
Compounds of the formula IB.1", in which $R^\alpha$ is cyclopropyl and $R^\beta$ is ethyl and for each compound Z corresponds to one row of Table B Table 315
Compounds of the formula IB.2', in which $R^\alpha$ is cyclopropyl and $R^\beta$ is ethyl and for each compound Z corresponds to one row of Table B Table 316
Compounds of the formula IB.3', in which $R^\alpha$ is cyclopropyl and $R^\beta$ is ethyl, $R^1$ is methyl and for each compound W corresponds to one row of Table C Table 317
Compounds of the formula IB.3", in which $R^\alpha$ is cyclopropyl and $R^\beta$ is ethyl, $R^1$ is methyl and for each compound W corresponds to one row of Table C Table 318
Compounds of the formula IB.4', in which $R^\alpha$ is cyclopropyl and $R^\beta$ is ethyl, $R^1$ is methyl and for each compound the combination of the radicals $R^2$ and $R^3$ corresponds to one row of Table D Table 319
Compounds of the formula IB.4', in which $R^\alpha$ is cyclopropyl and is ethyl, $R^1$ is methoxy and for each compound the combination of the radicals $R^2$ and $R^3$ corresponds to one row of Table D Table 320
Compounds of the formula IB.4", in which $R^\alpha$ is cyclopropyl and $R^\beta$ is ethyl, $R^1$ is methyl and for each compound the combination of the radicals $R^2$ and $R^3$ corresponds to one row of Table D Table 321
Compounds of the formula IB.4", in which $R^\alpha$ is cyclopropyl and $R^\beta$ is ethyl, $R^1$ is methoxy and for each compound the combination of the radicals $R^2$ and $R^3$ corresponds to one row of Table D Table 322
Compounds of the formula IB.5", in which $R^\alpha$ is cyclopropyl and $R^\beta$ is ethyl and for each compound W corresponds to one row of Table C Table 323
Compounds of the formula IB.6', in which $R^\alpha$ is cyclopropyl and $R^\beta$ is ethyl and for each compound W corresponds to one row of Table C Table 324
Compounds of the formula IB.6", in which $R^\alpha$ is cyclopropyl and $R^\beta$ is ethyl and for each compound W corresponds to one row of Table C Table 325
Compounds of the formula IB.7', in which $R^\alpha$ is cyclopropyl and $R^\beta$ is ethyl and for each compound W corresponds to one row of Table C Table 326
Compounds of the formula IB.1', in which $R^\alpha$ is cyclopropyl and $R^\beta$ is trifluoromethyl and for each compound Z corresponds to one row of Table A Table 327
Compounds of the formula IB.1", in which $R^\alpha$ is cyclopropyl and $R^\beta$ is trifluoromethyl and for each compound Z corresponds to one row of Table B Table 328
Compounds of the formula IB.2', in which $R^\alpha$ is cyclopropyl and $R^\beta$ is trifluoromethyl and for each compound Z corresponds to one row of Table B Table 329
Compounds of the formula IB.3', in which $R^\alpha$ is cyclopropyl and $R^\beta$ is trifluoromethyl, $R^1$ is methyl and for each compound W corresponds to one row of Table C Table 330
Compounds of the formula IB.3", in which $R^\alpha$ is cyclopropyl and $R^\beta$ is trifluoromethyl, $R^1$ is methyl and for each compound W corresponds to one row of Table C Table 331
Compounds of the formula IB.4', in which $R^\alpha$ is cyclopropyl and $R^\beta$ is trifluoromethyl, $R^1$ is methyl and for each compound the combination of the radicals $R^2$ and $R^3$ corresponds to one row of Table D Table 332
Compounds of the formula IB.4', in which $R^\alpha$ is cyclopropyl and $R^\beta$ is trifluoromethyl, $R^1$ is methoxy and for each compound the combination of the radicals $R^2$ and $R^3$ corresponds to one row of Table D Table 333
Compounds of the formula IB.4", in which $R^\alpha$ is cyclopropyl and $R^\beta$ is trifluoromethyl, $R^1$ is methyl and for each compound the combination of the radicals $R^2$ and $R^3$ corresponds to one row of Table D Table 334
Compounds of the formula IB.4", in which $R^\alpha$ is cyclopropyl and $R^\beta$ is trifluoromethyl, $R^1$ is methoxy and for each compound the combination of the radicals $R^2$ and $R^3$ corresponds to one row of Table D Table 335
Compounds of the formula IB.5", in which $R^\alpha$ is cyclopropyl and $R^\beta$ is trifluoromethyl and for each compound W corresponds to one row of Table C Table 336
Compounds of the formula IB.6', in which $R^\alpha$ is cyclopropyl and $R^\beta$ is trifluoromethyl and for each compound W corresponds to one row of Table C Table 337
Compounds of the formula IB.6|, in which $R^\alpha$ is cyclopropyl and $R^\beta$ is trifluoromethyl and for each compound W corresponds to one row of Table C Table 338
Compounds of the formula IB.7', in which $R^\alpha$ is cyclopropyl and $R^\beta$ is trifluoromethyl and for each compound W corresponds to one row of Table C Table 339
Compounds of the formula IB.1', in which $R^\alpha$ is cyclopropyl and $R^\beta$ is cyclopropyl and for each compound Z corresponds to one row of Table A Table 340
Compounds of the formula IB.1", in which $R^\alpha$ is cyclopropyl, $R^\beta$ is cyclopropyl and for each compound Z corresponds to one row of Table B Table 341
Compounds of the formula IB.2', in which $R^\alpha$ is cyclopropyl, $R^\beta$ is cyclopropyl and for each compound Z corresponds to one row of Table B Table 342
Compounds of the formula IB.3', in which $R^\alpha$ is cyclopropyl, $R^\beta$ is cyclopropyl, $R^1$ is methyl and for each compound W corresponds to one row of Table C Table 343
Compounds of the formula IB.3", in which $R^\alpha$ is cyclopropyl, $R^\beta$ is cyclopropyl, $R^1$ is methyl and for each compound W corresponds to one row of Table C Table 344
Compounds of the formula IB.4', in which $R^\alpha$ is cyclopropyl, $R^\beta$ is cyclopropyl, $R^1$ is methyl and for each compound the combination of the radicals $R^2$ and $R^3$ corresponds to one row of Table D Table 345
Compounds of the formula IB.4', in which $R^\alpha$ is cyclopropyl, $R^\beta$ is cyclopropyl, $R^1$ is methoxy and for each compound the combination of the radicals $R^2$ and $R^3$ corresponds to one row of Table D Table 346
Compounds of the formula IB.4", in which $R^\alpha$ is cyclopropyl, $R^\beta$ is cyclopropyl, $R^1$ is methyl and for each compound the combination of the radicals $R^2$ and $R^3$ corresponds to one row of Table D Table 347
Compounds of the formula IB.4", in which $R^\alpha$ is cyclopropyl, $R^\beta$ is cyclopropyl, $R^1$ is methoxy and for each compound the combination of the radicals $R^2$ and $R^3$ corresponds to one row of Table D Table 348
Compounds of the formula IB.5", in which $R^\alpha$ is cyclopropyl, $R^\beta$ is cyclopropyl and for each compound W corresponds to one row of Table C Table 349
Compounds of the formula IB.6', in which $R^\alpha$ is cyclopropyl, $R^\beta$ is cyclopropyl and for each compound W corresponds to one row of Table C Table 350
Compounds of the formula IB.6", in which $R^\alpha$ is cyclopropyl, $R^\beta$ is cyclopropyl and for each compound W corresponds to one row of Table C Table 351
Compounds of the formula IB.7', in which $R^\alpha$ is cyclopropyl, $R^\beta$ is cyclopropyl and for each compound W corresponds to one row of Table C Table 352
Compounds of the formula IB.1', in which $R^\alpha$ is cyclopropyl, $R^\beta$ is benzyl and for each compound Z corresponds to one row of Table A Table 353
Compounds of the formula IB.1", in which $R^\alpha$ is cyclopropyl, $R^\beta$ is benzyl and for each compound Z corresponds to one row of Table B Table 354
Compounds of the formula IB.2', in which $R^\alpha$ is cyclopropyl, $R^\beta$ is benzyl and for each compound Z corresponds to one row of Table B Table 355
Compounds of the formula IB.3', in which $R^\alpha$ is cyclopropyl, $R^\beta$ is benzyl, $R^1$ is methyl and for each compound W corresponds to one row of Table C Table 356
Compounds of the formula IB.3", in which $R^\alpha$ is cyclopropyl, $R^\beta$ is benzyl, $R^1$ is methyl and for each compound W corresponds to one row of Table C Table 357
Compounds of the formula IB.4', in which $R^\alpha$ is cyclopropyl, $R^\beta$ is benzyl, $R^1$ is methyl and for each compound the combination of the radicals $R^2$ and $R^3$ corresponds to one row of Table D Table 358
Compounds of the formula IB.4', in which $R^\alpha$ is cyclopropyl, $R^\beta$ is benzyl, $R^1$ is methoxy and for each compound the combination of the radicals $R^2$ and $R^3$ corresponds to one row of Table D Table 359
Compounds of the formula IB.4", in which $R^\alpha$ is cyclopropyl, $R^\beta$ is benzyl, $R^1$ is methyl and for each compound the combination of the radicals $R^2$ and $R^3$ corresponds to one row of Table D Table 360
Compounds of the formula IB.4", in which $R^\alpha$ is cyclopropyl, $R^\beta$ is benzyl, $R^1$ is methoxy and for each compound the combination of the radicals $R^2$ and $R^3$ corresponds to one row of Table D Table 361
Compounds of the formula IB.5", in which $R^\alpha$ is cyclopropyl, $R^\beta$ is benzyl and for each compound W corresponds to one row of Table C Table 362
Compounds of the formula IB.6', in which $R^\alpha$ is cyclopropyl, $R^\beta$ is benzyl and for each compound W corresponds to one row of Table C Table 363
Compounds of the formula IB.6", in which $R^\alpha$ is cyclopropyl, $R^\beta$ is benzyl and for each compound W corresponds to one row of Table C Table 364
Compounds of the formula IB.7', in which $R^\alpha$ is cyclopropyl, $R^\beta$ is benzyl and for each compound W corresponds to one row of Table C

TABLE A

| No. | Z |
|---|---|
| A-1 | $C_6H_5$ |
| A-2 | 2-F—$C_6H_4$ |
| A-3 | 3-F—$C_6H_4$ |
| A-4 | 4-F—$C_6H_4$ |
| A-5 | 2-Cl—$C_6H_4$ |
| A-6 | 3-Cl—$C_6H_4$ |
| A-7 | 4-Cl—$C_6H_4$ |
| A-8 | 2-Br—$C_6H_4$ |
| A-9 | 3-Br—$C_6H_4$ |
| A-10 | 4-Br—$C_6H_4$ |
| A-11 | 2-$CH_3$—$C_6H_4$ |
| A-12 | 3-$CH_3$—$C_6H_4$ |
| A-13 | 4-$CH_3$—$C_6H_4$ |
| A-14 | 2-$CF_3$—$C_6H_4$ |
| A-15 | 3-$CF_3$—$C_6H_4$ |
| A-16 | 4-$CF_3$—$C_6H_4$ |
| A-17 | 2,3-$F_2$—$C_6H_3$ |
| A-18 | 2,4-$F_2$—$C_6H_3$ |
| A-19 | 2,5-$F_2$—$C_6H_3$ |
| A-20 | 2,6-$F_2$—$C_6H_3$ |
| A-21 | 3,4-$F_2$—$C_6H_3$ |
| A-22 | 3,5-$F_2$—$C_6H_3$ |
| A-23 | 2,4-$Cl_2$—$C_6H_3$ |
| A-24 | 2,5-$Cl_2$—$C_6H_3$ |
| A-25 | 3,4-$Cl_2$—$C_6H_3$ |
| A-26 | 3,5-$Cl_2$—$C_6H_3$ |
| A-27 | 2-F-4-Cl—$C_6H_3$ |
| A-28 | 2-F-5-Cl—$C_6H_3$ |
| A-29 | 2-Cl-4-$CH_3$—$C_6H_3$ |
| A-30 | 2-$CH_3$-4-Cl—$C_6H_3$ |
| A-31 | 2-$CH_3$-5-Cl—$C_6H_3$ |
| A-32 | 2-Cl-5-$CH_3$—$C_6H_3$ |
| A-33 | 2,4-$(CH_3)_2$—$C_6H_3$ |
| A-34 | 2,5-$(CH_3)_2$—$C_6H_3$ |
| A-35 | 3,5-$(CH_3)_2$—$C_6H_3$ |
| A-36 | 2,3,5-$(CH_3)_3$—$C_6H_2$ |
| A-37 | 2,4,5-$(CH_3)_3$—$C_6H_2$ |
| A-38 | 2-$CH_3$-4-isopropyl-$C_6H_3$ |
| A-39 | 2-$CH_3$-4-tert-butyl-$C_6H_3$ |
| A-40 | 2-$CH_3$-4-phenyl-$C_6H_3$ |
| A-41 | 2-$CH_3$-5-phenyl-$C_6H_3$ |
| A-42 | 3-OH—$C_6H_4$ |
| A-43 | 2-$CH_3$-4-OH—$C_6H_3$ |
| A-44 | 2-$CH_3$-5-OH—$C_6H_3$ |
| A-45 | 3-$OCH_3$—$C_6H_4$ |
| A-46 | 4-$OCH_3$—$C_6H_4$ |
| A-47 | 3-$OC_2H_5$—$C_6H_4$ |
| A-48 | 4-$OC_2H_5$—$C_6H_4$ |
| A-49 | 2-$CH_3$-4-$OCH_3$—$C_6H_3$ |
| A-50 | 2-$CH_3$-4-$OC_2H_5$—$C_6H_3$ |
| A-51 | 2-$CH_3$-4-O-n-propyl-$C_6H_3$ |
| A-52 | 2-$CH_3$-4-O-n-butyl-$C_6H_3$ |
| A-53 | 2-$CH_3$-4-O-phenyl-$C_6H_3$ |
| A-54 | 3-O-phenyl-$C_6H_4$ |
| A-55 | 4-O-phenyl-$C_6H_4$ |
| A-56 | 1-naphthyl |
| A-57 | 2-naphthyl |
| A-58 | 3-$COCH_3$—$C_6H_4$ |
| A-59 | 4-$COCH_3$—$C_6H_4$ |
| A-60 | 2-$CH_3$-4-$OCH_3$—$C_6H_3$ |
| A-61 | 2-$CH_3$-5-$COCH_3$—$C_6H_3$ |
| A-62 | 2-$CH_3$-4-CHO—$C_6H_3$ |

TABLE A-continued

| No. | Z |
|---|---|
| A-63 | 2-$CH_3$-5-CHO—$C_6H_3$ |
| A-64 | 3-CHO—$C_6H_4$ |
| A-65 | 2-Cl-4-$COCH_3$—$C_6H_3$ |
| A-66 | 2,5-$(CH_3)_2$-4-$COCH_3$—$C_6H_2$ |
| A-67 | 2-$CH_3$-5-Cl-4-$COCH_3$—$C_6H_2$ |
| A-68 | 3-(2-F—$OC_6H_4$)—$C_6H_4$ |
| A-69 | 3-(2-$CH_3$—$OC_6H_4$)—$C_6H_4$ |
| A-70 | 3-(2-Cl—$OC_6H_4$)—$C_6H_4$ |
| A-71 | 3-(2-CN—$OC_6H_4$)—$C_6H_4$ |
| A-72 | 3-(2-$CO_2CH_3$—$OC_6H_4$)—$C_6H_4$ |
| A-73 | 3-(2,4-$F_2$—$OC_6H_3$)—$C_6H_4$ |
| A-74 | 3-(2,6-$F_2$—$OC_6H_3$)—$C_6H_4$ |
| A-75 | 3-(2,5-$F_2$—$OC_6H_3$)—$C_6H_4$ |
| A-76 | 3-(2,6-$Cl_2$—$OC_6H_3$)—$C_6H_4$ |
| A-77 | 3-(2,4-$Cl_2$—$OC_6H_3$)—$C_6H_4$ |
| A-78 | 3-[2,4-$(CH_3)_2$—$OC_6H_3$]—$C_6H_4$ |
| A-79 | 3-[2,6-$(CH_3)_2$—$OC_6H_3$]—$C_6H_4$ |
| A-80 | 3-(3-F—$OC_6H_4$)—$C_6H_4$ |
| A-81 | 3-(3-Cl—$OC_6H_4$)—$C_6H_4$ |
| A-82 | 3-(3-$CH_3$—$OC_6H_4$)—$C_6H_4$ |
| A-83 | 3-(4-F—$OC_6H_4$)—$C_6H_4$ |
| A-84 | 3-(4-Cl—$OC_6H_4$)—$C_6H_4$ |
| A-85 | 3-(4-$CH_3$—$OC_6H_4$)—$C_6H_4$ |
| A-86 | 3-(3-isopropyl-$OC_6H_4$)—$C_6H_4$ |
| A-87 | 3-(3-tert-butyl-$OC_6H_4$)—$C_6H_4$ |
| A-88 | 3-(4-isopropyl-$OC_6H_4$)—$C_6H_4$ |
| A-89 | 3-(4-tert-butyl-$OC_6H_4$)—$C_6H_4$ |
| A-90 | pyridin-2-yl |
| A-91 | 3-fluoropyridin-2-yl |
| A-92 | 3-chloropyridin-2-yl |
| A-93 | 3-bromopyridin-2-yl |
| A-94 | 3-methylpyridin-2-yl |
| A-95 | 3-trifluoromethylpyridin-2-yl |
| A-96 | 3-methoxypyridin-2-yl |
| A-97 | 4-fluoropyridin-2-yl |
| A-98 | 4-chloropyridin-2-yl |
| A-99 | 4-bromopyridin-2-yl |
| A-100 | 4-methylpyridin-2-yl |
| A-101 | 4-trifluoromethylpyridin-2-yl |
| A-102 | 4-methoxypyridin-2-yl |
| A-103 | 5-fluoropyridin-2-yl |
| A-104 | 5-chloropyridin-2-yl |
| A-105 | 5-bromopyridin-2-yl |
| A-106 | 5-methylpyridin-2-yl |
| A-107 | 5-methoxypyridin-2-yl |
| A-108 | 6-fluoropyridin-2-yl |
| A-109 | 6-chloropyridin-2-yl |
| A-110 | 6-bromopyridin-2-yl |
| A-111 | 6-methylpyridin-2-yl |
| A-112 | 6-trifluoromethylpyridin-2-yl |
| A-113 | 6-methoxypyridin-2-yl |
| A-114 | 3-fluoro-5-trifluoromethylpyridin-2-yl |
| A-115 | 3,6-dichloro-5-trifluoromethylpyridin-2-yl |
| A-116 | 5,6-dichloro-3-trifluoromethylpyridin-2-yl |
| A-117 | 5-chloro-3-trifluoromethylpyridin-2-yl |
| A-118 | 3-chloro-5-trifluoromethylpyridin-2-yl |
| A-119 | 6-chloro-4-cyanopyridin-2-yl |
| A-120 | 3-cyano-5-nitropyridin-2-yl |
| A-121 | 2-chloro-6-fluoropyridin-4-yl |
| A-122 | 6-chloro-4-fluoropyridin-2-yl |
| A-123 | 4,6-difluoropyridin-2-yl |
| A-124 | 3,5-dichloro-6-fluoropyridin-2-yl |
| A-125 | 6-methoxy-3-nitropyridin-2-yl |
| A-126 | 4-cyano-6-fluoropyridin-2-yl |
| A-127 | 6-chloro-5-cyanopyridin-2-yl |
| A-128 | 6-chloro-3-cyanopyridin-2-yl |
| A-129 | 4-cyano-3,5,6-trifluoropyridin-2-yl |
| A-130 | 6-chloro-6-nitropyridin-2-yl |
| A-131 | 6-chloro-3-nitropyridin-2-yl |
| A-132 | 5-cyano-6-fluoropyridin-2-yl |
| A-133 | 3-cyano-6-fluoropyridin-2-yl |
| A-134 | 4,6-dicyanopyridin-2-yl |
| A-135 | 5-trichloromethylpyridin-2-yl |
| A-136 | 5-cyanopyridin-2-yl |
| A-137 | 5-bromo-4-trifluoromethylpyridin-2-yl |
| A-138 | 3-nitro-5-trifluoromethylpyridin-2-yl |
| A-139 | 5-formamidopyridin-2-yl |

TABLE A-continued

| No. | Z |
|---|---|
| A-140 | 5-aminopyridin-2-yl |
| A-141 | 5-nitropyridin-2-yl |
| A-142 | 4-methyl-5-nitropyridin-2-yl |
| A-143 | 5-difluoromethylpyridin-2-yl |
| A-144 | 5-fluoromethylpyridin-2-yl |
| A-145 | 5-methoxycarbonylpyridin-2-yl |
| A-146 | 5-chloro-6-fluoropyridin-2-yl |
| A-147 | 5-chloro-6-hydroxypyridin-2-yl |
| A-148 | 5-chloro-6-methoxypyridin-2-yl |
| A-149 | 5-chloro-6-cyanopyridin-2-yl |
| A-150 | 5,6-dichloropyridin-2-yl |
| A-151 | 6-bromo-5-chloropyridin-2-yl |
| A-152 | 5-chloro-6-acetoxypyridin-2-yl |
| A-153 | 5-bromo-6-fluoropyridin-2-yl |
| A-154 | 5-bromo-6-chloropyridin-2-yl |
| A-155 | 5-bromo-6-cyanopyridin-2-yl |
| A-156 | 5-bromo-6-hydroxypyridin-2-yl |
| A-157 | 5-bromo-6-methoxypyridin-2-yl |
| A-158 | 5,6-dibromopyridin-2-yl |
| A-159 | 4-cyanopyridin-2-yl |
| A-160 | 6-cyanopyridin-2-yl |
| A-161 | 5-chloropyridin-2-yl |
| A-162 | 5-chloropyridin-2-yl |
| A-163 | 4-chloro-6-methylpyrimidin-2-yl |
| A-164 | 5-bromo-4-trifluoromethylpyridin-2-yl |
| A-165 | 4,5-dichloropyridin-2-yl |
| A-166 | 4,5-dibromopyridin-2-yl |
| A-167 | 5,6-dichloropyridin-2-yl |
| A-168 | 4,6-dichloropyridin-2-yl |
| A-169 | 4,6-dibromopyridin-2-yl |
| A-170 | 5,6-dibromopyridin-2-yl |
| A-171 | 4-bromo-5-chloropyridin-2-yl |
| A-172 | 6-bromo-5-chloropyridin-2-yl |
| A-173 | 5-bromo-4-chloropyridin-2-yl |
| A-174 | 5-bromo-4-chloropyridin-2-yl |
| A-175 | 6-bromo-4-chloropyridin-2-yl |
| A-176 | 4-bromo-6-chloropyridin-2-yl |
| A-177 | 6-chloro-4-tnethoxypyridin-2-yl |
| A-178 | 6-bromo-4-methoxypyridin-2-yl |
| A-179 | 5-butyloxycarbonylpyridin-2-yl |
| A-180 | 4-formylpyridin-2-yl |
| A-181 | 5-formylpyridin-2-yl |
| A-182 | 6-formylpyridin-2-yl |
| A-183 | 4-cyanopyridin-2-yl |
| A-184 | 6-cyanopyridin-2-yl |
| A-185 | 5-propoxycarbonylpyridin-2-yl |
| A-186 | 6-chloro-4-trifluoromethylpyridin-2-yl |
| A-187 | 6-chloro-4-trifluoromethylpyridin-2-yl |
| A-188 | 6-chloro-4-methylpyridin-2-yl |
| A-189 | 2,5-dichloro-6-cyanopyridin-2-yl |
| A-190 | 2,5-dichloro-6-carboxypyridin-2-yl |
| A-191 | 2,5-dichloro-6-methoxycarbonyl-pyridin-2-yl |
| A-192 | 4-cyanopyridin-2-yl |
| A-193 | 6-trifluoromethylpyridin-2-yl |
| A-194 | 6-methoxycarbonylpyridin-2-yl |
| A-195 | 6-carboxypyridin-2-yl |
| A-196 | 4-phenoxypyridin-2-yl |
| A-197 | 5-phenoxypyridin-2-yl |
| A-198 | 6-phenoxypyridin-2-yl |
| A-199 | pyridin-3-yl |
| A-200 | 2-fluoropyridin-3-yl |
| A-201 | 2-chloropyridin-3-yl |
| A-202 | 2-bromopyridin-3-yl |
| A-203 | 2-methylpyridin-3-yl |
| A-204 | 2-trifluoromethylpyridin-3-yl |
| A-205 | 3-methoxypyridin-3-yl |
| A-206 | 4-fluoropyridin-3-yl |
| A-207 | 4-chloropyridin-3-yl |
| A-208 | 4-bromopyridin-3-yl |
| A-209 | 4-methylpyridin-3-yl |
| A-210 | 4-trifluoromethylpyridin-3-yl |
| A-211 | 4-methoxypyridin-3-yl |
| A-212 | 5-fluoropyridin-3-yl |
| A-213 | 5-chloropyridin-3-yl |
| A-214 | 5-bromopyridin-3-yl |
| A-215 | 5-methylpyridin-3-yl |
| A-216 | 5-trifluoromethylpyridin-3-yl |
| A-217 | 5-methoxypyridin-3-yl |
| A-218 | 6-fluoropyridin-3-yl |
| A-219 | 6-chloropyridin-3-yl |
| A-220 | 6-bromopyridin-3-yl |
| A-221 | 6-methylpyridin-3-yl |
| A-222 | 6-trifluoromethylpyridin-3-yl |
| A-223 | 6-methoxypyridin-3-yl |
| A-224 | 6-chloropyridin-3-yl |
| A-225 | pyridin-4-yl |
| A-226 | 2-fluoropyridin-4-yl |
| A-227 | 2-chloropyridin-4-yl |
| A-228 | 2-bromopyridin-4-yl |
| A-229 | 2-methylpyridin-4-yl |
| A-230 | 2-trifluoromethylpyridin-4-yl |
| A-231 | 2-methoxypyridin-4-yl |
| A-232 | 3-fluoropyridin-4-yl |
| A-233 | 3-chloropyridin-4-yl |
| A-234 | 3-bromopyridin-4-yl |
| A-235 | 3-methylpyridin-4-yl |
| A-236 | 3-trifluoromethylpyridin-4-yl |
| A-237 | 3-methoxypyridin-4-yl |
| A-238 | 2,3,5,6-tetrafluoropyridin-4-yl |
| A-239 | 2-choro-6-fluoropyridin-4-yl |
| A-240 | 4-fluoropyrimidin-2-yl |
| A-241 | 4-chloropyrimidin-2-yl |
| A-242 | 4-bromopyrimidin-2-yl |
| A-243 | 4-methylpyrimidin-2-yl |
| A-244 | 4-trifluoromethylpyrimidin-2-yl |
| A-245 | 4-methoxypyrimidin-2-yl |
| A-246 | 5-fluoropyrimidin-2-yl |
| A-247 | 5-chloropyrimidin-2-yl |
| A-248 | 5-bromopyrimidin-2-yl |
| A-249 | 5-methylpyrimidin-2-yl |
| A-250 | 5-trifluoromethylpyrimidin-2-yl |
| A-251 | 5-methoxypyrimidin-2-yl |
| A-252 | 4,6-difluoropyrimidin-2-yl |
| A-253 | 4-phenoxypyrimidin-2-yl |
| A-254 | 4-(2-fluorophenoxy)-pyrimidin-2-yl |
| A-255 | 2-fluoropyrimidin-4-yl |
| A-256 | 2-chloropyrimidin-4-yl |
| A-257 | 2-bromopyrimidin-4-yl |
| A-258 | 2-methylpyrimidin-4-yl |
| A-259 | 2-trifluoromethylpyrimidin-4-yl |
| A-260 | 2-methoxypyrimidin-4-yl |
| A-261 | 5-fluoropyrimidin-4-yl |
| A-262 | 5-chloropyrimidin-4-yl |
| A-263 | 5-bromopyrimidin-4-yl |
| A-264 | 5-methoxypyrimidin-4-yl |
| A-265 | 5-trifluoromethylpyrimidin-4-yl |
| A-266 | 5-methoxypyrimidin-4-yl |
| A-267 | 6-fluoropyrimidin-4-yl |
| A-268 | 6-chloropyrimidin-4-yl |
| A-269 | 6-bromopyrimidin-4-yl |
| A-270 | 6-methylpyrimidin-4-yl |
| A-271 | 6-trifluoromethylpyrimidin-4-yl |
| A-272 | 6-methoxypyrimidin-4-yl |
| A-273 | 2,6-difluoropyrimidin-4-yl |
| A-274 | 2-chloro-6-trichloromethylpyrimidin-4-yl |
| A-275 | 2,6-dichloropyrimidin-4-yl |
| A-276 | 2-fluoropyrimidin-5-yl |
| A-277 | 2-chloropyrimidin-5-yl |
| A-278 | 2-bromopyrimidin-5-yl |
| A-279 | 2-methylpyrimidin-5-yl |
| A-280 | 2-trifluoromethylpyrimidin-5-yl |
| A-281 | 2-methoxypyrimidin-5-yl |
| A-282 | 4-fluoropyrimidin-5-yl |
| A-283 | 4-chloropyrimidin-5-yl |
| A-284 | 4-bromopyrimidin-5-yl |
| A-285 | 4-methylpyrimidin-5-yl |
| A-286 | 4-trifluoromethylpyrimidin-5-yl |
| A-287 | 6-chloroquinazolin-2-yl |
| A-288 | quinazolin-2-yl |
| A-289 | 2-furanyl |
| A-290 | 3-furanyl |
| A-291 | 4-chloro-2-thienyl |
| A-292 | 5-chloro-2-thienyl |
| A-293 | 5-bromo-2-thienyl |

TABLE A-continued

| No. | Z |
|---|---|
| A-294 | 5-nitro-2-thienyl |
| A-295 | 3-thienyl |
| A-296 | 2-chloro-3-thienyl |
| A-297 | 2-bromo-3-thienyl |
| A-298 | 1-methyl-3-pyrrolyl |
| A-299 | 1-methyl-2-pyrrolyl |
| A-300 | 1-benzofuran-2-yl |
| A-301 | 1-benzofuran-3-yl |
| A-302 | 1-benzothiophen-2-yl |
| A-303 | 1-benzothiophen-3-yl |
| A-304 | 3-pyrrolyl |
| A-305 | 2-pyrrolyl |
| A-306 | 3-indolyl |
| A-307 | 2-indolyl |
| A-308 | 1-methyl-3-indolyl |
| A-309 | 1-methyl-2-indolyl |
| A-310 | 1-methylpyrazol-4-yl |
| A-311 | 1-phenylpyrazol-4-yl |
| A-312 | 1-methylpyrazol-5-yl |
| A-313 | isoxazol-3-yl |
| A-314 | isoxazol-4-yl |
| A-315 | isoxazol-5-yl |
| A-316 | isothiazol-3-yl |
| A-317 | isothiazol-4-yl |
| A-318 | isothiazol-5-yl |
| A-319 | oxazol-2-yl |
| A-320 | oxazol-5-yl |
| A-321 | oxazol-4-yl |
| A-322 | thiazol-4-yl |
| A-323 | thiazol-5-yl |
| A-324 | thiazol-2-yl |
| A-325 | 1-methylimidazol-4-yl |
| A-326 | 1-methylimidazol-5-yl |
| A-327 | 1-methylimidazol-2-yl |
| A-328 | 1,2-benzisoxazol-3-yl |
| A-329 | 1,2-benzisothiazol-3-yl |
| A-330 | 1-methylindazol-3-yl |
| A-331 | benzoxazol-2-yl |
| A-332 | 5-chlorobenzoxazol-2-yl |
| A-333 | 6-fluorobenzoxazol-2-yl |
| A-334 | benzothiazol-2-yl |
| A-335 | 5-fluorobenzothiazol-2-yl |
| A-336 | 6-fluorobenzothiazol-2-yl |
| A-337 | pyrido[3,2-d]thiazol-2-yl |
| A-338 | (6-chloro-pyrido)[3,2-d]thiazol-2-yl |
| A-339 | 1-methyl-1,2,3-triazol-5-yl |
| A-340 | 1-methyl-1,2,3-triazol-4-yl |
| A-341 | 1-methyl-1,3,4-triazol-5-yl |
| A-342 | 1-methyl-1,3,4-triazol-3-yl |
| A-343 | 1-methyl-1,2,3,4-tetrazol-5-yl |
| A-344 | 2-methyl-1,2,3,4-tetrazol-5-yl |
| A-345 | 5-trifluoromethyl-1,3,4-thiadiazol-2-yl |
| A-346 | 6-chlorobenzoxazol-2-yl |
| A-347 | 5-fluorobenzoxazol-2-yl |
| A-348 | 5-nitrothiazol-2-yl |

TABLE B

| No. | Z |
|---|---|
| B-1 | $C_6H_5$ |
| B-2 | 2-F—$C_6H_4$ |
| B-3 | 3-F—$C_6H_4$ |
| B-4 | 4-F—$C_6H_4$ |
| B-5 | 2-Cl—$C_6H_4$ |
| B-6 | 3-Cl—$C_6H_4$ |
| B-7 | 4-Cl—$C_6H_4$ |
| B-8 | 2-$CH_3$—$C_6H_4$ |
| B-9 | 3-$CH_3$—$C_6H_4$ |
| B-10 | 4-$CH_3$—$C_6H_4$ |
| B-11 | 2-$CF_3$—$C_6H_4$ |
| B-12 | 3-$CF_3$—$C_6H_4$ |
| B-13 | 4-$CF_3$—$C_6H_4$ |
| B-14 | 2,4-$(CH_3)_2$—$C_6H_3$ |

TABLE B-continued

| No. | Z |
|---|---|
| B-15 | 2,5-$(CH_3)_2$—$C_6H_3$ |
| B-16 | 3,5-$(CH_3)_2$—$C_6H_3$ |
| B-17 | 2,4-$Cl_2$—$C_6H_3$ |
| B-18 | 2,5-$Cl_2$—$C_6H_3$ |
| B-19 | 3,4-$Cl_2$—$C_6H_3$ |
| B-20 | 3,5-$Cl_2$—$C_6H_3$ |
| B-21 | 2,4-$F_2$—$C_6H_3$ |
| B-22 | 2-F-4-Cl—$C_6H_3$ |
| B-23 | 2-F-5-Cl—$C_6H_3$ |
| B-24 | 2-Cl-4-$CH_3$—$C_6H_3$ |
| B-25 | 2-$CH_3$-4-Cl—$C_6H_3$ |
| B-26 | 2-$CH_3$-5-Cl—$C_6H_3$ |
| B-27 | 2-Cl-5-$CH_3$—$C_6H_3$ |
| B-28 | 2,3,5-$(CH_3)_3$—$C_6H_2$ |
| B-29 | 2,4,5-$(CH_3)_3$—$C_6H_2$ |
| B-30 | 2-$CH_3$-4-isopropyl-$C_6H_3$ |
| B-31 | 2-$CH_3$-4-tert-butyl-$C_6H_3$ |
| B-32 | 2-$CH_3$-4-phenyl-$C_6H_3$ |
| B-33 | 2-$CH_3$-5-phenyl-$C_6H_3$ |
| B-34 | 3-OH—$C_6H_4$ |
| B-35 | 2-$CH_3$-4-OH—$C_6H_3$ |
| B-36 | 2-$CH_3$-5-OH—$C_6H_3$ |
| B-37 | 3-$OCH_3$—$C_6H_4$ |
| B-38 | 4-$OCH_3$—$C_6H_4$ |
| B-39 | 3-$OCH_2CH_3$—$C_6H_4$ |
| B-40 | 4-$OCH_2CH_3$—$C_6H_4$ |
| B-41 | 2-$CH_3$-4-$OCH_3$—$C_6H_3$ |
| B-42 | 2-$CH_3$-4-$OC_2H_5$—$C_6H_3$ |
| B-43 | 2-$CH_3$-4-O-n-propyl-$C_6H_3$ |
| B-44 | 2-$CH_3$-4-O-n-butyl-$C_6H_3$ |
| B-45 | 2-$CH_3$-4-O-phenyl-$C_6H_3$ |
| B-46 | 3-O-phenyl-$C_6H_4$ |
| B-47 | 4-O-phenyl-$C_6H_4$ |
| B-48 | 3-$COCH_3$—$C_6H_4$ |
| B-49 | 4-$COCH_3$—$C_6H_4$ |
| B-50 | 2-$CH_3$-4-$OCH_3$—$C_6H_3$ |
| B-51 | 2-$CH_3$-5-$COCH_3$—$C_6H_3$ |
| B-52 | 2-$CH_3$-4-CHO—$C_6H_3$ |
| B-53 | 2-$CH_3$-5-CHO—$C_6H_3$ |
| B-54 | 3-CHO—$C_6H_4$ |
| B-55 | 2-Cl-4-$COCH_3$—$C_6H_3$ |
| B-56 | 2,5-$(CH_3)_2$-4-$COCH_3$—$C_6H_2$ |
| B-57 | 2-$CH_3$-5-Cl-4-$COCH_3$—$C_6H_2$ |
| B-58 | 3-[C($CH_3$)=NOH]—$C_6H_4$ |
| B-59 | 3-[C($CH_3$)=$NOCH_3$]—$C_6H_4$ |
| B-60 | 3-[C($CH_3$)=$NOCH_2CH_3$]—$C_6H_4$ |
| B-61 | 3-[C($CH_3$)=$NOCH_2CH_2CH_3$]—$C_6H_4$ |
| B-62 | 3-[C($CH_3$)=$NOCH_2CH=CH_2$]—$C_6H_4$ |
| B-63 | 3-[C($CH_3$)=$NOCH_2C\equiv CH$]—$C_6H_4$ |
| B-64 | 2-$CH_3$-4-[C($CH_3$)=$NOCH_3$]—$C_6H_3$ |
| B-65 | 2-$CH_3$-4-[C($CH_3$)=$NOCH_2CH_3$]—$C_6H_3$ |
| B-66 | 2-$CH_3$-4-[C($CH_3$)=$NOCH_2CH_2CH_3$]—$C_6H_3$ |
| B-67 | 2-$CH_3$-4-[C($CH_3$)=$NOCH_2CH=CH_2$]—$C_6H_3$ |
| B-68 | 2-$CH_3$-4-[C($CH_3$)=$NOCH_2$—$C\equiv CH$]—$C_6H_3$ |
| B-69 | 2,5-$(CH_3)_2$-4-[C($CH_3$)=$NOCH_3$]—$C_6H_2$ |
| B-70 | 2,5-$(CH_3)_2$-4-[C($CH_3$)=$NOCH_2CH_3$]—$C_6H_2$ |
| B-71 | 2,5-$(CH_3)_2$-4-[C($CH_3$)=$NOCH_2CH_2CH_3$]—$C_6H_2$ |
| B-72 | 2,5-$(CH_3)_2$-4-[C($CH_3$)=$NOCH_2CH=CH_2$]—$C_6H_2$ |
| B-73 | 2,5-$(CH_3)_2$-4-[C($CH_3$)=$NOCH_2$—$C\equiv CH$]—$C_6H_2$ |
| B-74 | 2-$CH_3$-5-[C($CH_3$)=$NOCH_3$]—$C_6H_3$ |
| B-75 | 2-$CH_3$-5-[C($CH_3$)=$NOCH_2CH_3$]—$C_6H_3$ |
| B-76 | 2-$CH_3$-5-[C($CH_3$)$NOCH_2CH_2CH_3$]—$C_6H_5$ |
| B-77 | 2-$CH_3$-5-[C($CH_3$)=$NOCH_2=CH=CH_2$]—$C_6H_2$ |
| B-78 | 2-$CH_3$-5-[C($CH_3$)=$NOCH_2C\equiv CH$]—$C_6H_3$ |
| B-79 | 2-$CH_3$-5-Cl-4-[C($CH_3$)=$NOCH_2$]—$C_6H_2$ |
| B-80 | 2-$CH_3$-4-[C($CH_2CH_3$)=$NOCH_3$]—$C_6H_3$ |
| B-81 | 2-$CH_3$-4-[C($CH_2CH_3$)=$NOCH_2CH_3$]—$C_6H_3$ |
| B-82 | 1-naphthyl |
| B-83 | 2-naphthyl |
| B-84 | 2-pyridyl |
| B-85 | 5-methyl-2-pyridyl |
| B-86 | 6-methyl-2-pyridyl |
| B-87 | 6-n-propyl-2-pyridyl |
| B-88 | 6-n-butyl-2-pyridyl |
| B-89 | 6-tert-butyl-2-pyridyl |
| B-90 | 6-n-pentyl-2-pyridyl |
| B-91 | 6-n-hexyl-2-pyridyl |

TABLE B-continued

| No. | Z |
|---|---|
| B-92 | 6-phenyl-2-pyridyl |
| B-93 | 6-benzyl-2-pyridyl |
| B-94 | 6-trifluoromethyl-2-pyridyl |
| B-95 | 6-methoxy-2-pyridyl |
| B-96 | 6-chloro-2-pyridyl |
| B-97 | 3-fluoro-2-pyridyl |
| B-98 | 3-chloro-2-pyridyl |
| B-99 | 4-bromo-2-pyridyl |
| B-100 | 6-bromo-2-pyridyl |
| B-101 | 3,6-dimethyl-2-pyridyl |
| B-102 | 3,6-diethyl-2-pyridyl |
| B-103 | 4,6-dimethyl-2-pyridyl |
| B-104 | 5,6-dimethyl-2-pyridyl |
| B-105 | 4-phenyl-6-methyl-2-pyridyl |
| B-106 | 4,6-diphenyl-2-pyridyl |
| B-107 | 3,4-dichloro-6-methyl-2-pyridyl |
| B-108 | 3,4,5-trichloro-6-phenyl-2-pyridyl |
| B-109 | 4-trifluoromethyl-6-methyl-2-pyridyl |
| B-110 | 3-acetyl-4,6-dimethyl-2-pyridyl |
| B-111 | 3-cyano-6-methyl-2-pyridyl |
| B-112 | 3-trifluoromethyl-2-pyridyl |
| B-113 | 5-trifluoromethyl-2-pyridyl |
| B-114 | 4,6-difluoro-2-pyridyl |
| B-115 | 3,5-dichloro-6-fluoro-2-pyridyl |
| B-116 | 3,4-dichloro-2-pyridyl |
| B-117 | 3,5-dichloro-2-pyridyl |
| B-118 | 3,6-dichloro-2-pyridyl |
| B-119 | 4,5-dichloro-2-pyridyl |
| B-120 | 4,6-dichloro-2-pyridyl |
| B-121 | 3,5,6-trichloro-2-pyridyl |
| B-122 | 3-chloro-5-trifluoromethyl-2-pyridyl |
| B-123 | 3-trifluoromethyl-5-fluoro-2-pyridyl |
| B-124 | 3-trifluoromethyl-5-chloro-2-pyridyl |
| B-125 | 3-trifluoromethyl-5-bromo-2-pyridyl |
| B-126 | 3-trifluoromethyl-5-methyl-2-pyridyl |
| B-127 | 3-methoxycarbonyl-6-isopropyl-2-pyridyl |
| B-128 | 6-cyclopropyl-2-pyridyl |
| B-129 | 4-trifluoromethyl-2-pyridyl |
| B-130 | 4-trifluoromethyl-5-chloro-2-pyridyl |
| B-131 | 4-tert-butyl-2-pyridyl |
| B-132 | 3,6-bis(trifluoromethyl)-2-pyridyl |
| B-133 | 5-trifluoromethyl-2-pyridyl |
| B-134 | 5-trichloromethyl-2-pyridyl |
| B-135 | 3-fluoro-5-trifluoromethyl-2-pyridyl |
| B-136 | 3,6-dichloro-5-trifluoromethyl-2-pyridyl |
| B-137 | 6-chloro-4-cyano-2-pyridyl |
| B-138 | 3-cyano-5-nitro-2-pyridyl |
| B-139 | 6-methoxy-3-nitro-2-pyridyl |
| B-140 | 4-cyano-6-fluoro-2-pyridyl |
| B-141 | 4-cyano-3,5,6-trifluoro-2-pyridyl |
| B-142 | 6-chloro-5-nitro-2-pyridyl |
| B-143 | 4,6-dicyano-2-pyridyl |
| B-144 | 5-cyano-2-pyridyl |
| B-145 | 5-bromo-4-trifluoromethyl-2-pyridyl |
| B-146 | 3-nitro-5-trifluoromethyl-2-pyridyl |
| B-147 | 5-amino-2-pyridyl |
| B-148 | 5-nitro-2-pyridyl |
| B-149 | 4-methyl-5-nitro-2-pyridyl |
| B-150 | 5-difluoromethyl-2-pyridyl |
| B-151 | 5-fluoromethyl-2-pyridyl |
| B-152 | 5-methoxycarbonyl-2-pyridyl |
| B-153 | 5-chloro-6-methoxy-2-pyridyl |
| B-154 | 5,6-dichloro-2-pyridyl |
| B-155 | 6-bromo-5-chloro-2-pyridyl |
| B-156 | 5-chloro-6-acetoxy-2-pyridyl |
| B-157 | 5-bromo-6-fluoro-2-pyridyl |
| B-158 | 5-bromo-6-cyano-2-pyridyl |
| B-159 | 5-bromo-6-hydroxy-2-pyridyl |
| B-160 | 5-bromo-6-methoxy-2-pyridyl |
| B-161 | 5,6-dibromo-2-pyridyl |
| B-162 | 6-phenoxy-2-pyridyl |
| B-163 | 4-phenyl-2-pyridyl |
| B-164 | 4-phenoxy-2-pyridyl |
| B-165 | 6-hydroxy-2-pyridyl |
| B-166 | 6-ethoxy-2-pyridyl |
| B-167 | 6-benzyloxy-2-pyridyl |
| B-168 | 4-benzyloxy-2-pyridyl |
| B-169 | 4,6-bis(trifluoromethyl)-2-pyridyl |
| B-170 | 6-formyl-2-pyridyl |
| B-171 | 6-amino-2-pyridyl |
| B-172 | 4-amino-2-pyridyl |
| B-173 | 4-carboxy-2-pyridyl |
| B-174 | 3-bromo-5-trifluoromethyl-2-pyridyl |
| B-175 | 6-methyl-3-nitro-2-pyridyl |
| B-176 | 3-nitro-2-pyridyl |
| B-177 | 3-methyl-5-trifluoromethyl-2-pyridyl |
| B-178 | 3-pyridyl |
| B-179 | 2-fluoro-3-pyridyl |
| B-180 | 4-trifluoromethyl-3-pyridyl |
| B-181 | 5-methyl-3-pyridyl |
| B-182 | 6-methoxy-3-pyridyl |
| B-183 | 4-cyano-2,5,6-trifluoro-3-pyridyl |
| B-184 | 4-pyridyl |
| B-185 | 2-chloro-4-pyridyl |
| B-186 | 3-trifluoromethyl-4-pyridyl |
| B-187 | 2-chloro-6-fluoro-4-pyridyl |
| B-188 | 2,3,5,6-tetrafluoro-4-pyridyl |
| B-189 | 2-pyrimidinyl |
| B-190 | 4,6-dimethyl-2-pyrimidinyl |
| B-191 | 4-trifluoromethyl-2-pyrimidinyl |
| B-192 | 4,5,6-trimethyl-2-pyrimidinyl |
| B-193 | 4-benzyl-6-methyl-2-pyrimidinyl |
| B-194 | 4-methyl-6-phenyl-2-pyrimidinyl |
| B-195 | 4,6-dimethyl-5-chloropyrimidinyl |
| B-196 | 4-fluoro-2-pyrimidinyl |
| B-197 | 5-methyl-2-pyrimidinyl |
| B-198 | 4,6-difluoro-2-pyrimidinyl |
| B-199 | 4-methyl-2-pyrimidinyl |
| B-200 | 4-pyrimidinyl |
| B-201 | 2,6-dimethyl-4-pyrimidinyl |
| B-202 | 2-n-propyl-6-methyl-4-pyrimidinyl |
| B-203 | 2,6-bis(trifluoromethyl)-4-pyrimidinyl |
| B-204 | 2-chloromethyl-6-methyl-4-pyrimidinyl |
| B-205 | 2-methyl-6-chloromethyl-4-pyrimidinyl |
| B-206 | 2-isopropyl-6-methyl-4-pyrimidinyl |
| B-207 | 2-isopropyl-6-chloromethyl-4-pyrimidinyl |
| B-208 | 2-cyclopropyl-6-chloromethyl-4-pyrimidinyl |
| B-209 | 2-cyclopropyl-6-methyl-4-pyrimidinyl |
| B-210 | 2-methyl-6-methoxymethyl-4-pyrimidinyl |
| B-211 | 2-isopropyl-6-methoxymethyl-4-pyrimidinyl |
| B-212 | 2-phenyl-4-pyrimidinyl |
| B-213 | 2,5-dimethyl-4-pyrimidinyl |
| B-214 | 2-methylthio-6-trifluoromethyl-4-pyrimidinyl |
| B-215 | 2-methylthio-5-chloro-6-trifluoromethyl-4-pyrimidinyl |
| B-216 | 2-methylthio-5-n-octyl-6-methyl-4-pyrimidinyl |
| B-217 | 2-methyl-6-trifluoromethyl-4-pyrimidinyl |
| B-218 | 2-n-propyl-6-trifluoromethyl-4-pyrimidinyl |
| B-219 | 2-isopropyl-6-trifluoromethyl-4-pyrimidinyl |
| B-220 | 2-n-propyl-6-methyl-4-pyrimidinyl |
| B-221 | 2-tert-butyl-6-trifluoromethyl-4-pyrimidinyl |
| B-222 | 2-methyl-5-chloro-6-trifluoromethyl-4-pyrimidinyl |
| B-223 | 2-n-propyl-5-chloro-6-trifluoromethyl-4-pyrimidinyl |
| B-224 | 2-isopropyl-5-chloro-6-trifluoromethyl-4-pyrimidinyl |
| B-225 | 2-tert-butyl-5-chloro-6-trifluoromethyl-4-pyrimidinyl |
| B-226 | 2-chloro-4-pyrimidinyl |
| B-227 | 5-methoxy-4-pyrimidinyl |
| B-228 | 6-trifluoromethyl-4-pyrimidinyl |
| B-229 | 2-chloro-6-trichloromethyl-4-pyrimidinyl |
| B-230 | 2,6-dichloro-4-pyrimidinyl |
| B-231 | 2-phenyl-6-trifluoromethyl-4-pyrimidinyl |
| B-232 | 2-methylthio-6-difluoromethoxy-4-pyrimidyl |
| B-233 | 2-ethyl-6-trifluoromethyl-4-pyrimidinyl |
| B-234 | 2-cyclopropyl-6-trifluoromethyl-4-pyrimidinyl |
| B-235 | 2-phenyl-6-trifluoromethyl-4-pyrimidinyl |
| B-236 | 2-methylthio-5-chloro-6-methoxy-4-pyrimidinyl |
| B-237 | 2-dimethylamino-5-n-butyl-6-methyl-4-pyrimidinyl |
| B-238 | 2-dimethylamino-5-nitro-6-methyl-4-pyrimidinyl |
| B-239 | 2-quinolyl |
| B-240 | 3-methyl-2-quinolyl |
| B-241 | 4-methyl-2-quinolyl |
| B-242 | 4-ethyl-2-quinolyl |
| B-243 | 4-phenyl-2-quinolyl |
| B-244 | 6-methyl-2-quinolyl |
| B-245 | 6-chloro-2-quinolyl |

TABLE B-continued

| No. | Z |
|---|---|
| B-246 | 8-methyl-2-quinolyl |
| B-247 | 8-chloro-2-quinolyl |
| B-248 | 4-ethoxycarbonyl-2-quinolyl |
| B-249 | 3,4-dimethyl-2-quinolyl |
| B-250 | 4-methyl-8-methoxy-2-quinolyl |
| B-251 | 4-phenyl-8-ethoxy-2-quinolyl |
| B-252 | 4-methyl-8-chloro-2-quinolyl |
| B-253 | 4-methyl-8-fluoro-2-quinolyl |
| B-254 | 4-quinolyl |
| B-255 | 2-methyl-4-quinolyl |
| B-256 | 2-trichloromethyl-4-quinolyl |
| B-257 | 2-trifluoromethyl-2-quinolyl |
| B-258 | 2-isopropyl-4-quinolyl |
| B-259 | 2-n-pentyl-4-quinolyl |
| B-260 | 2-phenyl-4-quinolyl |
| B-261 | 2-methoxycarbonyl-4-quinolyl |
| B-262 | 2,6-dimethyl-4-quinolyl |
| B-263 | 2-methyl-6-chloro-4-quinolyl |
| B-264 | 8-quinolyl |
| B-265 | 2-methyl-8-quinolyl |
| B-266 | 5,7-dichloro-8-quinolyl |
| B-267 | 2-pyrazinyl |
| B-268 | 6-chloro-2-pyrazinyl |
| B-269 | 5-methyl-2-pyrazinyl |
| B-270 | 3-pyradiazinyl |
| B-271 | 5-chloro-3-pyridazinyl |
| B-272 | 2-thienyl |
| B-273 | 3-thienyl |
| B-274 | 4-chloro-3-thienyl |
| B-275 | 2-chloro-3-thienyl |
| B-276 | 5-chloro-3-thienyl |
| B-277 | 4-chloro-2-thienyl |
| B-278 | 5-chloro-2-thienyl |
| B-279 | 2-quinoxalinyl |
| B-280 | 3-methyl-2-quinoxalinyl |
| B-281 | 7,8-dimethyl-2-quinoxalinyl |
| B-282 | 7,8-dichloro-2-quinoxalinyl |
| B-283 | 7-methyl-2-quinoxalinyl |
| B-284 | 8-methyl-2-quinoxalinyl |
| B-285 | 7-methoxy-2-quinoxalinyl |
| B-286 | 3-phenyl-5-isoxazolyl |
| B-287 | 2-benzoxazolyl |
| B-288 | 2-benzothiazolyl |
| B-289 | pyrazol-1-yl |
| B-290 | 4-chloropyrazol-1-yl |
| B-291 | 1-phenylpyrazol-4-yl |

TABLE C

| No. | W |
|---|---|
| C-1 | phenyl |
| C-2 | 2-fluorophenyl |
| C-3 | 3-fluorophenyl |
| C-4 | 4-fluorophenyl |
| C-5 | 2,3-difluorophenyl |
| C-6 | 2,4-difluorophenyl |
| C-7 | 2,5-difluorophenyl |
| C-8 | 2,6-difluorophenyl |
| C-9 | 3,4-difluorophenyl |
| C-10 | 3,5-difluorophenyl |
| C-11 | pentafluorophenyl |
| C-12 | 2-chlorophenyl |
| C-13 | 3-chlorophenyl |
| C-14 | 4-chlorophenyl |
| C-15 | pentachlorophenyl |
| C-16 | 2,3-dichlorophenyl |
| C-17 | 2,4-dichlorophenyl |
| C-18 | 2,5-dichlorophenyl |
| C-19 | 2,6-dichlorophenyl |
| C-20 | 3,4-dichlorophenyl |
| C-21 | 3,5-dichlorophenyl |
| C-22 | 2,3,4-trichlorophenyl |
| C-23 | 2,3,5-trichlorophenyl |

TABLE C-continued

| No. | W |
|---|---|
| C-24 | 2,3,6-trichlorophenyl |
| C-25 | 2-cyanophenyl |
| C-26 | 3-cyanophenyl |
| C-27 | 4-cyanophenyl |
| C-28 | 2-nitrophenyl |
| C-29 | 3-nitrophenyl |
| C-30 | 4-nitrophenyl |
| C-31 | 2-methylphenyl |
| C-32 | 3-methylphenyl |
| C-33 | 4-methylphenyl |
| C-34 | 2,4-dimethylphenyl |
| C-35 | 2,6-dimethylphenyl |
| C-36 | 3,4-dimethylphenyl |
| C-37 | 3,5-dimethylphenyl |
| C-38 | 2,3,4-trimethylphenyl |
| C-39 | 2,3,5-trimethylphenyl |
| C-40 | 2,3,6-trimethylphenyl |
| C-41 | 2,4,5-trimethylphenyl |
| C-42 | 2,4,6-trimethylphenyl |
| C-43 | 3,4,5-trimethylphenyl |
| C-44 | 2-ethylphenyl |
| C-45 | 3-ethylphenyl |
| C-46 | 4-ethylphenyl |
| C-47 | 3,5-diethylphenyl |
| C-48 | 2-n-propylphenyl |
| C-49 | 3-n-propylphenyl |
| C-50 | 4-n-propylphenyl |
| C-51 | 2-isopropylphenyl |
| C-52 | 3-isopropylphenyl |
| C-53 | 4-isopropylphenyl |
| C-54 | 2,4-diisopropylphenyl |
| C-55 | 3,5-diisopropylphenyl |
| C-56 | 4-n-butylphenyl |
| C-57 | 4-sec-butylphenyl |
| C-58 | 4-isobutylphenyl |
| C-59 | 4-tert-butylphenyl |
| C-60 | 3-tert-butylphenyl |
| C-61 | 2-tert-butylphenyl |
| C-62 | 2,4-ditert-butylphenyl |
| C-63 | 2,5-ditert-butylphenyl |
| C-64 | 4-n-hexylphenyl |
| C-65 | 2-methyl-4-tert-butylphenyl |
| C-66 | 2-methyl-6-tert-butylphenyl |
| C-67 | 2-methyl-4-isopropylphenyl |
| C-68 | 2-methyl-4-cyclohexylphenyl |
| C-69 | 2-bromophenyl |
| C-70 | 3-bromophenyl |
| C-71 | 4-bromophenyl |
| C-72 | 2-chloro-4-fluorophenyl |
| C-73 | 2-fluoro-3-chlorophenyl |
| C-74 | 2-fluoro-4-chlorophenyl |
| C-75 | 2-fluoro-4-bromophenyl |
| C-76 | 2-methyl-3-chlorophenyl |
| C-77 | 2-methyl-4-chlorophenyl |
| C-78 | 2-methyl-5-chlorophenyl |
| C-79 | 2-methyl-6-chlorophenyl |
| C-80 | 2-methyl-4-fluorophenyl |
| C-81 | 2-methyl-3-bromophenyl |
| C-82 | 2-methyl-4-bromophenyl |
| C-83 | 2-methyl-3-methoxyphenyl |
| C-84 | 2-methyl-4-methoxyphenyl |
| C-85 | 2-methyl-5-methoxyphenyl |
| C-86 | 2-methyl-6-methoxyphenyl |
| C-87 | 2-methyl-4-isopropoxyphenyl |
| C-88 | 2-methyl-2,5-dimethoxyphenyl |
| C-89 | 2-methoxyphenyl |
| C-90 | 3-methoxyphenyl |
| C-91 | 4-methoxyphenyl |
| C-92 | 2,3-dimethoxyphenyl |
| C-93 | 2,4-dimethoxyphenyl |
| C-94 | 2,5-dimethoxyphenyl |
| C-95 | 2,6-dimethoxyphenyl |
| C-96 | 3,4-dimethoxyphenyl |
| C-97 | 3,5-dimethoxyphenyl |
| C-98 | 3,6-dimethoxyphenyl |
| C-99 | 2,3,4-trimethoxyphenyl |
| C-100 | 2,3,5-trimethoxyphenyl |

TABLE C-continued

| No. | W |
|---|---|
| C-101 | 2,3,6-trimethoxyphenyl |
| C-102 | 2,4,5-trimethoxyphenyl |
| C-103 | 2,4,6-trimethoxyphenyl |
| C-104 | 3,4,5-trimethoxyphenyl |
| C-105 | 2-ethoxyphenyl |
| C-106 | 3-ethoxyphenyl |
| C-107 | 4-ethoxyphenyl |
| C-108 | 2-isopropoxyphenyl |
| C-109 | 3-isopropoxyphenyl |
| C-110 | 4-isopropoxyphenyl |
| C-111 | 3-tert-butoxyphenyl |
| C-112 | 4-tert-butoxyphenyl |
| C-113 | 2-trifluoromethoxyphenyl |
| C-114 | 3-trifluoromethoxyphenyl |
| C-115 | 4-trifluoromethoxyphenyl |
| C-116 | 3-(1',1',2',2'-tetrafluoro)ethoxyphenyl |
| C-117 | 4-(1',1',2',2'-tetrafluoro)ethoxyphenyl |
| C-118 | 2-chloromethylphenyl |
| C-119 | 3-chloromethylphenyl |
| C-120 | 4-chloromethylphenyl |
| C-121 | 2-trifluoromethylphenyl |
| C-122 | 3-trifluoromethylphenyl |
| C-123 | 4-trifluoromethylphenyl |
| C-124 | 2-cyclopropylphenyl |
| C-125 | 3-cyclopropylphenyl |
| C-126 | 4-cyclopropylphenyl |
| C-127 | 3-cyclohexylphenyl |
| C-128 | 4-cyclohexylphenyl |
| C-129 | 1-naphthyl |
| C-130 | 2-naphthyl |
| C-131 | 9-anthryl |
| C-132 | benzyl |
| C-133 | 2-methylbenzyl |
| C-134 | 3-methylbenzyl |
| C-135 | 4-methylbenzyl |
| C-136 | 4-tert-butylbenzyl |
| C-137 | 2-chlorobenzyl |
| C-138 | 3-chlorobenzyl |
| C-139 | 4-chlorobenzyl |
| C-140 | 2,4-dichlorobenzyl |
| C-141 | 2,6-dichlorobenzyl |
| C-142 | 2,4,6-trichlorobenzyl |
| C-143 | 2-trifluoromethylbenzyl |
| C-144 | 3-trifluoromethylbenzyl |
| C-145 | 4-trifluoromethylbenzyl |
| C-146 | 2-methoxybenzyl |
| C-147 | 4-methoxybenzyl |
| C-148 | 4-tert-butoxybenzyl |
| C-149 | 4-phenoxybenzyl |
| C-150 | 1-phenethyl |
| C-151 | 2-phenethyl |
| C-152 | 1-phenylpropyl |
| C-153 | 2-phenylpropyl |
| C-154 | 3-phenylpropyl |
| C-155 | 2-methyl-2-phenylpropyl |
| C-156 | 2-methyl-3-phenylpropyl |
| C-157 | 4-phenylbutyl |
| C-158 | 2-pyridyl |
| C-159 | 3-pyridyl |
| C-160 | 4-pyridyl |
| C-161 | 2,6-pyrimidinyl |
| C-162 | 1,5-pyrimidinyl |
| C-163 | 2-thienyl |
| C-164 | 3-thienyl |
| C-165 | 2-furyl |
| C-166 | 3-furyl |
| C-167 | 4-thiazolyl |
| C-168 | 2-benzothiazolyl |
| C-169 | 1,3-dioxan-2-yl |
| C-170 | cyclopropyl |
| C-171 | cyclobutyl |
| C-172 | cyclopentyl |
| C-173 | cyclohexyl |
| C-174 | 1-methylcyclopropyl |
| C-175 | 2,2-dimethylcyclopropyl |
| C-176 | 1-methylcyclohexyl |
| C-177 | 2,2-difluorocyclopropyl |
| C-178 | 2,2-dichlorocyclopropyl |
| C-179 | 2,2-dibromocyclopropyl |
| C-180 | 2,2-dichloro-3-methylcyclopropyl |
| C-181 | 2,2,3,3-tetrafluorocyclobutyl |
| C-182 | $CH_3$ |
| C-183 | $CH_3CH_2$ |
| C-184 | $CH_3CH_2CH_2$ |
| C-185 | $(CH_3)_2CH$ |
| C-186 | $CH_2=CH-CH_2$ |
| C-187 | $HC\equiv C-CH_2$ |
| C-188 | trifluoromethyl |
| C-189 | $(CH_3)_3C$ |

TABLE D

| No | $R^2$ | $R^3$ |
|---|---|---|
| D-1 | $CH_3$ | H |
| D-2 | $CH_3$ | $CH_3$ |
| D-3 | $CH_3$ | $C_2H_5$ |
| D-4 | $CH_3$ | $n-C_3H_7$ |
| D-5 | $CH_3$ | $i-C_3H_7$ |
| D-6 | $CH_3$ | $n-C_4H_9$ |
| D-7 | $CH_3$ | $s-C_4H_9$ |
| D-8 | $CH_3$ | $i-C_4H_9$ |
| D-9 | $CH_3$ | $t-C_4H_9$ |
| D-10 | $CH_3$ | $n-C_5H_{11}$ |
| D-11 | $CH_3$ | $i-C_5H_{11}$ |
| D-12 | $CH_3$ | $neo-C_5H_{11}$ |
| D-13 | $CH_3$ | $n-C_6H_{13}$ |
| D-14 | $CH_3$ | $CH_2CH_2Cl$ |
| D-15 | $CH_3$ | $(CH_2)_4Cl$ |
| D-16 | $CH_3$ | $CH_2CN$ |
| D-17 | $CH_3$ | $CH_2CH_2CN$ |
| D-18 | $CH_3$ | $(CH_2)_3CN$ |
| D-19 | $CH_3$ | $(CH_2)_4CN$ |
| D-20 | $CH_3$ | $(CH_2)_6CN$ |
| D-21 | $CH_3$ | cyclopropylmethyl |
| D-22 | $CH_3$ | 2-methoxyeth-1-yl |
| D-23 | $CH_3$ | 2-ethoxyeth-1-yl |
| D-24 | $CH_3$ | 2-isopropoxy-eth-1-yl |
| D-25 | $CH_3$ | 3-methoxy-prop-1-yl |
| D-26 | $CH_3$ | 3-ethoxyprop-1-yl |
| D-27 | $CH_3$ | 3-isopropoxy-prop-1-yl |
| D-28 | $CH_3$ | 4-methoxybut-1-yl |
| D-29 | $CH_3$ | 4-isopropoxy-but-1-yl |
| D-30 | $CH_3$ | propen-3-yl |
| D-31 | $CH_3$ | but-2-en-1-yl |
| D-32 | $CH_3$ | 3-methyl-but-2-en-1-yl |
| D-33 | $CH_3$ | 2-trifluoro-methoxyeth-1-yl |
| D-34 | $CH_3$ | 3-trifluoro-methoxyprop-1-yl |
| D-35 | $CH_3$ | 4-difluoro-methoxybut-1-yl |
| D-36 | $4-F-C_6H_4$ | H |
| D-37 | $4-F-C_6H_4$ | $CH_3$ |
| D-38 | $4-F-C_6H_4$ | $CH_2H_5$ |
| D-39 | $4-F-C_6H_4$ | $n-C_3H_7$ |
| D-40 | $4-F-C_6H_4$ | $i-C_3H_7$ |
| D-41 | $4-F-C_6H_4$ | $CH_2-C\equiv CH$ |
| D-42 | $4-F-C_6H_4$ | $n-C_4H_9$ |
| D-43 | $4-F-C_6H_4$ | $t-C_4H_9$ |
| D-44 | $4-F-C_6H_4$ | $n-C_6H_{13}$ |
| D-45 | $4-F-C_6H_4$ | (E)-1-chloro-propen-3-yl |
| D-46 | $CH_2CH_3$ | H |
| D-47 | $CH_2CH_3$ | $CH_3$ |
| D-48 | $CH_2CH_3$ | $CH_2CH_3$ |

TABLE D-continued

| No | $R^2$ | $R^3$ |
|---|---|---|
| D-49 | $CH_2CH_3$ | $n\text{-}C_3H_7$ |
| D-50 | $CH_2CH_3$ | $CH_2\text{—}C\equiv CH$ |
| D-51 | $CH_2CH_3$ | $CH_2\text{—}CH=CH_2$ |
| D-52 | $CH_2CH_3$ | $tert\text{-}C_4H_9$ |
| D-53 | $C_6H_5$ | H |
| D-54 | $C_6H_5$ | $CH_3$ |
| D-55 | $C_6H_5$ | $C_2H_5$ |
| D-56 | $C_6H_5$ | $n\text{-}C_3H_7$ |
| D-57 | $C_6H_5$ | $i\text{-}C_3H_7$ |
| D-58 | $C_6H_5$ | $CH_2\text{—}C\equiv CH$ |
| D-59 | $C_6H_5$ | $n\text{-}C_4H_9$ |
| D-60 | $C_6H_5$ | $t\text{-}C_4H_9$ |
| D-61 | $C_6H_5$ | $n\text{-}C_6H_{13}$ |
| D-62 | $OCH_3$ | H |
| D-63 | $OCH_3$ | $CH_3$ |
| D-64 | $OCH_3$ | $C_2H_5$ |
| D-65 | $OCH_3$ | $n\text{-}C_3H_7$ |
| D-66 | $OCH_3$ | $i\text{-}C_3H_7$ |
| D-67 | $O\text{-}i\text{-}C_3H_7$ | $CH_3$ |
| D-68 | $O\text{-}i\text{-}C_3H_7$ | $CH_2CH_3$ |
| D-69 | $O\text{—}CH_2CH_3$ | $CH_3$ |
| D-70 | $O\text{—}CH_2CH_3$ | $CH_2CH_3$ |
| D-71 | O-cyclopropyl | $CH_3$ |
| D-72 | $O\text{—}CH_2CH_2CH_3$ | $CH_3$ |
| D-73 | $O\text{—}CH_2CH_2CH_3$ | $CH_2CH_3$ |
| D-74 | $O\text{—}CH(CH_2CH_3)_2$ | $CH_3$ |
| D-75 | $O\text{—}CH(CH_2CH_3)_2$ | $CH_2CH_3$ |
| D-76 | O-cyclopentyl | $CH_3$ |
| D-77 | $O\text{—}CH(CH_3)CH_2CH_3$ | $CH_3$ |
| D-78 | $O\text{—}CH(CH_3)CH_2CH_3$ | $C_2H_5$ |
| D-79 | $O\text{—}CH_2CH_2CH_2CH_3$ | $CH_3$ |
| D-80 | $O\text{—}CH_2CH_2CH_2CH_2CH_2CH_3$ | $CH_3$ |
| D-81 | $O\text{—}CH_2\text{—}CH(CH_3)CH_3$ | $CH_3$ |
| D-82 | $O\text{—}CH_2\text{—}CH(CH_3)CH_3$ | $C_2H_5$ |
| D-83 | Cl | $CH_3$ |
| D-84 | Cl | $C_2H_5$ |
| D-85 | Cl | $n\text{-}C_3H_7$ |
| D-86 | Cl | $i\text{-}C_3H_7$ |
| D-87 | $SCH_3$ | H |
| D-88 | $SCH_3$ | $CH_3$ |
| D-89 | $SCH_3$ | $C_2H_5$ |
| D-90 | O-cyclohexyl | $CH_3$ |
| D-91 | O-cyclohexyl | $CH_2CH_3$ |
| D-92 | cyclopropyl | H |
| D-93 | cyclopropyl | $CH_3$ |
| D-94 | cyclopropyl | $C_2H_5$ |
| D-95 | cyclopropyl | $n\text{-}C_3H_7$ |
| D-96 | cyclopropyl | $i\text{-}C_3H_7$ |
| D-97 | cyano | $CH_3$ |
| D-98 | cyano | $CH_2CH_3$ |
| D-99 | cyano | $CH_2\text{—}C\equiv CH$ |
| D-100 | $CHF_2$ | $CH_3$ |
| D-101 | $CF_3$ | $CH_3$ |
| D-102 | $CH_2CHF_2$ | $CH_3$ |
| D-103 | $CH_2CF_3$ | $CH_3$ |
| D-104 | $CHFCH_3$ | $CH_3$ |
| D-105 | methoxymethyl | $CH_3$ |
| D-106 | ethoxymethyl | $CH_3$ |
| D-107 | 1-methoxyeth-1-yl | $CH_3$ |
| D-108 | 1-ethoxyeth-1-yl | $CH_3$ |
| D-109 | ethenyl | $CH_3$ |
| D-110 | (E)-prop-1-en-1-yl | $CH_3$ |
| D-111 | (Z)-prop-1-en-1-yl | $CH_3$ |
| D-112 | 2-methylprop-1-en-1-yl | $CH_3$ |
| D-113 | ethynl | $CH_3$ |
| D-114 | prop-1-yn-1-yl | $CH_3$ |
| D-115 | but-1-yn-3-yl | $CH_3$ |
| D-116 | $NHC_6H_5$ | $CH_3$ |
| D-117 | $N(CH_3)C_6H_5$ | $CH_3$ |
| D-118 | $NHCH_2CH_2CH_2CH_3$ | $CH_3$ |
| D-119 | $NHC(CH_3)CH_2CH_2CH_3$ | $CH_3$ |
| D-120 | $SC_6H_5$ | $CH_3$ |
| D-121 | $C(H)=NOCH_3$ | $CH_3$ |
| D-122 | $C(H)=NOCH_2CH_3$ | $CH_3$ |
| D-123 | $C(H)=NOCH_2CH_2CH_3$ | $CH_3$ |
| D-124 | $C(H)=NOCH_2C=CH_2$ | $CH_3$ |
| D-125 | $C(H)=NOCH_2C\equiv CH$ | $CH_3$ |
| D-126 | $C(CH_3)=NOCH_3$ | $CH_3$ |
| D-127 | $C(CH_3)=NOCH_2CH_3$ | $CH_3$ |
| D-128 | $C(CH_3)=NOCH_2CH_2CH_3$ | $CH_3$ |
| D-129 | $C(CH_3)=NOCH_2C=CH_2$ | $CH_3$ |
| D-130 | $C(CH_3)=NOCH_2C\equiv CH$ | $CH_3$ |
| D-131 | H | $CH_3$ |
| D-132 | $n\text{-}C_3H_7$ | $CH_3$ |
| D-133 | $i\text{-}C_3H_7$ | $CH_3$ |
| D-134 | $n\text{-}C_4H_9$ | $CH_3$ |
| D-135 | $s\text{-}C_4H_9$ | $CH_3$ |
| D-136 | $i\text{-}C_4H_9$ | $CH_3$ |
| D-137 | $t\text{-}C_4H_9$ | $CH_3$ |
| D-138 | $n\text{-}C_5H_{11}$ | $CH_3$ |
| D-139 | $i\text{-}C_5H_{11}$ | $CH_3$ |
| D-140 | $neo\text{-}C_5H_{11}$ | $CH_3$ |
| D-141 | cyclopentyl | $CH_3$ |
| D-142 | $n\text{-}C_6H_{13}$ | $CH_3$ |
| D-143 | cyclohexyl | $CH_3$ |
| D-144 | cyclobutyl | $CH_3$ |
| D-145 | $CH_2CH_2Cl$ | $CH_3$ |
| D-146 | $(CH_2)_4Cl$ | $CH_3$ |
| D-147 | $CH_2CN$ | $CH_3$ |
| D-148 | $CH_2CH_2CN$ | $CH_3$ |
| D-149 | $(CH_2)_3CN$ | $CH_3$ |
| D-150 | $(CH_2)_4CN$ | $CH_3$ |
| D-151 | $(CH_2)_6CN$ | $CH_3$ |
| D-152 | cyclohexylmethyl | $CH_3$ |
| D-153 | 2-cyclohexyleth-1-yl | $CH_3$ |
| D-154 | cyclopropylmethyl | $CH_3$ |
| D-155 | 2-cyclopropyleth-1-yl | $CH_3$ |
| D-156 | 2-methoxyeth-1-yl | $CH_3$ |
| D-157 | 2-ethoxyeth-1-yl | $CH_3$ |
| D-158 | 2-isopropoxyeth-1-yl | $CH_3$ |
| D-159 | 3-methoxyprop-1-yl | $CH_3$ |
| D-160 | 3-ethoxyprop-1-yl | $CH_3$ |
| D-161 | 3-isopropoxyprop-1-yl | $CH_3$ |
| D-162 | 4-methoxybut-1-yl | $CH_3$ |
| D-163 | 4-isopropoxybut-1-yl | $CH_3$ |
| D-164 | prop-2-en-1-yl | $CH_3$ |
| D-165 | but-2-en-1-yl | $CH_3$ |
| D-166 | 3-methylbut-2-en-1-yl | $CH_3$ |
| D-167 | 2-trifluoromethoxyeth-1-yl | $CH_3$ |
| D-168 | 3-trifluoromethoxyprop-1-yl | $CH_3$ |
| D-169 | 4-difluoromethoxybut-1-yl | $CH_3$ |
| D-170 | methoxycarbonylmethyl | $CH_3$ |
| D-171 | 2-methoxycarbonyleth-1-yl | $CH_3$ |
| D-172 | E-3-chloroprop-2-en-1-yl | $CH_3$ |
| D-173 | Z-3-chloroprop-2-en-1-yl | $CH_3$ |
| D-174 | prop-2-yn-1-yl | $CH_3$ |
| D-175 | but-2-yn-1-yl | $CH_3$ |
| D-176 | but-3-yn-1-yl | $CH_3$ |
| D-177 | 3-chloroprop-2-yn-1-yl | $CH_3$ |
| D-178 | benzyl | $CH_3$ |
| D-179 | $2\text{-}F\text{—}C_6H_4\text{—}CH_2$ | $CH_3$ |
| D-180 | $3\text{-}F\text{—}C_6H_4\text{—}CH_2$ | $CH_3$ |
| D-181 | $4\text{-}F\text{—}C_6H_4\text{—}CH_2$ | $CH_3$ |
| D-182 | $2,3\text{-}F_2\text{—}C_6H_3\text{—}CH_2$ | $CH_3$ |
| D-183 | $2,4\text{-}F_2\text{—}C_6H_3\text{—}CH_2$ | $CH_3$ |
| D-184 | $2,5\text{-}F_2\text{—}C_6H_3\text{—}CH_2$ | $CH_3$ |
| D-185 | $2,6\text{-}F_2\text{—}C_6H_3\text{—}CH_2$ | $CH_3$ |
| D-186 | $3,4\text{-}F_2\text{—}C_6H_3\text{—}CH_2$ | $CH_3$ |
| D-187 | $3,5\text{-}F_2\text{—}C_6H_3\text{—}CH_2$ | $CH_3$ |
| D-188 | $2\text{-}Cl\text{—}C_6H_4\text{—}CH_2$ | $CH_3$ |
| D-189 | $3\text{-}Cl\text{—}C_6H_4\text{—}CH_2$ | $CH_3$ |
| D-190 | $4\text{-}Cl\text{—}C_6H_4\text{—}CH_2$ | $CH_3$ |
| D-191 | $2,3\text{-}Cl_2\text{—}C_6H_3\text{—}CH_2$ | $CH_3$ |
| D-192 | $2,4\text{-}Cl_2\text{—}C_6H_3\text{—}CH_2$ | $CH_3$ |
| D-193 | $2,5\text{-}Cl_2\text{—}C_6H_3\text{—}CH_2$ | $CH_3$ |
| D-194 | $2,6\text{-}Cl_2\text{—}C_6H_3\text{—}CH_2$ | $CH_3$ |
| D-195 | $3,4\text{-}Cl_2\text{—}C_6H_3\text{—}CH_2$ | $CH_3$ |
| D-196 | $3,5\text{-}Cl_2\text{—}C_6H_3\text{—}CH_2$ | $CH_3$ |
| D-197 | $2,3,4\text{-}Cl_3\text{—}C_6H_2\text{—}CH_2$ | $CH_3$ |
| D-198 | $2,3,5\text{-}Cl_3\text{—}C_6H_2\text{—}CH_2$ | $CH_3$ |
| D-199 | $2,3,6\text{-}Cl_3\text{—}C_6H_2\text{—}CH_2$ | $CH_3$ |
| D-200 | $2,4,5\text{-}Cl_3\text{—}C_6H_2\text{—}CH_2$ | $CH_3$ |
| D-201 | $2,4,6\text{-}Cl_3\text{—}C_6H_2\text{—}CH_2$ | $CH_3$ |
| D-202 | $3,4,5\text{-}Cl_3\text{—}C_6H_2\text{—}CH_2$ | $CH_3$ |

TABLE D-continued

| No | R² | R³ |
|---|---|---|
| D-203 | 2-Br—C₆H₄—CH₂ | CH₃ |
| D-204 | 3-Br—C₆H₄—CH₂ | CH₃ |
| D-205 | 4-Br—C₆H₄—CH₂ | CH₃ |
| D-206 | 2,3-Br₂—C₆H₃—CH₂ | CH₃ |
| D-207 | 2,4-Br₂—C₆H₃—CH₂ | CH₃ |
| D-208 | 2,5-Br₂—C₆H₃—CH₂ | CH₃ |
| D-209 | 2,6-Br₂—C₆H₃—CH₂ | CH₃ |
| D-210 | 3,4-Br₂—C₆H₃—CH₂ | CH₃ |
| D-211 | 3,5-Br₂—C₆H₃—CH₂ | CH₃ |
| D-212 | 2-F-3-Cl—C₆H₃—CH₂ | CH₃ |
| D-213 | 2-F-4-Cl—C₆H₃—CH₂ | CH₃ |
| D-214 | 2-F-5-Cl—C₆H₃—CH₂ | CH₃ |
| D-215 | 2-F-3-Br—C₆H₃—CH₂ | CH₃ |
| D-216 | 2-F-4-Br—C₆H₃—CH₂ | CH₃ |
| D-217 | 2-F-5-Br—C₆H₃—CH₂ | CH₃ |
| D-218 | 2-Cl-3-Br—C₆H₃—CH₂ | CH₃ |
| D-219 | 2-Cl-4-Br—C₆H₃—CH₂ | CH₃ |
| D-220 | 2-Cl-5-Br—C₆H₃—CH₂ | CH₃ |
| D-221 | 3-F-4-Cl—C₆H₃—CH₂ | CH₃ |
| D-222 | 3-F-5-Cl—C₆H₃—CH₂ | CH₃ |
| D-223 | 3-F-6-Cl—C₆H₃—CH₂ | CH₃ |
| D-224 | 3-F-4-Br—C₆H₃—CH₂ | CH₃ |
| D-225 | 3-F-5-Br—C₆H₃—CH₂ | CH₃ |
| D-226 | 3-F-6-Br—C₆H₃—CH₂ | CH₃ |
| D-227 | 3-Cl-4-Br—C₆H₃—CH₂ | CH₃ |
| D-228 | 3-Cl-5-Br—C₆H₃—CH₂ | CH₃ |
| D-229 | 3-Cl-6-Br—C₆H₃—CH₂ | CH₃ |
| D-230 | 4-F-5-Cl—C₆H₃—CH₂ | CH₃ |
| D-231 | 4-F-6-Cl—C₆H₃—CH₂ | CH₃ |
| D-232 | 4-F-5-Br—C₆H₃—CH₂ | CH₃ |
| D-233 | 4-F-6-Br—C₆H₃—CH₂ | CH₃ |
| D-234 | 4-Cl-5-Br—C₆H₃—CH₂ | CH₃ |
| D-235 | 5-F-6-Cl—C₆H₃—CH₂ | CH₃ |
| D-236 | 5-F-6-Br—C₆H₃—CH₂ | CH₃ |
| D-237 | 5-Cl-6-Br—C₆H₃—CH₂ | CH₃ |
| D-238 | 3-Br-4-Cl-5-Br—C₆H₂—CH₂ | CH₃ |
| D-239 | 2-CN—C₆H₄—CH₂ | CH₃ |
| D-240 | 3-CN—C₆H₄—CH₂ | CH₃ |
| D-241 | 4-CN—C₆H₄—CH₂ | CH₃ |
| D-242 | 2-NO₂—C₆H₄—CH₂ | CH₃ |
| D-243 | 3-NO₂—C₆H₄—CH₂ | CH₃ |
| D-244 | 4-NO₂—C₆H₄—CH₂ | CH₃ |
| D-245 | 2-CH₃—C₆H₄—CH₂ | CH₃ |
| D-246 | 3-CH₃—C₆H₄—CH₂ | CH₃ |
| D-247 | 4-CH₃—C₆H₄—CH₂ | CH₃ |
| D-248 | 2,3-(CH₃)₂—C₆H₃—CH₂ | CH₃ |
| D-249 | 2,4-(CH₃)₂—C₆H₃—CH₂ | CH₃ |
| D-250 | 2,5-(CH₃)₂—C₆H₃—CH₂ | CH₃ |
| D-251 | 2,6-(CH₃)₂—C₆H₃—CH₂ | CH₃ |
| D-252 | 3,4-(CH₃)₂—C₆H₃—CH₂ | CH₃ |
| D-253 | 3,5-(CH₃)₂—C₆H₃—CH₂ | CH₃ |
| D-254 | 2-OCH₃—C₆H₄—CH₂ | CH₃ |
| D-255 | 3-OCH₃—C₆H₄—CH₂ | CH₃ |
| D-256 | 4-OCH₃—C₆H₄—CH₂ | CH₃ |
| D-257 | 2-OC₂H₅—C₆H₄—CH₂ | CH₃ |
| D-258 | 3-OC₂H₅—C₆H₄—CH₂ | CH₃ |
| D-259 | 4-OC₂H₅—C₆H₄—CH₂ | CH₃ |
| D-260 | 2-CF₃—C₆H₄—CH₂ | CH₃ |
| D-261 | 3-CF₃—C₆H₄—CH₂ | CH₃ |
| D-262 | 4-CF₃—C₆H₄—CH₂ | CH₃ |
| D-263 | 2-F—C₆H₄ | CH₃ |
| D-264 | 3-F—C₆H₄ | CH₃ |
| D-265 | 2,3-F₂—C₆H₃ | CH₃ |
| D-266 | 2,4-F₂—C₆H₃ | CH₃ |
| D-267 | 2,5-F₂—C₆H₃ | CH₃ |
| D-268 | 2,6-F₂—C₆H₃ | CH₃ |
| D-269 | 3,4-F₂—C₆H₃ | CH₃ |
| D-270 | 3,5-F₂—C₆H₃ | CH₃ |
| D-271 | 2-Cl—C₆H₄ | CH₃ |
| D-272 | 3-Cl—C₆H₄ | CH₃ |
| D-273 | 4-Cl—C₆H₄ | CH₃ |
| D-274 | 2,3-Cl₂—C₆H₃ | CH₃ |
| D-275 | 2,4-Cl₂—C₆H₃ | CH₃ |
| D-276 | 2,5-Cl₂—C₆H₃ | CH₃ |
| D-277 | 2,6-Cl₂—C₆H₃ | CH₃ |
| D-278 | 3,4-Cl₂—C₆H₃ | CH₃ |
| D-279 | 3,5-Cl₂—C₆H₃ | CH₃ |
| D-280 | 2,3,4-Cl₃—C₆H₂ | CH₃ |
| D-281 | 2,3,5-Cl₃—C₆H₂ | CH₃ |
| D-282 | 2,3,6-Cl₃—C₆H₂ | CH₃ |
| D-283 | 2,4,5-Cl₃—C₆H₂ | CH₃ |
| D-284 | 2,4,6-Cl₃—C₆H₂ | CH₃ |
| D-285 | 3,4,5-Cl₃—C₆H₂ | CH₃ |
| D-286 | 2-Br-C₆H₄ | CH₃ |
| D-287 | 3-Br-C₆H₄ | CH₃ |
| D-288 | 4-Br-C₆H₄ | CH₃ |
| D-289 | 2,3-Br₂—C₆H₃ | CH₃ |
| D-290 | 2,4-Br₂—C₆H₃ | CH₃ |
| D-291 | 2,5-Br₂—C₆H₃ | CH₃ |
| D-292 | 2,6-Br₂—C₆H₃ | CH₃ |
| D-293 | 3,4-Br₂—C₆H₃ | CH₃ |
| D-294 | 3,5-Br₂—C₆H₃ | CH₃ |
| D-295 | 2-F-3-Cl—C₆H₃ | CH₃ |
| D-296 | 2-F-4-Cl—C₆H₃ | CH₃ |
| D-297 | 2-F-5-Cl—C₆H₃ | CH₃ |
| D-298 | 2-F-3-Cl—C₆H₃ | CH₃ |
| D-299 | 2-F-4-Cl—C₆H₃ | CH₃ |
| D-300 | 2-F-5-Cl—C₆H₃ | CH₃ |
| D-301 | 2-Cl-3-Br—C₆H₃ | CH₃ |
| D-302 | 2-Cl-4-Br—C₆H₃ | CH₃ |
| D-303 | 2-Cl-5-Br—C₆H₃ | CH₃ |
| D-304 | 3-F-4-Cl—C₆H₃ | CH₃ |
| D-305 | 3-F-5-Cl—C₆H₃ | CH₃ |
| D-306 | 3-F-6-Cl—C₆H₃ | CH₃ |
| D-307 | 3-F-4-Br—C₆H₃ | CH₃ |
| D-308 | 3-F-5-Br—C₆H₃ | CH₃ |
| D-309 | 3-F-6-Br—C₆H₃ | CH₃ |
| D-310 | 3-Cl-4-Br—C₆H₃ | CH₃ |
| D-311 | 3-Cl-5-Br—C₆H₃ | CH₃ |
| D-312 | 3-Cl-6-Br—C₆H₃ | CH₃ |
| D-313 | 4-F-5-Cl—C₆H₃ | CH₃ |
| D-314 | 4-F-6-Cl—C₆H₃ | CH₃ |
| D-315 | 4-F-5-Br—C₆H₃ | CH₃ |
| D-316 | 4-F-6-Br—C₆H₃ | CH₃ |
| D-317 | 4-Cl-5-Br—C₆H₃ | CH₃ |
| D-318 | 5-F-6-Cl—C₆H₃ | CH₃ |
| D-319 | 5-F-6-Br—C₆H₃ | CH₃ |
| D-320 | 5-Cl-6-Br—C₆H₃ | CH₃ |
| D-321 | 3-Br-4-Cl-5-Br—C₆H₂ | CH₃ |
| D-322 | 2—CN—C₆H₄ | CH₃ |
| D-323 | 3-CN—C₆H₄ | CH₃ |
| D-324 | 4-CN—C₆H₄ | CH₃ |
| D-325 | 2-NO₂—C₆H₄ | CH₃ |
| D-326 | 3-NO₂—C₆H₄ | CH₃ |
| D-327 | 4-NO₂—C₆H₄ | CH₃ |
| D-328 | 2-CH₃—C₆H₄ | CH₃ |
| D-329 | 3-CH₃—C₆H₄ | CH₃ |
| D-330 | 4-CH₃—C₆H₄ | CH₃ |
| D-331 | 2,3-(CH₃)₂—C₆H₃ | CH₃ |
| D-332 | 2,4-(CH₃)₂—C₆H₃ | CH₃ |
| D-333 | 2,5-(CH₃)₂—C₆H₃ | CH₃ |
| D-334 | 2,6-(CH₃)₂—C₆H₃ | CH₃ |
| D-335 | 3,4-(CH₃)₂—C₆H₃ | CH₃ |
| D-336 | 3,5-(CH₃)₂—C₆H₃ | CH₃ |
| D-337 | 2-C₂H₅—C₆H₄ | CH₃ |
| D-338 | 3-C₂H₅—C₆H₄ | CH₃ |
| D-339 | 4-C₂H₅—C₆H₄ | CH₃ |
| D-340 | 2-i-C₃H₇—C₆H₄ | CH₃ |
| D-341 | 3-i-C₃H₇—C₆H₄ | CH₃ |
| D-342 | 4-i-C₃H₇—C₆H₄ | CH₃ |
| D-343 | 3-tert-C₄H₉—C₆H₄ | CH₃ |
| D-344 | 4-tert-C₄H₉—C₆H₄ | CH₃ |
| D-345 | 2-vinyl-C₆H₄ | CH₃ |
| D-346 | 3-vinyl-C₆H₄ | CH₃ |
| D-347 | 4-vinyl-C₆H₄ | CH₃ |
| D-348 | 2-allyl-C₆H₄ | CH₃ |
| D-349 | 3-allyl-C₆H₄ | CH₃ |
| D-350 | 4-allyl-C₆H₄ | CH₃ |
| D-351 | 2-C₆H₅—C₆H₄ | CH₃ |
| D-352 | 3-C₆H₅—C₆H₄ | CH₃ |
| D-353 | 4-C₆H₅—C₆H₄ | CH₃ |
| D-354 | 3-CH₃-5-tert-C₄H₉—C₆H₃ | CH₃ |
| D-355 | 2-OH—C₆H₄ | CH₃ |
| D-356 | 3-OH—C₆H₄ | CH₃ |

TABLE D-continued

| No | R² | R³ |
|---|---|---|
| D-357 | 4-OH—C₆H₄ | CH₃ |
| D-358 | 2-OCH₃—C₆H₄ | CH₃ |
| D-359 | 3-OCH₃—C₆H₄ | CH₃ |
| D-360 | 4-OCH₃—C₆H₄ | CH₃ |
| D-361 | 2,3-(OCH₃)₂—C₆H₃ | CH₃ |
| D-362 | 2,4-(OCH₃)₂—C₆H₃ | CH₃ |
| D-363 | 2,5-(OCH₃)₂—C₆H₃ | CH₃ |
| D-364 | 3,4-(OCH₃)₂—C₆H₃ | CH₃ |
| D-365 | 3,5-(OCH₃)₂—C₆H₃ | CH₃ |
| D-366 | 3,4,5-(OCH₃)₃—C₆H₂ | CH₃ |
| D-367 | 2-OC₂H₅—C₆H₄ | CH₃ |
| D-368 | 3-OC₂H₅—C₆H₄ | CH₃ |
| D-369 | 4-OC₂H₅—C₆H₄ | CH₃ |
| D-370 | 2-O-(n-C₃H₇)—C₆H₄ | CH₃ |
| D-371 | 3-O-(n-C₃H₇)—C₆H₄ | CH₃ |
| D-372 | 4-O-(n-C₃H₇)—C₆H₄ | CH₃ |
| D-373 | 2-O-(i-C₃H₇)—C₆H₄ | CH₃ |
| D-374 | 3-O-(i-C₃H₇)—C₆H₄ | CH₃ |
| D-375 | 4-O-(i-C₃H₇)—C₆H₄ | CH₃ |
| D-376 | 4-O-(n-C₄H₉)—C₆H₄ | CH₃ |
| D-377 | 3-O-(t-C₄H₉)—C₆H₄ | CH₃ |
| D-378 | 4-O-(t-C₄H₉)—C₆H₄ | CH₃ |
| D-379 | 2-O-allyl-C₆H₄ | CH₃ |
| D-380 | 3-O-allyl-C₆H₄ | CH₃ |
| D-381 | 4-O-allyl-C₆H₄ | CH₃ |
| D-382 | 2-CF₃—C₆H₄ | CH₃ |
| D-383 | 3-CF₃—C₆H₄ | CH₃ |
| D-384 | 4-CF₃—C₆H₄ | CH₃ |
| D-385 | 2-acetyl-C₆H₄ | CH₃ |
| D-386 | 3-acetyl-C₆H₄ | CH₃ |
| D-387 | 4-acetyl-C₆H₄ | CH₃ |
| D-388 | 2-methoxycarbonyl-C₆H₄ | CH₃ |
| D-389 | 3-methoxycarbonyl-C₆H₄ | CH₃ |
| D-390 | 4-methoxycarbonyl-C₆H₄ | CH₃ |
| D-391 | 2-aminocarbonyl-C₆H₄ | CH₃ |
| D-392 | 3-aminocarbonyl-C₆H₄ | CH₃ |
| D-393 | 4-aminocarbonyl-C₆H₄ | CH₃ |
| D-394 | 2-dimethylaminocarbonyl-C₆H₄ | CH₃ |
| D-395 | 3-dimethylaminocarbonyl-C₆H₄ | CH₃ |
| D-396 | 4-dimethylaminocarbonyl-C₆H₄ | CH₃ |
| D-397 | 2-(N-methylaminocarbonyl)-C₆H₄ | CH₃ |
| D-398 | 3-(N-methylaminocarbonyl)-C₆H₄ | CH₃ |
| D-399 | 4-(N-methylaminocarbonyl)-C₆H₄ | CH₃ |
| D-400 | 2-H₂N—C₆H₄ | CH₃ |
| D-401 | 3-H₂N—C₆H₄ | CH₃ |
| D-402 | 4-H₂N—C₆H₄ | CH₃ |
| D-403 | 2-aminothiocarbonyl-C₆H₄ | CH₃ |
| D-404 | 3-aminothiocarbonyl-C₆H₄ | CH₃ |
| D-405 | 4-aminothiocarbonyl-C₆H₄ | CH₃ |
| D-406 | 2-methoxyiminomethyl-C₆H₄ | CH₃ |
| D-407 | 3-methoxyiminomethyl-C₆H₄ | CH₃ |
| D-408 | 4-methoxyiminomethyl-C₆H₄ | CH₃ |
| D-409 | 3,4-methylenedioxy-C₆H₃ | CH₃ |
| D-410 | 3,4-difluoromethylenedioxy-C₆H₃ | CH₃ |
| D-411 | 2,3-methylenedioxy-C₆H₃ | CH₃ |
| D-412 | 2-(1'-methoxyiminoeth-1'-yl)-C₆H₄ | CH₃ |
| D-413 | 3-(1'-methoxyiminoeth-1'-yl)-C₆H₄ | CH₃ |
| D-414 | 4-(1'-methoxyiminoeth-1'-yl)-C₆H₄ | CH₃ |
| D-415 | 2-SCH₃—C₆H₄ | CH₃ |
| D-416 | 3-SCH₃—C₆H₄ | CH₃ |
| D-417 | 4-SCH₃—C₆H₄ | CH₃ |
| D-418 | 2-SO₂CH₃—C₆H₄ | CH₃ |
| D-419 | 3-SO₂CH₃—C₆H₄ | CH₃ |
| D-420 | 4-SO₂CH₃—C₆H₄ | CH₃ |
| D-421 | 2-OCF₃—C₆H₄ | CH₃ |
| D-422 | 3-OCF₃—C₆H₄ | CH₃ |
| D-423 | 4-OCF₃—C₆H₄ | CH₃ |
| D-424 | 2-OCHF₃—C₆H₄ | CH₃ |
| D-425 | 3-OCHF₃—C₆H₄ | CH₃ |
| D-426 | 4-OCHF₃—C₆H₄ | CH₃ |
| D-427 | 3-CF₃-4-OCF₃—C₆H₃ | CH₃ |
| D-428 | 2-NHCH₃—C₆H₄ | CH₃ |
| D-429 | 3-NHCH₃—C₆H₄ | CH₃ |
| D-430 | 4-NHCH₃—C₆H₄ | CH₃ |
| D-431 | 2-N(CH₃)₂—C₆H₄ | CH₃ |
| D-432 | 3-N(CH₃)₂—C₆H₄ | CH₃ |
| D-433 | 4-N(CH₃)₂—C₆H₄ | CH₃ |
| D-434 | 2-ethoxycarbonyl-C₆H₄ | CH₃ |
| D-435 | 3-ethoxycarbonyl-C₆H₄ | CH₃ |
| D-436 | 4-ethoxycarbonyl-C₆H₄ | CH₃ |
| D-437 | 2-CH₂CH₂F—C₆H₄ | CH₃ |
| D-438 | 3-CH₂CH₂F—C₆H₄ | CH₃ |
| D-439 | 4-CH₂CH₂F—C₆H₄ | CH₃ |
| D-440 | 2-CH₂CF₃—C₆H₄ | CH₃ |
| D-441 | 3-CH₂CF₃—C₆H₄ | CH₃ |
| D-442 | 4-CH₂CF₃—C₆H₄ | CH₃ |
| D-443 | 2-CF₂CHF₂—C₆H₄ | CH₃ |
| D-444 | 3-CF₂CHF₂—C₆H₄ | CH₃ |
| D-445 | 4-CF₂CHF₂—C₆H₄ | CH₃ |
| D-446 | 2-CHF₂—C₆H₄ | CH₃ |
| D-447 | 3-CHF₂—C₆H₄ | CH₃ |
| D-448 | 4-CHF₂—C₆H₄ | CH₃ |
| D-449 | 2-(1'-oxo-n-prop-1-yl)-C₆H₄ | CH₃ |
| D-450 | 3-(1'-oxo-n-prop-1-yl)-C₆H₄ | CH₃ |
| D-451 | 4-(1'-oxo-n-prop-1-yl)-C₆H₄ | CH₃ |
| D-452 | 2-(1'-oxo-iso-prop-1-yl)-C₆H₄ | CH₃ |
| D-453 | 3-(1'-oxo-iso-prop-1-yl)-C₆H₄ | CH₃ |
| D-454 | 4-(1'-oxo-iso-prop-1-yl)-C₆H₄ | CH₃ |
| D-455 | 3-cyclopropyl-C₆H₄ | CH₃ |
| D-456 | 4-cyclopropyl-C₆H₄ | CH₃ |
| D-457 | 4-cyclohexyl-C₆H₄ | CH₃ |
| D-458 | 1-naphthyl | CH₃ |
| D-459 | 2-naphthyl | CH₃ |
| D-460 | 2-pyridyl | CH₃ |
| D-461 | 3-pyridyl | CH₃ |
| D-462 | 4-pyridyl | CH₃ |
| D-463 | 5-CH₃-pyridin-2-yl | CH₃ |
| D-464 | 5-Cl-pyridin-2-yl | CH₃ |
| D-465 | 6-Cl-pyridin-2-yl | CH₃ |
| D-466 | 3,5-Cl₂-pyridin-2-yl | CH₃ |
| D-467 | 6-OCH₃-pyridin-2-yl | CH₃ |
| D-468 | 6-CH₃-pyridin-2-yl | CH₃ |
| D-469 | 6-Cl-pyridin-3-yl | CH₃ |
| D-470 | 6-CH₃-pyridin-3-yl | CH₃ |
| D-471 | 6-OCH₃-pyridin-3-yl | CH₃ |
| D-472 | 2-pyrimidinyl | CH₃ |
| D-473 | 4-OCH₃-pyrimidin-2-yl | CH₃ |
| D-474 | 4-OC₂H₅-pyrimidin-2-yl | CH₃ |
| D-475 | 4-Cl-pyrimidin-2-yl | CH₃ |
| D-476 | 4-CH₃-pyrimidin-2-yl | CH₃ |
| D-477 | 5-CH₃-pyrimidin-2-yl | CH₃ |
| D-478 | 5-Cl-pyrimidin-2-yl | CH₃ |
| D-479 | 5-OCH₃-pyrimidin-2-yl | CH₃ |
| D-480 | 5-OC₂H₅-pyrimidin-2-yl | CH₃ |
| D-481 | 4-pyrimidinyl | CH₃ |
| D-482 | 2-Cl-pyrimidin-4-yl | CH₃ |
| D-483 | 2-OCH₃-pyrimidin-4-yl | CH₃ |
| D-484 | 2-CH₃-pyrimidin-4-yl | CH₃ |
| D-485 | 6-Cl-pyrimidin-4-yl | CH₃ |
| D-486 | 6-CH₃-pyrimidin-4-yl | CH₃ |
| D-487 | 6-OCH₃-pyrimidin-4-yl | CH₃ |
| D-488 | 5-pyrimidinyl | CH₃ |
| D-489 | 2-CH₃-pyrimidin-5-yl | CH₃ |
| D-490 | 2-Cl-pyrimidin-5-yl | CH₃ |
| D-491 | 2-OCH₃-pyrimidin-5-yl | CH₃ |
| D-492 | 2-OC₂H₅-pyrimidin-5-yl | CH₃ |
| D-493 | 2-furyl | CH₃ |
| D-494 | 4-C₂H₅-fur-2-yl | CH₃ |
| D-495 | 4-CH₃-fur-2-yl | CH₃ |
| D-496 | 4-Cl-fur-2-yl | CH₃ |
| D-497 | 4-CN-fur-2-yl | CH₃ |
| D-498 | 5-CH₃-fur-2-yl | CH₃ |
| D-499 | 5-Cl-fur-2-yl | CH₃ |
| D-500 | 5-CN-fur-2-yl | CH₃ |
| D-501 | 3-furyl | CH₃ |
| D-502 | 5-CH₃-fur-3-yl | CH₃ |
| D-503 | 5-Cl-fur-3-yl | CH₃ |
| D-504 | 5-CN-fur-3-yl | CH₃ |
| D-505 | 2-thienyl | CH₃ |
| D-506 | 4-CH₃-thien-2-yl | CH₃ |
| D-507 | 4-Cl-thien-2-yl | CH₃ |
| D-508 | 4-CN-thien-2-yl | CH₃ |
| D-509 | 5-CH₃-thien-2-yl | CH₃ |
| D-510 | 5-Cl-thien-2-yl | CH₃ |

TABLE D-continued

| No | R² | R³ |
|---|---|---|
| D-511 | 5-CN-thien-2-yl | CH₃ |
| D-512 | 3-thienyl | CH₃ |
| D-513 | 5-CH₃-thien-3-yl | CH₃ |
| D-514 | 5-Cl-thien-3-yl | CH₃ |
| D-515 | 5-CN-thien-3-yl | CH₃ |
| D-516 | 4-CH₃-thien-3-yl | CH₃ |
| D-517 | 5-F-thien-3-yl | CH₃ |
| D-518 | 2-oxazolyl | CH₃ |
| D-519 | 4-CH₃-oxazol-2-yl | CH₃ |
| D-520 | 4-Cl-oxazol-2-yl | CH₃ |
| D-521 | 4-CN-oxazol-2-yl | CH₃ |
| D-522 | 5-CH₃-oxazol-2-yl | CH₃ |
| D-523 | 5-Cl-oxazol-2-yl | CH₃ |
| D-524 | 5-CN-oxazol-2-yl | CH₃ |
| D-525 | 4-oxazolyl | CH₃ |
| D-526 | 2-CH₃-oxazol-4-yl | CH₃ |
| D-527 | 2-Cl-oxazol-4-yl | CH₃ |
| D-528 | 2-CN-oxazol-4-yl | CH₃ |
| D-529 | 5-oxazolyl | CH₃ |
| D-530 | 2-CH₃-oxazol-5-yl | CH₃ |
| D-531 | 2-Cl-oxazol-5-yl | CH₃ |
| D-532 | 2-CN-oxazol-5-yl | CH₃ |
| D-533 | 3-isoxazolyl | CH₃ |
| D-534 | 5-CH₃-isoxazol-3-yl | CH₃ |
| D-535 | 5-Cl-isoxazol-3-yl | CH₃ |
| D-536 | 5-CN-isoxazol-3-yl | CH₃ |
| D-537 | 5-isoxazolyl | CH₃ |
| D-538 | 3-CH₃-isoxazol-5-yl | CH₃ |
| D-539 | 3-Cl-isoxazol-5-yl | CH₃ |
| D-540 | 3-CN-isoxazol-5-yl | CH₃ |
| D-541 | 2-thiazolyl | CH₃ |
| D-542 | 4-CH₃-thiazol-2-yl | CH₃ |
| D-543 | 4-Cl-thiazol-2-yl | CH₃ |
| D-544 | 4-CN-thiazol-2-yl | CH₃ |
| D-545 | 5-CH₃-thiazol-2-yl | CH₃ |
| D-546 | 5-Cl-thiazol-2-yl | CH₃ |
| D-547 | 5-CN-thiazol-2-yl | CH₃ |
| D-548 | 4-thiazolyl | CH₃ |
| D-549 | 2-CH₃-thiazol-4-yl | CH₃ |
| D-550 | 2-Cl-thiazol-4-yl | CH₃ |
| D-551 | 2-CN-thiazol-4-yl | CH₃ |
| D-552 | 2-SCH₃-thiazol-4-yl | CH₃ |
| D-553 | 5-thiazolyl | CH₃ |
| D-554 | 2-CH₃-thiazol-5-yl | CH₃ |
| D-555 | 2-Cl-thiazol-5-yl | CH₃ |
| D-556 | 2-CN-thiazol-5-yl | CH₃ |
| D-557 | 3-isothiazolyl | CH₃ |
| D-558 | 5-CH₃-isothiazol-3-yl | CH₃ |
| D-559 | 5-Cl-isothiazol-3-yl | CH₃ |
| D-560 | 5-CN-isothiazol-3-yl | CH₃ |
| D-561 | 5-isothiazolyl | CH₃ |
| D-562 | 3-CH₃-isothiazol-5-yl | CH₃ |
| D-563 | 3-Cl-isothiazol-5-yl | CH₃ |
| D-564 | 3-CN-isothiazol-5-yl | CH₃ |
| D-565 | 2-imidazolyl | CH₃ |
| D-566 | 4-CH₃-imidazol-2-yl | CH₃ |
| D-567 | 4-Cl-imidazol-2-yl | CH₃ |
| D-568 | 4-CN-imidazol-2-yl | CH₃ |
| D-569 | 1-CH₃-imidazol-2-yl | CH₃ |
| D-570 | 1-CH₃-4-Cl-imidazol-2-yl | CH₃ |
| D-571 | 1,4-(CH₃)₂-imidazol-2-yl | CH₃ |
| D-572 | 1-CH₃-5-Cl-imidazol-2-yl | CH₃ |
| D-573 | 1,5-(CH₃)₂-imidazol-2-yl | CH₃ |
| D-574 | 4-imidazolyl | CH₃ |
| D-575 | 2-CH₃-imidazol-4-yl | CH₃ |
| D-576 | 2-Cl-imidazol-4-yl | CH₃ |
| D-577 | 1-CH₃-imidazol-4-yl | CH₃ |
| D-578 | 1,2-(CH₃)₂-imidazol-4-yl | CH₃ |
| D-579 | 1-CH₃-2-Cl-imidazol-4-yl | CH₃ |
| D-580 | 1-CH₃-imidazol-5-yl | CH₃ |
| D-581 | 1-CH₃-3-Cl-imidazol-5-yl | CH₃ |
| D-582 | 1,2-(CH₃)₂-imidazol-5-yl | CH₃ |
| D-583 | 3-pyrazolyl | CH₃ |
| D-584 | 5-CH₃-pyrazol-3-yl | CH₃ |
| D-585 | 5-Cl-pyrazol-3-yl | CH₃ |
| D-586 | 5-CN-pyrazol-3-yl | CH₃ |
| D-587 | 1-CH₃-pyrazol-3-yl | CH₃ |
| D-588 | 1-CH₃-4-Cl-pyrazol-3-yl | CH₃ |
| D-589 | 1-CH₃-5-Cl-pyrazol-3-yl | CH₃ |
| D-590 | 1,5-(CH₃)₂-pyrazol-3-yl | CH₃ |
| D-591 | 1-CH₃-pyrazol-5-yl | CH₃ |
| D-592 | 1-CH₃-3-Cl-pyrazol-5-yl | CH₃ |
| D-593 | 1,3-(CH₃)₂-pyrazol-5-yl | CH₃ |
| D-594 | 4-pyrazolyl | CH₃ |
| D-595 | 3-Cl-pyrazol-4-yl | CH₃ |
| D-596 | 3-CH₃-pyrazol-4-yl | CH₃ |
| D-597 | 1-CH₃-pyrazol-4-yl | CH₃ |
| D-598 | 1-CH₃-3-Cl-pyrazol-4-yl | CH₃ |
| D-599 | 1,3-(CH₃)₂-pyrazol-4-yl | CH₃ |
| D-600 | 1,3,4-oxadiazol-5-yl | CH₃ |
| D-601 | 2-CH₃-1,3,4-oxadiazol-5-yl | CH₃ |
| D-602 | 2-Cl-1,3,4-oxadiazol-5-yl | CH₃ |
| D-603 | 2-CF₃-1,3,4-oxadiazol-5-yl | CH₃ |
| D-604 | 2-i-C₃H₇-1,3,4-oxadiazol-5-yl | CH₃ |
| D-605 | 2-OCH₃-1,3,4-oxadiazol-5-yl | CH₃ |
| D-606 | 1,2,4-oxadiazol-3-yl | CH₃ |
| D-607 | 5-CH₃-1,2,4-oxadiazol-3-yl | CH₃ |
| D-608 | 5-i-C₃H₇-1,2,4-oxadiazol-3-yl | CH₃ |
| D-609 | 5-Cl-1,2,4-oxadiazol-3-yl | CH₃ |
| D-610 | 5-CF₃-1,2,4-oxadiazol-3-yl | CH₃ |
| D-611 | 1,2,4-triazol-3-yl | CH₃ |
| D-612 | 1-CH₃-1,2,4-triazol-3-yl | CH₃ |
| D-613 | 3-fluoropyridin-2-yl | CH₃ |
| D-614 | 3-chloropyridin-2-yl | CH₃ |
| D-615 | 3-bromopyridin-2-yl | CH₃ |
| D-616 | 3-methylpyridin-2-yl | CH₃ |
| D-617 | 3-trifluoromethylpyridin-2-yl | CH₃ |
| D-618 | 3-methoxypyridin-2-yl | CH₃ |
| D-619 | 4-fluoropyridin-2-yl | CH₃ |
| D-620 | 4-chloropyridin-2-yl | CH₃ |
| D-621 | 4-bromopyridin-2-yl | CH₃ |
| D-622 | 4-methylpyridin-2-yl | CH₃ |
| D-623 | 4-trifluoromethylpyridin-2-yl | CH₃ |
| D-624 | 4-methoxypyridin-2-yl | CH₃ |
| D-625 | 5-fluoropyridin-2-yl | CH₃ |
| D-626 | 5-bromopyridin-2-yl | CH₃ |
| D-627 | 6-trifluoromethylpyridin-2-yl | CH₃ |
| D-628 | 2-fluoropyridin-3-yl | CH₃ |
| D-629 | 2-chloropyridin-3-yl | CH₃ |
| D-630 | 2-bromopyridin-3-yl | CH₃ |
| D-631 | 2-methylpyridin-3-yl | CH₃ |
| D-632 | 2-trifluoromethylpyridin-3-yl | CH₃ |
| D-633 | 3-methoxypyridin-3-yl | CH₃ |
| D-634 | 4-fluoropyridin-3-yl | CH₃ |
| D-635 | 4-chloropyridin-3-yl | CH₃ |
| D-636 | 4-bromopyridin-3-yl | CH₃ |
| D-637 | 4-methylpyridin-3-yl | CH₃ |
| D-638 | 4-trifluoromethylpyridin-3-yl | CH₃ |
| D-639 | 4-methoxypyridin-3-yl | CH₃ |
| D-640 | 5-fluoropyridin-3-yl | CH₃ |
| D-641 | 5-chloropyridin-3-yl | CH₃ |
| D-642 | 5-bromopyridin-3-yl | CH₃ |
| D-643 | 5-methylpyridin-3-yl | CH₃ |
| D-644 | 5-trifluoromethylpyridin-3-yl | CH₃ |
| D-645 | 5-methoxypyridin-3-yl | CH₃ |
| D-646 | 6-fluoropyridin-3-yl | CH₃ |
| D-647 | 6-bromopyridin-3-yl | CH₃ |
| D-648 | 6-trifluoromethylpyridin-3-yl | CH₃ |
| D-649 | 2-fluoropyridin-4-yl | CH₃ |
| D-650 | 2-chloropyridin-4-yl | CH₃ |
| D-651 | 2-bromopyridin-4-yl | CH₃ |
| D-652 | 2-methylpyridin-4-yl | CH₃ |
| D-653 | 2-trifluoromethylpyridin-4-yl | CH₃ |
| D-654 | 2-methoxypyridin-4-yl | CH₃ |
| D-655 | 3-fluoropyridin-4-yl | CH₃ |
| D-656 | 3-chloropyridin-4-yl | CH₃ |
| D-657 | 3-bromopyridin-4-yl | CH₃ |
| D-658 | 3-methylpyridin-4-yl | CH₃ |
| D-659 | 3-trifluoromethylpyridin-4-yl | CH₃ |
| D-660 | 3-methoxypyridin-4-yl | CH₃ |
| D-661 | 4-fluoropyrimidin-2-yl | CH₃ |
| D-662 | 4-bromopyrimidin-2-yl | CH₃ |
| D-663 | 4-trifluoromethylpyrimidin-2-yl | CH₃ |
| D-664 | 5-fluoropyrimidin-2-yl | CH₃ |

TABLE D-continued

| No | R² | R³ |
|---|---|---|
| D-665 | 5-bromopyrimidin-2-yl | CH₃ |
| D-666 | 5-trifluoromethylpyrimidin-2-yl | CH₃ |
| D-667 | 2-fluoropyrimidin-4-yl | CH₃ |
| D-668 | 2-bromopyrimidin-4-yl | CH₃ |
| D-669 | 2-trifluoromethylpyrimidin-4-yl | CH₃ |
| D-670 | 2-trifluoromethoxypyrimidin-4-yl | CH₃ |
| D-671 | 5-fluoropyrimidin-4-yl | CH₃ |
| D-672 | 5-chloropyrimidin-4-yl | CH₃ |
| D-673 | 5-bromopyrimidin-4-yl | CH₃ |
| D-674 | 5-methoxypyrimidin-4-yl | CH₃ |
| D-675 | 5-trifluoromethylpyrimidin-4-yl | CH₃ |
| D-676 | 5-methoxypyrimidin-4-yl | CH₃ |
| D-677 | 6-fluoropyrimidin-4-yl | CH₃ |
| D-678 | 6-bromopyrimidin-4-yl | CH₃ |
| D-679 | 6-trifluoromethylpyrimidin-4-yl | CH₃ |
| D-680 | 2-fluoropyrimidin-5-yl | CH₃ |
| D-681 | 2-bromopyrimidin-5-yl | CH₃ |
| D-682 | 2-trifluoromethylpyrimidin-5-yl | CH₃ |
| D-683 | 4-fluoropyrimidin-5-yl | CH₃ |
| D-684 | 4-chloropyrimidin-5-yl | CH₃ |
| D-685 | 4-bromopyrimidin-5-yl | CH₃ |
| D-686 | 4-methylpyrimidin-5-yl | CH₃ |
| D-687 | 4-trifluoromethylpyrimidin-5-yl | CH₃ |
| D-688 | 3-fluoro-5-trifluoromethyl-pyridin-2-yl | CH₃ |
| D-689 | 3,6-dichloro-5-trifluoromethyl-pyridin-2-yl | CH₃ |
| D-690 | 5,6-dichloro-3-trifluoromethyl-pyridin-2-yl | CH₃ |
| D-691 | 5-chloro-3-trifluoromethyl-pyridin-2-yl | CH₃ |
| D-692 | 3-chloro-5-trifluoromethyl-pyridin-2-yl | CH₃ |
| D-693 | 6-chloro-4-cyanopyridin-2-yl | CH₃ |
| D-694 | 3-cyano-5-nitropyridin-2-yl | CH₃ |
| D-695 | 2-chloro-6-fluoropyridin-4-yl | CH₃ |
| D-696 | 6-chloro-4-fluoropyridin-2-yl | CH₃ |
| D-697 | 4,6-difluoropyridin-2-yl | CH₃ |
| D-698 | 3,5-dichloro-6-fluoropyridin-2-yl | CH₃ |
| D-699 | 6-methoxy-3-nitropyridin-2-yl | CH₃ |
| D-700 | 4-cyano-6-fluoropyridin-2-yl | CH₃ |
| D-701 | 6-chloro-5-cyanopyridin-2-yl | CH₃ |
| D-702 | 6-chloro-3-cyanopyridin-2-yl | CH₃ |
| D-703 | 4-cyano-3,5,6-trifluoropyridin-2-yl | CH₃ |
| D-704 | 6-chloro-5-nitropyridin-2-yl | CH₃ |
| D-705 | 6-chloro-3-nitropyridin-2-yl | CH₃ |
| D-706 | 5-cyano-6-fluoropyridin-2-yl | CH₃ |
| D-707 | 3-cyano-6-fluoropyridin-2-yl | CH₃ |
| D-708 | 4,6-dicyanopyridin-2-yl | CH₃ |
| D-709 | 5-trichloromethylpyridin-2-yl | CH₃ |
| D-710 | 5-cyanopyridin-2-yl | CH₃ |
| D-711 | 5-bromo-4-trifluoromethylpyridin-2-yl | CH₃ |
| D-712 | 3-nitro-5-trifluoromethylpyridin-2-yl | CH₃ |
| D-713 | 5-aminopyridin-2-yl | CH₃ |
| D-714 | 2,3,5,6-tetrafluoropyridin-2-yl | CH₃ |
| D-715 | 5-nitropyridin-2-yl | CH₃ |
| D-716 | 4-methyl-5-nitropyridin-2-yl | CH₃ |
| D-717 | 5-difluoromethylpyridin-2-yl | CH₃ |
| D-718 | 5-fluoromethylpyridin-2-yl | CH₃ |
| D-719 | 4,6-difluoropyrimidin-2-yl | CH₃ |
| D-720 | 2,6-difluoropyrimidin-4-yl | CH₃ |
| D-721 | 2-chloro-6-trichloromethyl-pyrimidin-4-yl | CH₃ |
| D-722 | 2,6-dichloropyrimidin-4-yl | CH₃ |
| D-723 | 5-methoxycarbonylpyridin-2-yl | CH₃ |
| D-724 | 5-chloro-6-fluoropyridin-2-yl | CH₃ |
| D-725 | 5-chloro-6-hydroxypyridin-2-yl | CH₃ |
| D-726 | 5-chloro-6-methoxypyridin-2-yl | CH₃ |
| D-727 | 5-chloro-6-cyanopyridin-2-yl | CH₃ |
| D-728 | 5,6-dichloropyridin-2-yl | CH₃ |
| D-729 | 6-bromo-5-chloropyridin-2-yl | CH₃ |
| D-730 | 5-bromo-6-fluoropyridin-2-yl | CH₃ |
| D-731 | 5-bromo-6-chloropyridin-2-yl | CH₃ |
| D-732 | 5-bromo-6-cyanopyridin-2-yl | CH₃ |
| D-733 | 5-bromo-6-hydroxypyridin-2-yl | CH₃ |
| D-734 | 5-bromo-6-methoxypyridin-2-yl | CH₃ |
| D-735 | 5,6-dibromopyridin-2-yl | CH₃ |
| D-736 | 4-cyanopyridin-2-yl | CH₃ |
| D-737 | 6-cyanopyridin-2-yl | CH₃ |
| D-738 | 4-chloro-6-methylpyrimidin-2-yl | CH₃ |
| D-739 | 2-chloro-6-fluoropyridin-4-yl | CH₃ |
| D-740 | 5-bromo-4-trifluoromethylpyridin-2-yl | CH₃ |
| D-741 | 4,5-dichloropyridin-2-yl | CH₃ |
| D-742 | 4,5-dibromopyridin-2-yl | CH₃ |
| D-743 | 5,6-dichloropyridin-2-yl | CH₃ |
| D-744 | 4,6-dichloropyridin-2-yl | CH₃ |
| D-745 | 4,6-dibromopyridin-2-yl | CH₃ |
| D-746 | 5,6-dibromopyridin-2-yl | CH₃ |
| D-747 | 4-bromo-5-chloropyridin-2-yl | CH₃ |
| D-748 | 6-bromo-5-chloropyridin-2-yl | CH₃ |
| D-749 | 5-bromo-4-chloropyridin-2-yl | CH₃ |
| D-750 | 5-bromo-4-chloropyridin-2-yl | CH₃ |
| D-751 | 6-bromo-4-chloropyridin-2-yl | CH₃ |
| D-752 | 4-bromo-6-chloropyridin-2-yl | CH₃ |
| D-753 | 6-chloro-4-methoxypyridin-2-yl | CH₃ |
| D-754 | 6-bromo-4-methoxypyridin-2-yl | CH₃ |
| D-755 | 6-chloroquinazolin-2-yl | CH₃ |
| D-756 | quinazolin-2-yl | CH₃ |
| D-757 | 4-cyanopyridin-2-yl | CH₃ |
| D-758 | 6-cyanopyridin-2-yl | CH₃ |
| D-759 | 5-hydroxymethylpyridin-2-yl | CH₃ |
| D-760 | 6-chloro-4-trifluoromethyl-pyridin-2-yl | CH₃ |
| D-761 | 6-chloro-4-trifluoromethyl-pyridin-2-yl | CH₃ |
| D-762 | 6-chloro-4-methylpyridin-2-yl | CH₃ |
| D-763 | 2,5-dichloro-6-cyanopyridin-2-yl | CH₃ |
| D-764 | 2,5-dichloro-6-carboxypyridin-2-yl | CH₃ |
| D-765 | 2,5-dichloro-6-methoxycarbonyl-pyridin-2-yl | CH₃ |
| D-766 | 6-trifluoromethylpyridin-2-yl | CH₃ |
| D-767 | 6-methoxycarbonylpyridin-2-yl | CH₃ |
| D-768 | 6-carboxypyridin-2-yl | CH₃ |
| D-769 | 4-phenoxypyridin-2-yl | CH₃ |
| D-770 | 5-phenoxypyridin-2-yl | CH₃ |
| D-771 | 6-phenoxypyridin-2-yl | CH₃ |
| D-772 | 4-phenoxypyrimidin-4-yl | CH₃ |
| D-773 | 4-(4-methylphenoxy)pyrimidin-4-yl | CH₃ |
| D-774 | 4-phenoxypyrimidin-4-yl | CH₃ |
| D-775 | 4-(2-fluorophenoxy)pyrimidin-2-yl | CH₃ |
| D-776 | 4-phenoxypyrimidin-6-yl | CH₃ |
| D-777 | 4-(4-chlorophenoxy)pyrimidin-6-yl | CH₃ |
| D-778 | 4-(2-pyridyloxy)pyrimidin-6-yl | CH₃ |
| D-779 | 4-(6-chloro-2-pyridyloxy)pyrimidin-6-yl | CH₃ |
| D-780 | 4-(3-pyridyloxy)pyrimidin-6-yl | CH₃ |
| D-781 | 4-(2-methyl-3-pyridyloxy)pyrimidin-6-yl | CH₃ |
| D-782 | 4-(4-pyridyloxy)pyrimidin-6-yl | CH₃ |
| D-783 | 5-bromo-2-thienyl | CH₃ |
| D-784 | 5-nitro-2-thienyl | CH₃ |
| D-785 | 2-chloro-3-thienyl | CH₃ |
| D-786 | 2-bromo-3-thienyl | CH₃ |
| D-787 | 1-methyl-3-pyrrolyl | CH₃ |
| D-788 | 1-methyl-2-pyrrolyl | CH₃ |
| D-789 | 1-benzofuran-2-yl | CH₃ |
| D-790 | 1-benzofuran-3-yl | CH₃ |
| D-791 | 1-benzothiopen-2-yl | CH₃ |
| D-792 | 1-benzothiopen-3-yl | CH₃ |
| D-793 | 3-pyrrolyl | CH₃ |
| D-794 | 2-pyrrolyl | CH₃ |
| D-795 | 3-indolyl | CH₃ |
| D-796 | 2-indolyl | CH₃ |
| D-797 | 1-methyl-3-indolyl | CH₃ |
| D-798 | 1-methyl-2-indolyl | CH₃ |
| D-799 | isoxazol-4-yl | CH₃ |
| D-800 | isothiazol-4-yl | CH₃ |
| D-801 | 1,2-benzisoxazol-3-yl | CH₃ |
| D-802 | 1,2-benzisothiazol-3-yl | CH₃ |
| D-803 | 1-methylindazol-3-yl | CH₃ |
| D-804 | benzoxazol-2-yl | CH₃ |
| D-805 | 5-chlorobenzoxazol-2-yl | CH₃ |
| D-806 | 6-fluorobenzoxazol-2-yl | CH₃ |
| D-807 | benzothiazol-2-yl | CH₃ |

TABLE D-continued

| No | R² | R³ |
|---|---|---|
| D-808 | 5-fluorobenzothiazol-2-yl | CH₃ |
| D-809 | 6-fluorobenzothiazol-2-yl | CH₃ |
| D-810 | pyrido[3,2-d]thiazol-2-yl | CH₃ |
| D-811 | (6-chloropyrido)[3,2-d]thiazol-2-yl | CH₃ |
| D-812 | 1-methyl-1,2,3-triazol-5-yl | CH₃ |
| D-813 | 1-methyl-1,2,3-triazol-4-yl | CH₃ |
| D-814 | 1-methyl-1,2,4-triazol-5-yl | CH₃ |
| D-815 | 1-methyl-1,2,3,4-tetrazol-5-yl | CH₃ |
| D-816 | 1-methyl-1,2,3,4-tetrazol-5-yl | CH₃ |
| D-817 | 5-trifluoromethyl-1,3,4-thiadiazol-2-yl | CH₃ |
| D-818 | 6-chlorobenzoxazol-2-yl | CH₃ |
| D-819 | 5-fluorobenzoxazol-2-yl | CH₃ |
| D-820 | 5-nitrothiazol-2-yl | CH₃ |
| D-821 | 1-CH(CH₃)₂-pyrrol-3-yl | CH₃ |
| D-822 | 1-CH(CH₃)₃-pyrrol-3-yl | CH₃ |
| D-823 | 1-cyclopropyl-pyrrol-3-yl | CH₃ |
| D-824 | 1-C₆H₅-pyrrol-3-yl | CH₃ |

The compounds I are suitable as fungicides. They have outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,

Botrytis cinerea (gray mold) on strawberries, vegetables, ornamentals and grapevines, Cercospora arachidicola on peanuts, Erysiphe cichoracearum and Sphaerotheca fuliginea on cucurbits, Erysiphe graminis (powdery mildew) on cereals, Fusarium and Verticillium species on various plants, Helminthosporium species on cereals, Mycosphaerella species on bananas and peanuts, Phytophthora infestans on potatoes and tomatoes, Plasmopara viticola on grapevines, Podosphaera leucotricha on apples, Pseudocercosporella herpotrichoides on wheat and barley, Pseudoperonospora species on hops and cucumbers, Puccinia species on cereals, Pyricularia oryzae on rice, Rhizoctonia species on cotton, rice and lawns, Septoria nodorum on wheat, Uncinula necator on grapevines, Ustilago species on cereals and sugar cane, and Venturia species (scab) on apples and pears.

Moreover, the compounds I are suitable for controlling harmful fungi such as Paecilomyces variotii in the protection of materials (e.g. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

Moreover, the compounds of the formula I are suitable for efficiently controlling animal pests from the classes of the insects, arachnids and nematodes. They can be employed in crop protection and in the hygiene, stored-product and veterinary sector for controlling animal pests. In particular, they are suitable for controlling the following animal pests:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius* abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria, dipterans (Diptera), for example Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa, thrips (Thysanoptera), e.g. Frankliniella fusca, Frankliniella occidentalis, Frankliniella tritici, Scirtothrips citri, Thrips oryzae, Thrips palmi and Thrips tabaci, hymenopterans (Hymenoptera), e.g. Athalia rosae, Atta cephalotes, Atta sexdens, Atta texana, Hoplocampa minuta, Hoplocampa testudinea, Monomorium pharaonis, Solenopsis geminata and Solenopsis invicta, heteropterans (Heteroptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus; Lygus lineolaris, Lygus pratensis, Nezara viridula, Piesma quadrata, Solubea insularis and Thyanta perditor, homopterans (Homoptera), e.g. Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum and Viteus vitifolii, termites (Isoptera), e.g. Calotermes flavicollis, Leucotermes flavipes, Reticulitermes lucifugus and Termes natalensis, orthopterans (Orthoptera), e.g. Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus, Arachnoidea, such as arachnids (Acarina), e.g. Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius and Tetranychus urticae, nematodes such as root knot nematodes, e.g. Meloidogyne hapla, Meloidogyne incognita, Meloidogyne javanica, cyst-forming nematodes, e.g. Globodera rostochiensis, Heterodera avenae, Heterodera glycines, Heterodera schachtii, Heterodera trifolii, stem eelworms and foliar nematodes, e.g. Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus and Pratylenchus goodeyi.

The rate of application of active ingredient for controlling animal pests is from 0.1 to 2.0, preferably 0.2 to 1.0; kg/ha under field conditions.

The compounds I can be converted into the customary formulations, e.g. solutions, emulsions, suspensions, dusts, powders, pastes and granules. The use form depends on the particular purpose; in any case, it should guarantee a fine and uniform distribution of the compound according to the invention.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly-disperse silica, silicates); emulsifiers such as nonionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenol ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-a-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for scattering, or granules, by means of spraying, atomizing, dusting, scattering or pouring. The use forms depend entirely on the intended purposes; in any case, these are intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These agents can be admixed with the agents according to the invention in a weight ratio of 1:10 to 10:1.

In the use form as fungicides, the compositions according to the invention can also be present together with other active ingredients, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylene-bisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1- (3,4-dichloroanilino)-1-formylamino-2,2,2-trichloroethane; 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurines such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate, methyl-E-methoxyimino-[α-(2-phenoxyphenyl)]acetamide, methyl E-methoxyimino-[α-(2,5-dimethylphenoxy)-o-tolyl]acetamide, anilinopyrimidines such as N-(4,6-dimethylpyrimidin-2-yl)aniline, N-[4-methyl-6-(1-propynyl)pyrimidin-2-yl] aniline, N-[4-methyl-6-cyclopropylpyrimidin-2-yl] aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxyphenyl)acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl) methylsilyl)methyl)-1H-1,2,4-triazole.

SYNTHENSIS EXAMPLES

With due modification of the starting materials, the protocols shown in the synthesis examples below were used for obtaining further compounds I. The resulting compounds, together with physical data, are listed in the tables which follow.

Example 1

Preparation of N-methyl-5-[2-(o-tolyloxy-methylene) phenyl]-1,3-oxazolidin-2,4-dione At about 70° C., a solution of 1.8 g (6 mmol) of triphosgene in 15 ml of anhydrous toluene was added dropwise to a solution of 5 g (17 mmol) of methyl α-hydroxy-α-2-(o-tolyloxy-methylene)phenylacetate [cf. WO-A 96/07, 633] in 80 ml of anhydrous toluene. The solution was stirred for a further three hours at 70° C. and for 14 hours at about 20–25° C., and the solvent was then distilled off at about 250 mbar. At about 20–25° C., 8 ml of a 2 N methylamine solution in tetrahydrofuran (THF) were added dropwise to the solution of the residue in 40 ml of anhydrous THF. The solution was poured onto ice and then extracted with methyl tert-butyl ether. The organic phases gave, after drying and distillative removal of the solvent, 3.0 g of the title compound as a pale yellow oil.

$^1$H-NMR (CDCl$_3$, δ in ppm): 2.3 (s, 3H); 3.3 (s, 3H), 5.2 (s, 2H); 5.7 (s, 1H); 6.8–8.5 (m, br, 8H).

Examples of Action Against Harmful Fungi

The fungicidal activity of the compounds of the formula I was demonstrated by the following experiments:

The active compounds, separately or together, were formulated as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to the desired concentration.

Use Example 1—Action Against Mildew of Wheat

Leaves of potted wheat seedlings cv. "Frühgold" were sprayed to runoff point with an aqueous active compound formulation which had been made up from a stock solution of 10% of active compound, 63% of cyclohexanone and 27% of emulsifier. 24 hours after the spray coating had dried on, the leaves were dusted with spores of mildew of wheat (Erysiphe graminis forma specialis tritici). The test plants were subsequently kept in a greenhouse at from 20 to 24° C. and from 60 to 90% relative atmospheric humidity. After 7 days, the extent of mildew development was determined visually in % infection of the total leaf area.

In this test, the plants which had been treated with 250 ppm of the compound of Example 1 showed 15% infection, while the untreated plants were infected to 80%.

Examples of Action Against Animal Pests

The action of compounds of the formula I against animal pests was demonstrated by the following experiments:

The active compounds were fomulated a. as a 0.1% strength solution in acetone or b. as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted in the case of a. with acetone and in the case of b. with water to give the desired concentration.

After the experiments had ended, in each case the lowest concentration was determined at which the compounds still caused an 80 to 100% inhibition or mortality in comparison with untreated control experiments (critical or minimum concentration).

We claim:

1. A heterocyclyl-substituted phenyl compound of the formula I,

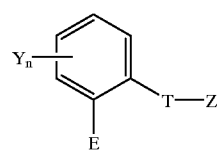

(I)

where:

Y is halogen, $C_1$–$C_4$-alkyl, $C_1$–$C_4$-haloalkyl or $C_1$–$C_4$-alkoxy;

n is 0, 1 or 2, where the radicals Y may be different if n=2;

E is a group A or B,

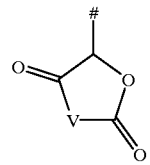

(A)

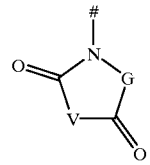

(B)

where # denotes the bond to the phenyl ring;
V is oxygen or N—$R^\alpha$, and
G is N—$R^\beta$, where
  $R^\alpha$ is $C_1$–$C_4$-alkyl, $C_1$–$C_4$-haloalkyl, $C_3$–$C_6$-cycloalkyl or is arylmethylene with or without substitution;
  $R^\beta$ is hydrogen or a radical $R^\alpha$;
T is oxygen or oxymethylene;
Z is a group X, N=CWR$^1$ or N=C(R$^1$)—C(R$^2$)=NOR$^3$;
  X is heterocyclyl with or without substitution, aryl with or without substitution, hetaryl with or without substitution, arylmethylene with or without substitution or hetarylmethylene with or without substitution;
  W is $C_1$–$C_6$-alkyl with or without substitution, $C_2$–$C_6$-alkenyl with or without substitution, $C_2$–$C_6$-alkynyl with or without substitution, $C_3$–$C_6$-cycloalkyl with or without substitution, $C_3$–$C_6$-cycloalkenyl with or without substitution, heterocyclyl with or without substitution, aryl with or without substitution or hetaryl with or without substitution;
  $R^1$ is hydrogen, cyano, $C_1$–$C_4$-alkyl, $C_1$–$C_4$-haloalkyl, $C_1$–$C_4$-alkoxy, $C_1$–$C_4$-alkoxy-$C_1$–$C_4$-alkyl, $C_3$–$C_6$-cycloalkyl;
  $R^2$ is hydrogen, cyano, halogen, C(R$^d$)=NOR$^3$ or W, OW, SW or NR$^c$W, where
    $R^c$ is hydrogen, $C_1$–$C_6$-alkyl, $C_2$–$C_6$-alkenyl or $C_2$–$C_6$-alkynyl and
    $R^d$ is hydrogen or $C_1$–$C_6$-alkyl;
  $R^3$ is hydrogen, $C_1$–$C_6$-alkyl with or without substitution, $C_2$–$C_6$-alkenyl with or without substitution or $C_2$–$C_6$-alkynyl with or without substitution.

2. A process for preparing compounds of the formula IAa,

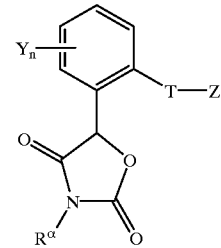

(IAa)

where $R^\alpha$, Y, n, T and Z are each as defined in claim 1, which comprises acylating alkyl α-hydorxy-α-phenylacetates of the formula IIA,

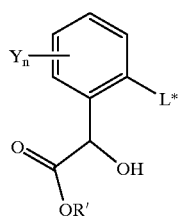
(IIA)

where

L* is CH₂L' or a group L', where
L' is a nucleophilically cleavable group and
R' is $C_1$–$C_4$-alkyl, with phosgene or a phosgene equivalent to give compounds of the formula IIIA

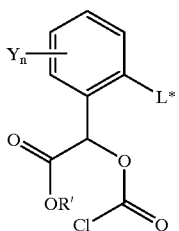
(IIIA)

which are cyclized by reaction with primary amines of the formula IVa $$H_2N—R^\alpha \quad (IVa)$$

and, if the cyclization to give the oxazolidinediones of the formula VAa

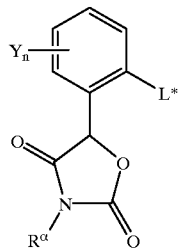
(VAa)

does not proceed unaided, by hydrolysis of the resulting ester amide of the formula VIA

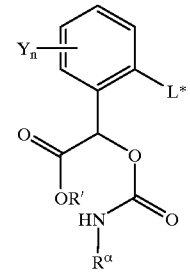
(VIA)

and subsequent treatment with acid, and converting VAa into IAa by reaction with compounds Z—OH.

3. A process for preparing triazolidinediones of the formula IBa,

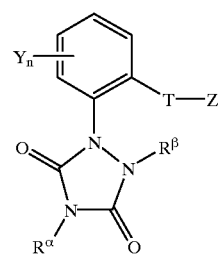
(IBa)

which comprises converting phenylhydrazines of the formula IIB

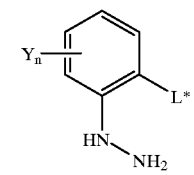
(IIB)

by reaction with alkyl chloroformates into carbamates of the formula IIIB,

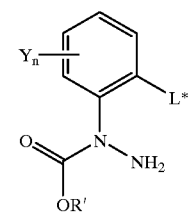
(IIIB)

where R' is $C_1$–$C_4$-alkyl, acylating these with phosgene or a phosgene equivalent to give compounds of the formula VB (VB)

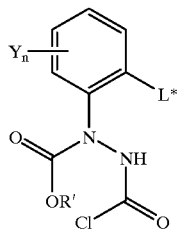

cyclizing these by reaction with primary amines of the formula IVa as claimed in claim 2 and, if the cyclization to the triazolidinediones of the formula VIBa (VIBa)

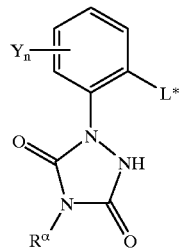

does not proceed unaided, by hydrolysis of the resulting ester amide of the formula VIIB (VIIB)

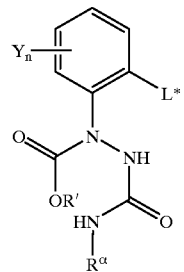

and subsequent treatment with acid and, if $R^\beta$ in the formula IBa is not hydrogen, alkylating VIBa to compounds VIBa', (VIBa')

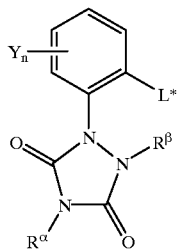

where $R^\beta$ is not hydrogen and converting VIBa or VIBa' into IBa by reaction with compounds Z—OH.

4. An intermediate of the formula 1, (1)

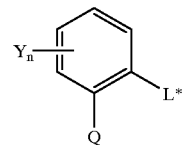

where

Q is a group A as set forth in claim 1 or
is CH(COOR')OCOCl, CH(COOH)OCOCl, CH(COOR')OCONHR$^\alpha$ or CH(COOH)OCONHR$^\alpha$,
where
R' is $C_1$–$C_4$-alkyl;

L* is hydroxyl, $CH_3$, $CH_2L'$ or a group L', where
L' is a nucleophilically cleavable group and
Y and n are each as defined in claim 1.

5. An intermediate of the formula VIBa, (VIBa)

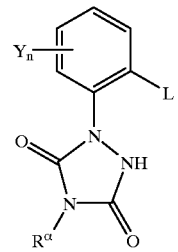

where

L is $CH_3$, $CH_2L'$, nitro or alkylsulfonate or arylsulfonate, where
L' is a nucleophilically cleavable group and
Y, n and $R^\alpha$ are each as defined in claim 1.

6. A composition suitable for controlling animal pests or harmful fungi comprising a solid or liquid carrier and a compound of the formula I as claimed in claim 1.

7. A method for controlling harmful fungi, which comprises treating the fungi or the materials, plants, the soil or the seeds to be protected against fungal attack with an effective amount of a compound of the formula I as claimed in claim 1.

8. A method for controlling animal pests, which comprises treating the animal pests or the materials, plants, the soil or the seeds to be protected against them with an effective amount of a compound of the formula I as claimed in claim 1.

* * * * *

UNITED STATES PATENT AND TRADEMARK OFFICE
CERTIFICATE OF CORRECTION

PATENT NO. : 6,200,997 B1
DATED : March 13, 2001
INVENTOR(S) : Gypser et al.

It is certified that error appears in the above-identified patent and that said Letters Patent is hereby corrected as shown below:

Title page,
Item [30], in the Foreign Application Priority Data, "(GB)" should be -- (DE) --.

Signed and Sealed this

Second Day of October, 2001

Attest:

NICHOLAS P. GODICI
Attesting Officer  Acting Director of the United States Patent and Trademark Office